US011752176B2

(12) United States Patent
Murry et al.

(10) Patent No.: US 11,752,176 B2
(45) Date of Patent: Sep. 12, 2023

(54) METHODS AND COMPOSITIONS FOR ENHANCING CARDIOMYOCYTE MATURATION AND ENGRAFTMENT

(71) Applicants: UNIVERSITY OF WASHINGTON, Seattle, WA (US); CAMBRIDGE ENTERPRISE LIMITED, Cambridge (GB)

(72) Inventors: Charles E. Murry, Seattle, WA (US); Sanjay Sinha, Cambridge (GB); Johannes Bargehr, Cambridge (GB)

(73) Assignees: University of Washington, Seattle, WA (US); Cambridge Enterprise Limited, Cambridge (GB)

(*) Notice: Subject to any disclaimer, the term of this patent is extended or adjusted under 35 U.S.C. 154(b) by 707 days.

(21) Appl. No.: 16/493,888

(22) PCT Filed: Mar. 15, 2018

(86) PCT No.: PCT/US2018/022659
§ 371 (c)(1),
(2) Date: Sep. 13, 2019

(87) PCT Pub. No.: WO2018/170280
PCT Pub. Date: Sep. 20, 2018

(65) Prior Publication Data
US 2020/0085880 A1 Mar. 19, 2020

Related U.S. Application Data

(60) Provisional application No. 62/471,737, filed on Mar. 15, 2017.

(51) Int. Cl.
*A61K 35/34* (2015.01)
*A61K 35/545* (2015.01)
*A61K 31/4409* (2006.01)
*A61K 38/13* (2006.01)
*A61K 38/30* (2006.01)
*A61P 9/10* (2006.01)
*A61P 9/04* (2006.01)
*C12N 5/00* (2006.01)

(52) U.S. Cl.
CPC .......... *A61K 35/34* (2013.01); *A61K 31/4409* (2013.01); *A61K 35/545* (2013.01); *A61K 38/13* (2013.01); *A61K 38/30* (2013.01); *A61P 9/04* (2018.01); *A61P 9/10* (2018.01)

(58) Field of Classification Search
CPC .. A61K 35/34; A61K 35/545; A61K 31/4409; A61P 9/10
See application file for complete search history.

(56) References Cited

U.S. PATENT DOCUMENTS

| 8,982,094 B2 | 3/2015 | Pi et al. | |
| 9,117,340 B2 | 8/2015 | Popovich et al. | |
| 2006/0239985 A1 | 10/2006 | Croissant et al. | |
| 2007/0166288 A1* | 7/2007 | Murry | A61K 38/55 |
| | | | 435/366 |
| 2008/0089867 A1 | 4/2008 | Fernandes et al. | |
| 2012/0157381 A1 | 6/2012 | Spees | |
| 2014/0313154 A1 | 10/2014 | Bengtsson et al. | |
| 2016/0215263 A1 | 7/2016 | Keller et al. | |

FOREIGN PATENT DOCUMENTS

| JP | 2016534738 A | 11/2016 | |
| WO | 2015035506 A1 | 3/2015 | |
| WO | WO-2015035506 A1 * | 3/2015 | ........... C12N 5/0657 |

OTHER PUBLICATIONS

Moerkamp et al (2016. Stem Cell Research 7:174.*
Gerbin et al., "Enhanced electrical integration of engineered human myocardium via intramyocardial versus epicardial delivery in infarcted rat hearts." PLoS One 10(7): e0131446 (2015).
Braunwald "Cardiovascular medicine at the turn of the millennium: triumphs, concerns, and opportunities" The New England Journal of Medicine 337(19):1360-1369 (1997).
Burridge et al., "Chemically defined and small molecule-based generation of human cardiomyocytes" Nature Methods 11(8): 855-860 (2014).
Cai et al., "A myocardial lineage derives from Tbx18 epicardial cells" Nature 454(7200):104-108 (2008).
Cheung et al., Generation of human vascular smooth muscle sub-types provides insight into embryological origin-dependent disease susceptibility. Nature Biotechnology 30(2):165-173 (2012).
Chong et al., "Human embryonic stem cell-derived cardiomyocytes regenerate non-human primate hearts", Nature 510(7504): 273-277 (2014).
Dettman et al., "Common epicardial origin of coronary vascular smooth muscle, perivascular fibroblasts, and intermyocardial fibroblasts in the avian heart" Developmental Biology 193(2):169-181 (1998).
Eid et al., "Role of epicardial mesothelial cells in the modification of phenotype and function of adult rat ventricular myocytes in primary coculture" Circulation Research 71(1):40-50 (1992).
Guadix et al., "In vivo and in vitro analysis of the vasculogenic potential of avian proepicardial and epicardial cells" Developmental Dynamics 235(4): 1014-1026 (2006).
Gittenberger De Groot et al. "Epicardial outgrowth inhibition leads to compensatory mesothelial outflow tract collar and abnormal cardiac septation and coronary formation", Circulation Research 87(11):969-971 (2000).

(Continued)

*Primary Examiner* — Zachary C Howard
(74) *Attorney, Agent, or Firm* — Nixon Peabody LLP; Mark J. FitzGerald; David S. Resnick

(57) ABSTRACT

Provided herein are methods and compositions comprising cardiomyocytes and epicardial cells for the treatment of cardiac disease.

15 Claims, 48 Drawing Sheets

(56) References Cited

OTHER PUBLICATIONS

Gittenberger De Groot et al., "Epicardium-derived cells contribute a novel population to the myocardial wall and the atrioventricular cushions" Circulation Research 82(10):1043-1052 (1998).
Hedhli et al., "Endothelium-derived neuregulin protects the heart against ischemic injury", Circulation 123(20):2254-2262 (2011).
Hofsteen et al., "Quantitative proteomics identify DAB2 as a cardiac developmental regulator that inhibits WNT/beta-catenin signaling" Proceedings of the National Academy of Sciences of the United States of America 113(4):1002-1007 (2016).
Ieda et al., "Cardiac fibroblasts regulate myocardial proliferation through beta-1 integrin signaling" Developmental Cell 16(2):233-244 (2009).
Laflamme et al., "Cardiomyocytes derived from human embryonic stem cells in pro-survival factors enhance function of infarcted rat hearts" Nature Biotechnology 25(9):1015-1024 (2007).
Lepilina et al., "A dynamic epicardial injury response supports progenitor cell activity during zebrafish heart regeneration" Cell 127(3):607-619 (2006).
Leucker et al.,, "Endothelial-cardiomyocyte crosstalk enhances pharmacological cardioprotection" Journal of Molecular and Cellular Cardiology 51(5):803-811 (2011).
Lian et al., "Robust cardiomyocyte differentiation from human pluripotent stem cells via temporal modulation of canonical Wnt signaling" Proceedings of the National Academy of Sciences of the United States of America 109 (27): E1848-1857 (2012).
Männer "Does the subepicardial mesenchyme contribute myocardioblasts to the myocardium of the chick embryo heart? A quail-chick chimera study tracing the fate of the epicardial primordium" The Anatomical Record 255(2):212-226 (1999).
McMurray et al., "Clinical epidemiology of heart failure: public and private health burden" European Heart Journal 19 Suppl P:P9-16 (1998).
Moore-Morris et al., "Resident fibroblast lineages mediate pressure overload-induced cardiac fibrosis" The Journal of Clinical Investigation 124(7):2921-2934 (2014).
Mozaffarian et al., "Heart Disease and Stroke Statistics 2016 Update: A Report From the American Heart Association" Circulation 133:e38-360 (2016).
Ogle et al., "Distilling complexity to advance cardiac tissue engineering" Science Translational Medicine (342):342ps313(2016).
Orlova et al., "Generation, expansion and functional analysis of endothelial cells and pericytes derived from human pluripotent stem cells" Nature Protocols 9(6):1514-1531 (2014).
Palpant et al., "Cardiac development in zebrafish and human embryonic stem cells is inhibited by exposure to tobacco cigarettes and e-cigarettes", PloS One 10(5): e0126259 (2015).
Patsch et al., "Generation of vascular endothelial and smooth muscle cells from human pluripotent stem cells." Nature Cell Biology 17(8): 994-1003 (2015).
Pittenger et al., "Multilineage potential of adult human mesenchymal stem cells", Science 284(5411): 143-147 (1999).
Porrello et al., "Transient regenerative potential of the neonatal mouse heart" Science 331 (6020):1078-1080 (2011).
Ruan et al. "Mechanical Stress Promotes Maturation of Human Myocardium From Pluripotent Stem Cell-Derived Progenitors" Stem Cells 33(7):2148-2157 (2015).
Ruiz-Villalba et al., "Interacting resident epicardium-derived fibroblasts and recruited bone marrow cells form myocardial infarction scar", Journal of the American College of Cardiology 65(19):2057-2066 (2015).
Shiba et al., "Allogeneic transplantation of iPS cell-derived cardiomyocytes regenerates primate hearts" Nature 538 (7625): 388-391 (2016).
Shiba et al., "Human ES cell-derived cardiomyocytes electrically couple and suppress arrhythmias in injured hearts" Nature 489(7415): 322-325 (2012).
Van Den Berg et al., "Transcriptome of human foetal heart compared with cardiomyocytes from pluripotent stem cells" Development 142(18): 3231-3238 (2015).
Wang et al., "Fibronectin is deposited by injury-activated epicardial cells and is necessary for zebrafish heart regeneration" Developmental Biology 382(2):427-435 (2013).
Weeke-Klimp et al., "Epicardium-derived cells enhance proliferation, cellular maturation and alignment, of cardiomyocytes" Journal of Molecular and Cellular Cardiology 49(4):606-616 (2010).
Winter et al., "A new direction for cardiac regeneration therapy: application of synergistically acting epicardium-derived cells and cardiomyocyte progenitor cells", Circulation Heart Failure 2(6):643-653 (2009).
Winter et al., "Preservation of left ventricular function and attenuation of remodeling after transplantation of human epicardium-derived cells into the infarcted mouse heart", Circulation 116(8):917-927 (2007).
Ye et al. "Cardiac repair in a porcine model of acute myocardial infarction with human induced pluripotent stem cell-derived cardiovascular cells", Cell Stem Cell 15(6):750-761 (2014).
Witty et al. "Generation of the epicardial lineage from human pluripotent stem cells." Nature Biotechnology 32(10): 1026-1035 (2014).
Zhao et al., "Efficient differentiation of TBX18+/WT1+ epicardial-like cells from human pluripotent stem cells using small molecular compounds." Stem cells and Development 26(7): 528-540 (2017).
Bao et al., "Long-term self-renewing human epicardial cells generated from pluripotent stem cells under defined xeno-free conditions." Nature Biomedical Engineering 1(1): 1-12 (2016).
Iyer et al., "Robust derivation of epicardium and its differentiated smooth muscle cell progeny from human pluripotent stem cells." Development 142(8): 1528-1541 (2015).
Zhou et al., "Adult mouse epicardium modulates myocardial injury by secreting paracrine factors." The Journal of Clinical Investigation 121.5 (2011): 1894-1904.
Bargehr et al. "Human embryonic stem cell derived epicardial cells advance cardiomyocyte-based heart regeneration." European Heart Journal 38.suppl_1 (2017).
Wei et al. "Epicardial FSTL1 reconstitution regenerates the adult mammalian heart." Nature 525(7570): 479-485 (2015).
Holt-Casper et al. "Novel xeno-free human heart matrix-derived three-dimensional scaffolds" J Transl Med 13, 194, 1-15 (2015). https://doi.org/10.1186/s12967-015-0559-0.

* cited by examiner

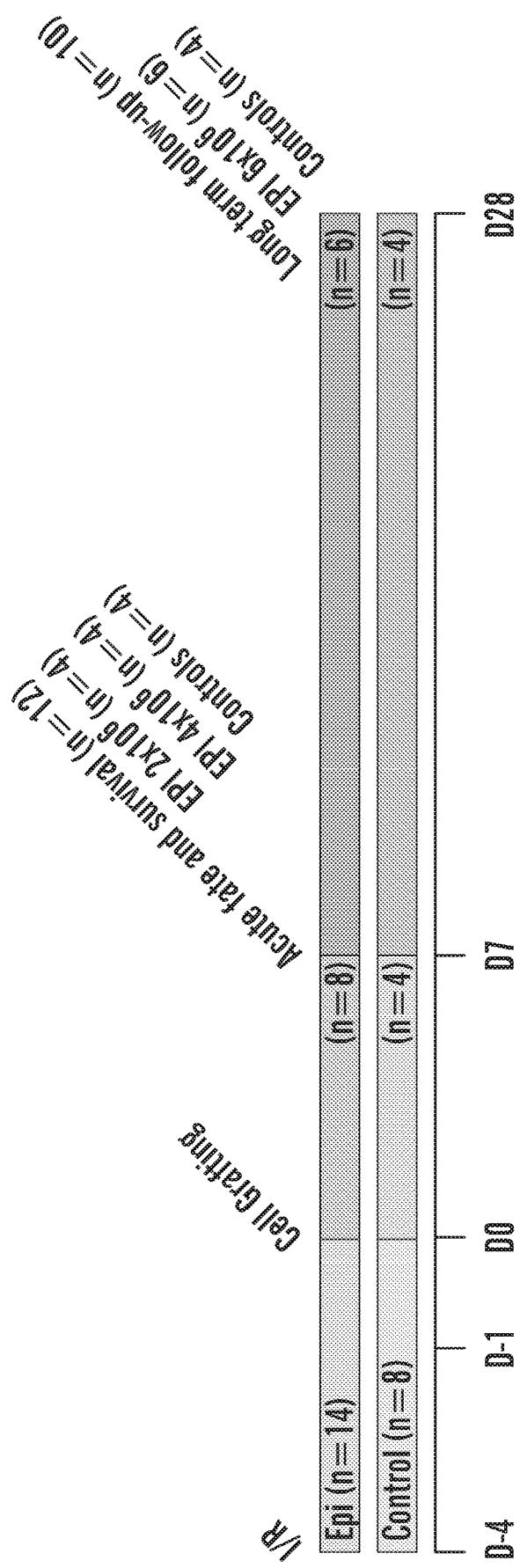
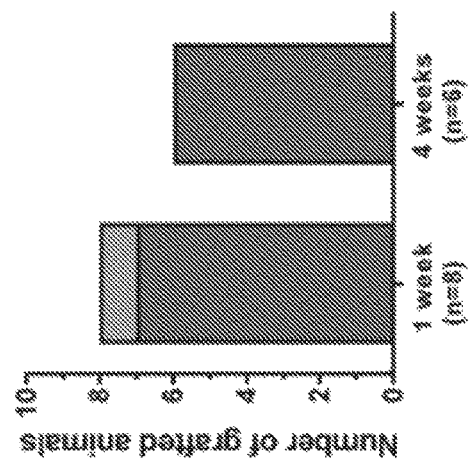
FIG. 9A
FIG. 9B

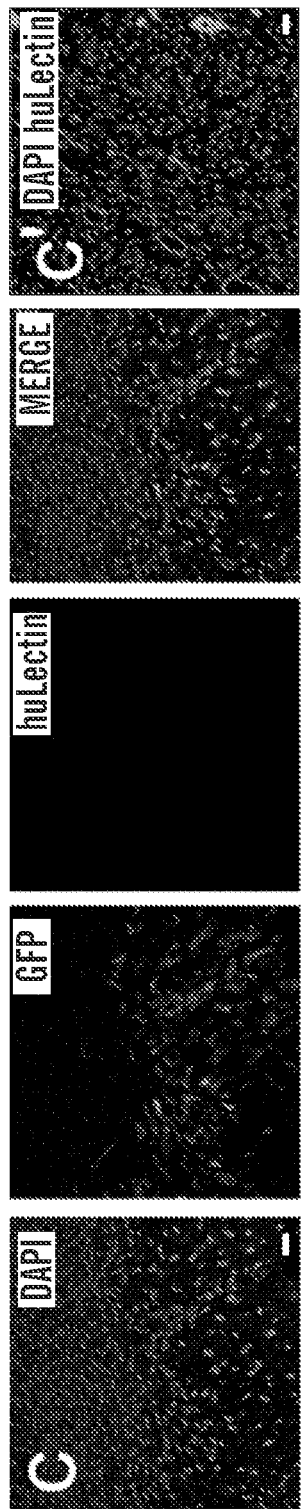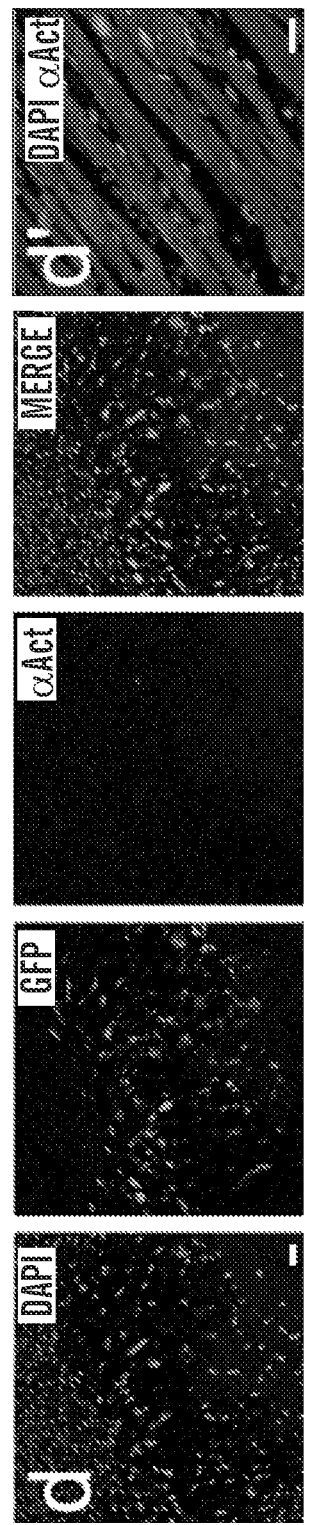

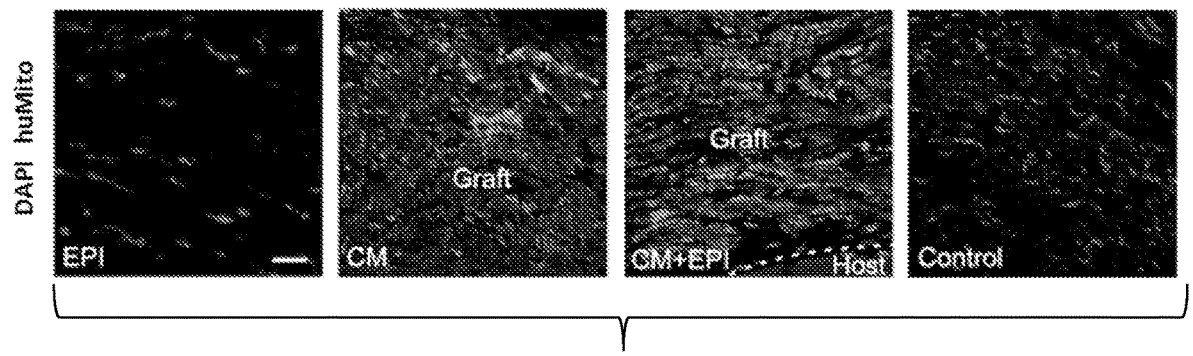
FIG. 12A
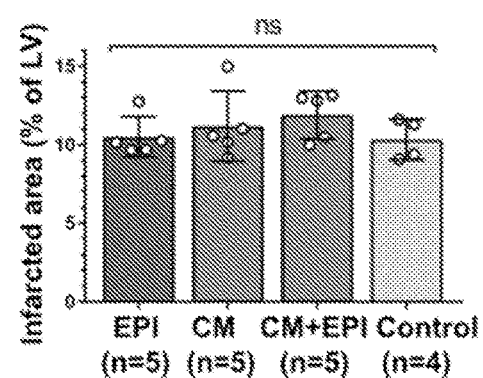
FIG. 12B
FIG. 12C

|  | Test 1 | | | |
|---|---|---|---|---|
|  | Uninjured (n=6) | Day 4 (n=6) | Day 28 (n=6) | Total (n=18) |
| Interobserver agreement | 0.77 (-0.18-0.96) | 0.94 (0.56-0.99) | 0.84 (-0.39-0.97) | 0.95 (0.88-0.98) |

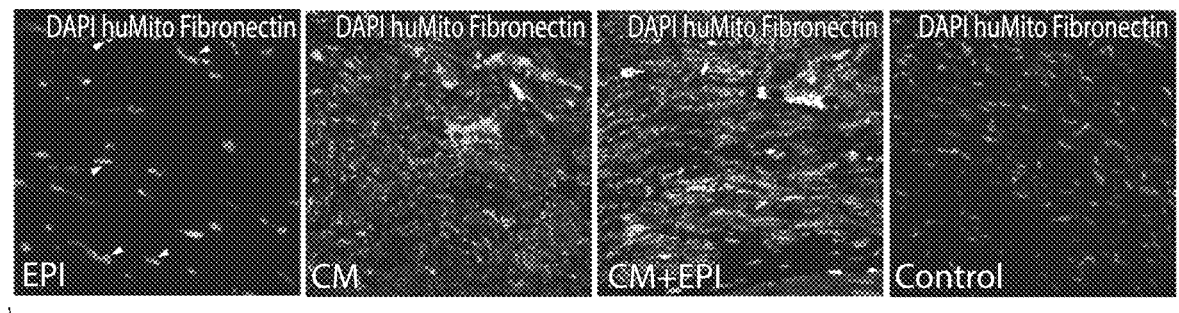
FIG. 16
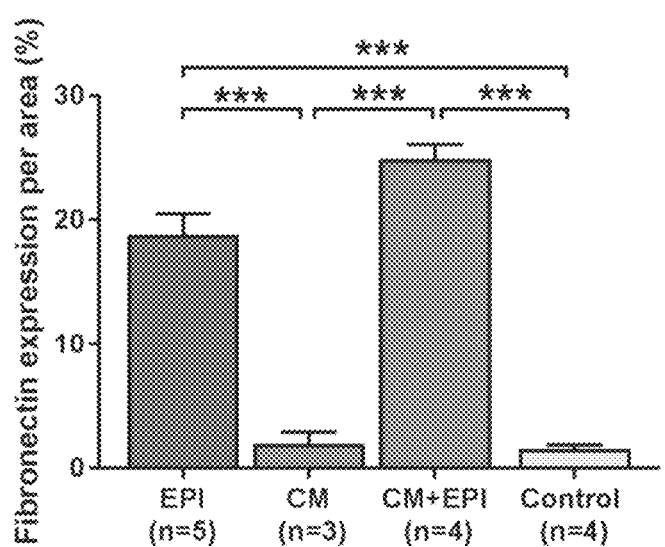
FIG. 16 con't

METHODS AND COMPOSITIONS FOR ENHANCING CARDIOMYOCYTE MATURATION AND ENGRAFTMENT

CROSS-REFERENCE TO RELATED APPLICATIONS

This Application is a 35 U.S.C. § 371 National Phase Entry Applications of International Application No. PCT/US2018/022659 filed Mar. 15, 2018, which designates the U.S. and claims benefit under 35 U.S.C. § 119(e) of the U.S. Provisional Application No. 62/471,737 filed Mar. 15, 2017, the contents of each of which are incorporated herein by reference in their entireties.

GOVERNMENT SUPPORT

This invention was made with government support under Grant No. P01 HL094374, awarded by the National Institutes of Health. The government has certain rights in the invention.

FIELD OF THE INVENTION

The field of the invention relates to methods and compositions for treating injury to the myocardium and/or heart failure.

BACKGROUND

Despite major advances in the treatment of heart failure due to systolic impairment, therapeutic approaches have fallen short of addressing the cause of the problem; injury of the mammalian heart leads to irreversible loss of contractile myocardial tissue which is incapable of regeneration. At the turn of the millennium heart failure was widely identified as an emerging epidemic. To date 5.6 million patients in the US alone and 23 million worldwide are suffering from heart failure with 50% dying within 5 years after being diagnosed. Current treatment is limited to ameliorating symptoms and slowing the natural progression of the disease but fails to compensate for the loss of contractile myocardium post-injury.

SUMMARY

Provided herein, in part, are methods and compositions comprising epicardial cells and cardiomyocytes for engraftment and subsequent regeneration of functional heart tissue following injury to the myocardium.

Accordingly, one aspect provided herein relates to a transplant composition comprising human cardiomyocytes and in vitro-differentiated human epicardial cells or the differentiated progeny of such human epicardial cells.

In one embodiment of this aspect and all other aspects provided herein, the transplant composition comprises human cardiomyocytes that are in vitro-differentiated.

In another embodiment of this aspect and all other aspects provided herein, the epicardial cells or their progeny, the cardiomyocytes, or both, are differentiated from embryonic stem cells or from induced pluripotent stem cells.

In another embodiment of this aspect and all other aspects provided herein, the epicardial cells or their progeny, the cardiomyocytes, or both, are differentiated from iPS cells autologous to a transplant recipient.

In another embodiment of this aspect and all other aspects provided herein, the epicardial cells express fibronectin.

In another embodiment of this aspect and all other aspects provided herein, the transplant compositions further comprises one or more of ZVAD-FMK, Bcl-XL, cyclosporine A, pinacidil, and IGF-1.

In another embodiment of this aspect and all other aspects provided herein, the cardiomyocytes are present at a ratio of about 2:1 relative to the epicardial cells or progeny thereof.

In another embodiment of this aspect and all other aspects provided herein, the transplant composition engrafts at least 20% more efficiently than a similar composition lacking the epicardial cells or their progeny.

Another aspect provided herein relates to a cardiac delivery device comprising a transplant composition as described herein or as demonstrated in the working Examples.

Also provided herein, in another aspect, is a tissue particle comprising a human cardiomyocyte in physical association with an in vitro-differentiated human epicardial cell or differentiated progeny thereof, in a culture medium or a cocktail comprising one or more of ZVAD-FMK, Bcl-XL, cyclosporine A, pinacidil, and IGF-1.

In one embodiment of this aspect and all other aspects described herein, the tissue particle comprises from 2 to 2500 cells.

In another embodiment of this aspect and all other aspects provided herein, the ratio of cardiomyocytes to epicardial cells or differentiated progeny thereof is about 2:1.

In another embodiment of this aspect and all other aspects provided herein, the epicardial cell, the cardiomyocyte, or both is/are differentiated from an embryonic stem cell or an induced pluripotent stem cell.

In another embodiment of this aspect and all other aspects provided herein, the cardiomyocyte is in vitro differentiated.

In another embodiment of this aspect and all other aspects provided herein, the cardiomyocyte(s), the epicardial cell(s), or both is/are in vitro differentiated from an embryonic stem cell or an induced pluripotent stem cell.

Another aspect provided herein relates to a method of promoting engraftment of cardiomyocytes into cardiac tissue, comprising administering to cardiac tissue of a subject in need thereof a composition comprising epicardial cells in admixture with cardiomyocytes.

In one embodiment of this aspect and all other aspects provided herein, a cardiac infarction (i.e., a myocardial infarction).

In another embodiment of this aspect and all other aspects provided herein, the composition comprising epicardial cells in admixture with cardiomyocytes is a transplant composition or comprises a tissue particle as described in any of the aspects provided herein.

Another aspect provided herein relates to a method of promoting a mature phenotype of transplanted human cardiomyocytes, the method comprising administering to cardiac tissue of a subject in need thereof, a composition comprising human cardiomyocytes in admixture with human epicardial cells.

In one embodiment of this aspect and all other aspect provided herein, the subject has suffered a cardiac infarction.

In another embodiment of this aspect and all other aspects provided herein, the composition comprising human cardiomyocytes in admixture with human epicardial cells is a transplant composition or comprises a tissue particle as described in any of the aspects described herein.

In another embodiment of this aspect and all other aspects provided herein, the cardiomyocyte maturity is indicated by one or more of an increase in sarcomere length, an increase in cardiomyocyte diameter or length, expression of the cardiac isoform, cTnT, of troponin, and connexin 43 expression when cardiomyocytes are transplanted in admixture with epicardial cells, relative to cardiomyocyte transplantation alone.

Also provided herein, in another aspect, is a method of increasing microvascular density at the site of a cardiac cardiomyocyte transplant, the method comprising administering to cardiac tissue of a subject in need thereof a composition comprising human cardiomyocytes in admixture with human epicardial cells.

In one embodiment of this aspect and all other aspects provided herein, the subject has suffered a cardiac infarction.

In another embodiment of this aspect and all other aspects provided herein, the composition comprising human cardiomyocytes in admixture with human epicardial cells is a transplant composition or comprises a tissue particle as described herein.

In another embodiment of this aspect and all other aspects provided herein, microvascular density or a marker thereof is increased by at least 10% relative to that occurring when a cardiomyocyte transplant lacking epicardial cells is administered.

In another embodiment of this aspect and all other aspects provided herein, microvascular density is indicated by expression of one or more of CD31, VE cadherin, von Willebrand factor (vWF) or by staining with a lectin that preferentially binds vascular endothelium.

Another aspect provided herein relates to a method of increasing cardiomyocyte graft size in a cardiac tissue, the method comprising administering to cardiac tissue of a subject in need thereof a composition comprising human cardiomyocytes in admixture with human epicardial cells.

In one embodiment of this aspect and all other aspects provided herein, the subject has suffered a cardiac infarction (i.e., a myocardial infarction).

In another embodiment of this aspect and all other aspects provided herein, the composition comprising human cardiomyocytes in admixture with human epicardial cells is a transplant composition or comprises a tissue particle as described herein.

In another embodiment of this aspect and all other aspects provided herein, cardiomyocyte graft size is increased at least 10% by administering a composition comprising human cardiomyocytes in admixture with human epicardial cells relative to administration of a composition comprising substantially the same number of human cardiomyocytes but lacking human epicardial cells.

Also provided herein, in another aspect, is a method of promoting the maturity of in vitro-differentiated cardiomyocytes, the method comprising culturing in vitro differentiated cardiomyocytes in the presence of epicardial cells, differentiated progeny thereof, or epicardial cell conditioned medium.

In one embodiment of this aspect and all other aspects provided herein, the cardiomyocytes and epicardial cells are human.

In another embodiment of this aspect and all other aspects provided herein, the epicardial cells are in vitro differentiated.

In another embodiment of this aspect and all other aspects provided herein, the epicardial cells, the cardiomyocytes or both are in vitro differentiated from embryonic stem cells or from induced pluripotent stem cells.

In another embodiment of this aspect and all other aspects provided herein, cardiomyocyte maturity is indicated by one or more of an increase in sarcomere length in an engineered tissue or in a graft, an increase in cardiomyocyte diameter or length, expression of the cardiac isoform, cardiac troponin T (cTnT), of troponin, and connexin 43 expression.

Another aspect provided herein relates to a method of promoting electrical connection between transplanted and recipient cardiomyocytes, the method comprising administering a transplant composition comprising cardiomyocytes in admixture with epicardial cells.

In one embodiment of this aspect and all other aspects provided herein, the cardiomyocytes and epicardial cells are human.

In another embodiment of this aspect and all other aspects provided herein, the cardiomyocytes, the epicardial cells, or both are in vitro differentiated.

In another embodiment of this aspect and all other aspects provided herein, the epicardial cells, the cardiomyocytes or both are in vitro differentiated from embryonic stem cells or from induced pluripotent stem cells.

In another embodiment of this aspect and all other aspects provided herein, the expression of connexin 43 is increased in transplanted cardiomyocytes administered in admixture with epicardial cells relative to connexin 43 expression in transplanted cardiomyocytes administered without epicardial cells.

Also provided herein, in another aspect, is a method of increasing the proliferation of transplanted cardiomyocytes, the method comprising administering a transplant composition comprising cardiomyocytes in admixture with epicardial cells or the differentiated progeny thereof.

In another embodiment of this aspect and all other aspects provided herein, the cardiomyocytes, the epicardial cells or both are in vitro differentiated.

In another embodiment of this aspect and all other aspects provided herein, the cardiomyocytes, the epicardial cells or both are in vitro differentiated from embryonic stem cells or from induced pluripotent stem cells.

In another embodiment of this aspect and all other aspects provided herein, the transplant composition comprises a composition of any one of claims 1-8, or comprises a tissue particle of any one of claims 10-15.

Another aspect provided herein relates to a method of treating a cardiac infarction, the method comprising administering to cardiac tissue of a subject in need thereof a composition or a tissue particle as described herein.

In one embodiment of this aspect and all other aspects described herein, one or more of engraftment, proliferation, maturity or function of transplanted cardiomyocytes is improved relative to administration of a composition comprising substantially the same number of cardiomyocytes, but lacking epicardial cells.

Another aspect provided herein relates to a method of making a cardiomyocyte transplant composition, the method comprising: (i) providing a preparation of in vitro-differentiated human cardiomyocytes; (ii) providing a preparation of in vitro-differentiated human epicardial cells; and (iii) admixing the cardiomyocytes with the epicardial cells in a composition comprising one or more of ZVAD-FMK, Bcl-XL, cyclosporin A, pinacidil and IGF-1.

In one embodiment of this aspect and all other aspects provided herein, the cardiomyocytes, the epicardial cells, or both are differentiated from embryonic stem cells or induced pluripotent stem cells.

In another embodiment of this aspect and all other aspects provided herein, the cardiomyocytes and epicardial cells are present in admixture at a ratio of about 2:1.

In another embodiment of this aspect and all other aspects provided herein, wherein the method further comprises heat shocking the epicardial cells and the cardiomyocytes prior to transplantation.

In another embodiment of this aspect and all other aspects provided herein, the cardiomyocytes are heat shocked prior to being frozen for storage, and thawed to provide the preparation of cardiomyocytes used in the method.

In another embodiment of this aspect and all other aspects provided herein, the epicardial cells are heat shocked on the day before they are to be used to make a cardiomyocyte transplant composition.

BRIEF DESCRIPTION OF THE FIGURES

(FIG. 1A) Schematic of experimental design. Epicardial cells and cardiomyocytes were derived from hESC and co-cultured in 3D-EHT. (FIG. 1B) Epicardial cells derived from hESC expressing the epicardial markers BNC1 and WT1. (FIG. 1C) Purity of epicardial cells and cardiomyocytes by flow cytometry. (FIG. 1D) Schematic of 3D-EHT using hESC-derived epicardial cells and cardiomyocytes. (FIGS. 1E-1F) Compaction of 3D-EHT containing CM only, CM+hESC-MSC, CM+Primary MSC or CM+hESC-Epicardial cells. Scale bar: 2.5 mm. (FIGS. 1G, 1H) Ultrastructure and sarcomeric organization of 3D-EHT and quantification of sarcomeric length. Scale bar: 20 μm. Mean values; error bars represent SD. Two-sided p-values were calculated using a one-way ANOVA with post-hoc correction for multiple comparisons. *P<0.05 and ***P<0.001 in highlighted segments. Experiments were performed on at least three biological replicates on different days; n=9 constructs per experimental group.

(FIG. 2A) Active force generation of 3D-EHT containing CM only, CM+hESC-MSC, CM+Primary MSC or CM+hESC-epicardial cells. (FIG. 2B) Passive force generation of 3D-EHT containing CM only, CM+hESC-MSC, CM+Primary MSC or CM+hESC-epicardial cells. (FIG. 2C) Representative $Ca^{2+}$ traces of 3D-EHT. (FIG. 2D) Overlay of representative $Ca^{2+}$ curves. (FIG. 2E) Slope of $Ca^{2+}$-upstroke. Mean values; error bars represent SD. Dotted lines represent 95% confidence intervals. Two-sided p-values were calculated using a one-way ANOVA with post-hoc correction for multiple comparisons. *P<0.05 and ***P<0.001 in highlighted segments. Experiments were performed on at least three biological replicates on different days; n=9 constructs per experimental group.

(FIG. 3A) Schematic of study design. (FIG. 3B) Representative Picrosirius Red-Fast Green counterstained infarcted rat heart sections. (FIG. 3C) Quantification of myocardial infarct size. (FIG. 3D) Schematic of areas assessed for vascularization. (FIG. 3E) Microvascular density in cardiac grafts. (FIG. 3F) Microvascular density in the infarct zone. (FIG. 3G) Microvascular density in the non-injured border zone of the infarct. Mean values; error bars represent SD. Two-sided p-values were calculated using a one-way ANOVA with post-hoc correction for multiple comparisons unless otherwise stated. *P<0.05 and ***P<0.001 in highlighted segments. N=37 in total for histologic analysis at the 1-month time point. Control, EPI, CM, CM+EPI, n=9, 10, 8 and 9 animals. Scale bars: 50 μm.

(FIG. 4A) Sister sections of infarcted hearts demonstrating the cardiac grafts in animals that received either hESC-derived epicardial cells and cardiomyocytes or cardiomyocytes alone. Scale bar: 2.5 mm. (FIG. 4B) Quantification of cardiac graft size. (FIG. 4C) Cardiac grafts express the human specific marker (β-MHC and α-Actinin. Scale bar: c, 50 μm; c' and c", 20 μm. (FIG. 4D) Quantification of sarcomeric length. (FIG. 4E) Proliferative index of human cardiomyocytes in cardiac grafts. Scale bar: 20 μm. (FIG. 4F) Quantification of proliferative index. (FIG. 4G) Cardiac grafts and electrical integration with host tissue. Scale bars 50 μm for g and 20 μm for g'. Mean values; error bars represent SD. Two-sided p-values were calculated using an unpaired t-test unless otherwise stated. *P<0.05, P<0.01 and *P<0.001 in highlighted segments. N=37 in total for histologic analysis after 1 month; Control, EPI, CM, CM+EPI, n=9, 10, 9 and 9 animals. N=57 in total for functional analysis after 1 month; Control, EPI, CM, CM+EPI, n=14, 15, 14 and 14 animals.

(FIG. 5A) Echocardiographic effects of hESC-derived epicardial cell augmented cardiac grafts on post-infarct ventricular function. Fractional shortening values are given for the 96 hr baseline and 1-month follow-up. (FIG. 5B) Difference in fractional shortening. (FIG. 5C) Left-ventricular end-systolic dimension (LVESD) are given for the 96 hr baseline and 1-month follow-up. (FIG. 5D) Difference in LVEDS. (FIG. 5E) Left-ventricular end-diastolic dimension (LVEDD) are given for the 96 hr baseline and 1-month follow-up. (FIG. 5F) Difference in LVEDD. Mean values; error bars represent SD. Two-sided p-values were calculated using a paired t-test for comparison of cardiac function within groups between baseline and 1-month follow-up. If more than 2 groups were compared a one-way ANOVA with post-hoc correction for multiple comparisons was used. *P<0.05, P<0.01 and *P<0.001 in highlighted segments. N=57 in total for functional analysis after 1 month; Control, EPI, CM, CM+EPI, n=14, 15, 14 and 14 animals.

(FIG. 6A) Schematic for derivation of hESC-epicardium-derived cardiac fibroblasts. (FIG. 6B) Presence of epicardial (WT1) and epithelial markers (Pan-Cytokeratin) in hESC-derived epicardial cells but absence of the mesenchymal marker Vimentin. (FIG. 6C) Presence of the fibroblast (DDR2) and mesenchymal (Vimentin) markers but absence of epithelial marker expression (Pan-Cytokeratin) post differentiation to cardiac fibroblasts under chemically defined conditions. Scale bars: 50 μm.

(FIG. 7A) Epithelial and mesenchymal marker expression after 7 days and 14 days of construct development respectively. Scale bar 20 μm. (FIG. 7B) Quantification of EMT in 3D-EHT. (FIG. 7C) Electrical connectivity in 3D-EHT containing CM alone or CM+H9-MSC or CM+Primary-MSC or CM+EPI as demonstrated by CX43 expression. Scale bar 50 μm. Mean values; error bars represent SD. Two-sided p-values were calculated using an unpaired t-test for unpaired samples and using a paired t-test for paired samples. ***P<0.001 in highlighted segments. Experiments were performed on at least three biological replicates on different days; n=9 constructs per experimental group.

(FIG. 8A) Experimental setup and assessment of Frank-Starling mechanism in 3D-EHT. (FIG. 8B) Respective times of $Ca^{2+}$-upstroke. (FIG. 8C) Respective times for $Ca^{2+}$-downstroke. Mean values; error bars represent SD. Two-sided p-values were calculated using an unpaired t-test if two groups were compared and a one-way ANOVA with post-hoc correction was applied for multiple comparisons. *P<0.05, and ***P<0.001 in highlighted segments. Experiments were performed on at least three biological replicates on different days; n=9 constructs per experimental group.

FIGS. 9A-9F. HESC-derived epicardial cells engraft in the mammalian infarct and undergo EMT. (FIG. 9A) Schematic of experimental design for pilot trials. (FIG. 9B) Number of animals containing detectable grafts. (FIG. 9C) Engraftment of hESC-derived GFP-positive epicardial cells in the infarct zone. Animals received either a control injection of MG+PSC (n=4), $2\times10^6$ (n=4) or $4\times10^6$ (n=4) epicardial cells and were followed up for 7 days. (FIG. 9D) Long-term follow-up after epicardial cell transplantation. Animals either received a control injection of MG+PSC (n=4) or $6\times10^6$ (n=6) epicardial cells and were followed up for 1 month. (FIG. 9E) EMT of transplanted hESC-derived epicardial cells 7 days and 28 days post transplantation. (FIG. 9F) Quantification of EMT. Mean values; error bars represent SD. P-values were calculated using an unpaired t-test for unpaired samples and using a paired t-test for paired samples. *P<0.05 and ***P<0.001 in highlighted segments. Control, $2\times10^6$, $4\times10^6$; Control, $6\times10^6$, n=4, 4, 4; 4 and 6 animals.

FIGS. 10A-10G. Fate of grafted hESC-derived epicardial cells 4 weeks post transplantation. (FIG. 10A) Transplanted cells strongly express Vimentin and the fibroblast marker S100A4. (FIG. 10B) HESC-derived epicardial cells do not integrate in the wall of the coronary vasculature in the infarct zone (yellow arrowhead). (FIG. 10C) Rarely epicardial cells are found to express the smooth muscle cell marker SMA (white arrowheads) indicating a myofibroblast phenotype. (FIG. 10D) Transplanted cells are negative for human Lectin, using a paraffin embedded human fetal heart (FIG. 10E) as a positive control. (FIG. 10F) HESC-derived epicardial cells do not exhibit cardiomyocyte marker expression post transplantation, using non-infarcted rat myocardium (FIG. 10G) on the same section as a positive control. Scale bars: 20 μm.

(FIG. 11A) Mature vessels containing mural cells are detected in cardiac grafts containing epicardial cells but not in grafts containing cardiomyocytes only (yellow arrowheads). (FIG. 11B) Coronary arteries are present in the infarct zone of all study groups. (FIG. 11C) Coronary arteries are present in the non-injured border zone of all study groups. Scale bars: 20 μm.

FIGS. 12A-12F. Beneficial effects of hESC-derived epicardial cells are present on the long term. (FIG. 12A) Epicardial and cardiac grafts remain present on the long term. Scale bars: 20 μm. (FIG. 12B) Number of animals containing detectable grafts. (FIG. 12C) Quantification of infarct size 3 months after cell transplantation. (FIG. 12D) Schematic of BrdU injection schedule. (FIG. 12E) BrdU incorporation in animals at the 3-month time point. Scale bars: 20 μm. (FIG. 12F) Quantification of the proliferative index. Mean values; error bars represent SD. Two-sided p-values were calculated using a one-way ANOVA with post-hoc correction for multiple comparisons. *P<0.05, P<0.01 and *P<0.001 in highlighted segments. N=19 in total for histologic analysis after 3 months; Control, EPI, CM, CM+EPI, n=4, 5, 5 and 5 animals.

(FIG. 13A) Inter-observer agreement prior to functional analysis. Bland-Altman plots exhibiting the mean difference as well as the difference in FS (%) between the independent measurements of two blinded investigators. The dotted line shows the mean difference of all readouts and the continuous lines exhibit the a priori agreed limits of allowed deviation in measurements. Six animals each were analyzed at day −1, day 4 and day 28 respectively (n=18 in total). (FIG. 13B) Intraclass correlation coefficients (ICC) are shown for all measurements and the corresponding 95% CI in parenthesis. (FIGS. 13C-13D) Inter-observer agreement at the end of the analysis, demonstrated by Bland Altman plots and ICC.

(FIG. 14A) Paracrine co-culture assay using human ES-derived cardiomyocytes and epicardial cells in a Corning transwell plate. (FIG. 14B) Epicardial cells decrease the intrinsic beating rate of cardiomyocytes. (FIG. 14C) Epicardial cells promote the expression of cardiac marker genes. These data demonstrate that epicardial cells can be used in vitro in a paracrine assay to generate more mature hESC-derived cardiomyocytes.

(FIG. 15A) RNA sequencing reveals the secretome of epicardial cells and neural crest cells. Targets include Nephronectin (NPNT), Vitronectin (VTN) and Fibronectin (FNT). (FIG. 15B) Active force production in 3D-EHT using epicardial cells + cardiomyocytes compared to neural crest cells + cardiomyocytes. (FIG. 15C) Fibronectin expression in 3D-EHT. Expression is high in constructs containing epicardial cells but low in constructs containing human ES-derived mesenchymal cells and also primary mesenchymal cells. (FIG. 15D) Confirmation of Fibronectin expression in cardiac grafts in athymic rats in vivo after 4 weeks of follow up. These data indicate that Fibronectin (FNT) deposition by hESC-Epis may mediate some of the beneficial effects of epicardial cells.

FIG. 16A-16B. FIG. 16A shows longevity of human ES-derived epicardial and cardiac grafts and Fibronectin expression on the long-term. FIG. 16B shows grafts endured up to 3-months post grafting in vivo and epicardial cells continued to express Fibronectin.

DETAILED DESCRIPTION

Figure 1A:
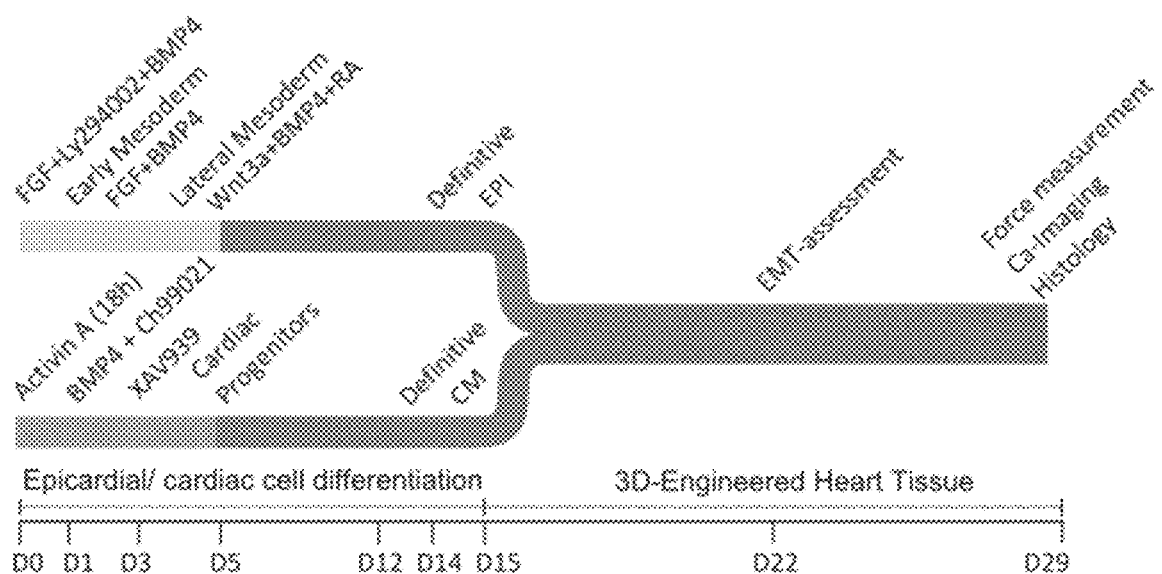
FIGS. 1A-1H. Generation and maturation of 3D-EHT using hESC-derived epicardial cells and cardiomyocytes.
Figure 1B:
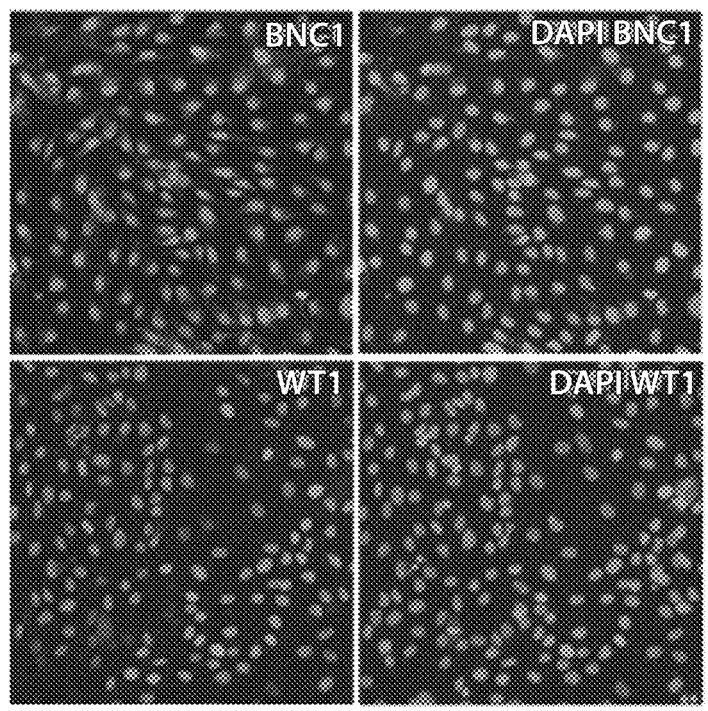
Figure 1C:
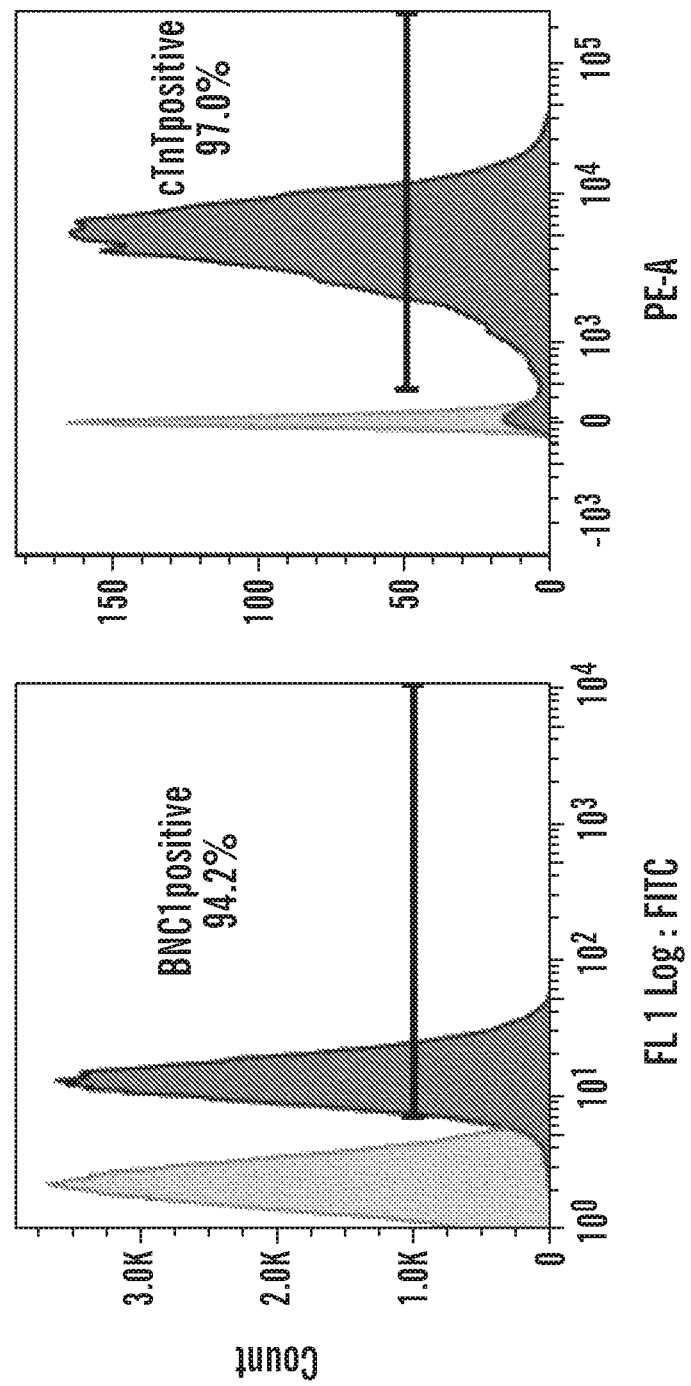
Figure 1D:
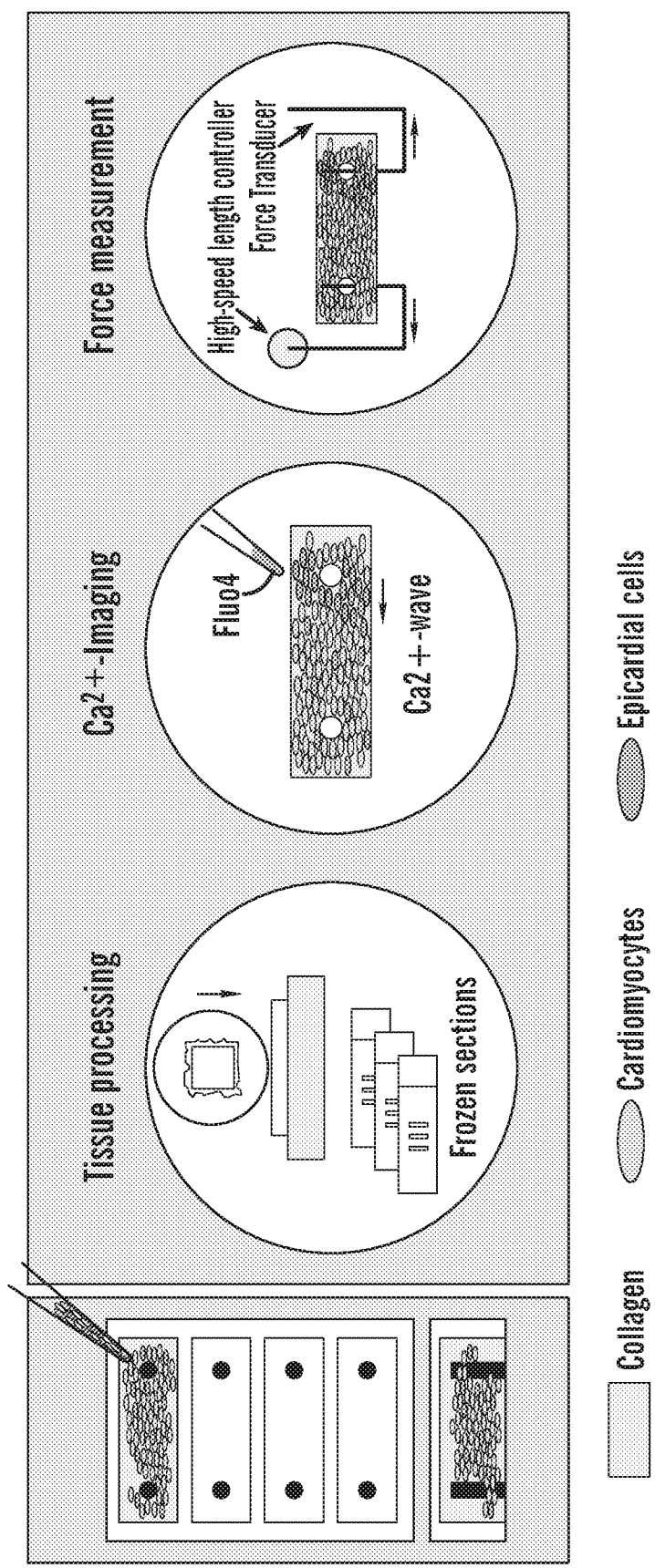

The compositions and methods described herein are related, in part, to the discovery that cardiomyocytes administered to a region of the myocardium engraft better in the presence of epicardial cells (e.g., in vitro-differentiated epicardial cells) as assessed by graft size, and cardiac functional measures, among other parameters. Indeed, while cardiomyocytes alone and epicardial cells alone can have beneficial effects when transplanted into damaged cardiac tissue, the combination of the two provides a synergistic effect on engraftment and a number of measures of cardiac graft function. Accordingly, also provided herein are compositions for the treatment of myocardial injury and/or the treatment or prevention of heart failure.

Definitions

As used herein the term "human stem cell" refers to a human cell that can self-renew and differentiate to at least one cell type. The term "human stem cell" encompasses human stem cell lines, human-derived iPS cells, human embryonic stem cells, human pluripotent cells, human multipotent stem cells, amniotic stem cells, placental stem cells, or human adult stem cells.

As used herein, the term "epicardial cells," in part, refers to epithelial cells of the epicardium, which typically serves as an outer protective layer of the heart and can provide factors for myocardial growth and maturation. Epicardial cells, as described herein, express WT1 and/or TCF21 and can further express one or more of the following markers: TBX18; BNC1; and cytokeratins. Additional functional epicardial cell criteria include, but are not limited to, formation of a polarized epithelial sheet and the ability to undergo epithelial-to-mesenchymal transition (EMT) (in vitro or in vivo) to generate fibroblasts (e.g., cardiac fibroblasts) and vascular smooth muscle lineages. An epicardial cell (or a population thereof) as the term is used herein can promote engraftment of cardiomyocytes when co-administered to cardiac tissue as described herein.

As used herein, the term "in vitro-differentiated epicardial cells" refers to epicardial cells that are generated in culture, typically via step-wise differentiation from a precursor cell such as a human embryonic stem cell, an induced pluripotent stem cell, an early mesoderm cell, a lateral plate mesoderm cell or a cardiac progenitor cell. While in vitro-differentiated epicardial cells can be differentiated from any of such precursor cells, the step-wise differentiation of human embryonic stem cells or iPS cells to epicardial cells exemplified herein occurs in the following order: hESC/hIPSC>early mesoderm>lateral plate mesoderm>epicardium. In addition, in vitro-differentiated epicardial cells need not go through every precursor cell type that an epicardial cell proceeds through in normal cardiac development. In one embodiment, the term "in vitro-differentiated epicardial cells" excludes adult human tissue-derived epicardial cells obtained from a subject (e.g., primary epicardial cells).

As used herein, the term "EMT" or "epithelial to mesenchymal transition" refers to the transition of a cell having an epithelial phenotype to a cell having a mesenchymal phenotype. An epithelial phenotype includes expression of epithelial cell markers (e.g., cadherin, cytokeratins, ZO-1, laminin, desmoplakin, MUC1 etc.) and a high degree of intercellular interactions through adherens junctions. A mesenchymal phenotype includes expression of mesenchymal markers (e.g., vimentin, fibronectin, twist, FSP-1 Snai1, Snai2), an amoebic morphology, loss of intercellular junctions, and increased cell mobility. In the adult heart, EMT typically occurs in response to an injury to the myocardium. While epithelial cells tend to have many intercellular interactions with other epithelial cells, mesenchymal cells are mobile and developmentally pliable, which is particularly useful in repairing injured myocardial tissue.

As used herein, the term "differentiated progeny of epicardial cells" refers to any of the cells developmentally downstream of, or differentiated from, epicardial cells, particularly epicardial cells that have undergone EMT to produce epicardium derived cells (EPDCs). Further non-limiting examples of differentiated progeny include vascular smooth muscle cells, cardiac fibroblasts, interstitial fibroblasts, mesenchymal-like cells (e.g., cardiac colony forming units—fibroblasts (cCFU-F)) and possibly endothelial cells, cardiomyocytes or cardiac progenitor cells). Accordingly, the "differentiated progeny of epicardial cells" refers to any of the differentiated cells that are downstream from any of the epicardial cells, as that term is used herein, and in particular includes e.g., vascular smooth muscle cells, cardiac fibroblasts, interstitial fibroblasts, endothelial cells, pericytes and cardiomyocytes. It is specifically contemplated herein that cells derived from epicardial cells can be used for providing effects similar or equivalent to those provided by epicardial cells on cardiomyocyte engraftment, proliferation and function when introduced to cardiac tissue in admixture with cardiomyocytes in vivo.

As used herein, the term "positive for" when referring to a cell positive for a marker (e.g., Wilm's tumor 1 (WT1) positive epicardial cells) means that a cell surface marker (e.g., WT1) is detectable above background levels on the cell using immunofluorescence microscopy or flow cytometry methods, such as fluorescence activated cell sorting (FACS). Alternatively, the terms "positive for" or "expresses a marker" means that expression of mRNA encoding a cell surface or intracellular marker (including, but not limited to a given transcription factor) is detectable above background levels using RT-PCR. The expression level of a cell surface marker or intracellular marker can be compared to the expression level obtained from a negative control (i.e., cells known to lack the marker) or by isotype controls (i.e., a control antibody that has no relevant specificity and only binds non-specifically to cell proteins, lipids or carbohydrates). Thus, a cell that "expresses" a marker (or is "positive for a marker") has an expression level detectable above the expression level determined for the negative control for that marker. For example, in some embodiments an epicardial cell as that term is used herein it positive for WT1, and/or TCF21 and further can be positive for one or more markers including, but not limited to, TBX18, cytokeratins, twist, or snail.

As used herein, the term "negative for" when referring to a cell negative for a marker (or the term "does not express") means that a cell surface marker cannot be detected above background levels on the cell using immunofluorescence microscopy or flow cytometry methods, such as fluorescence activated cell sorting (FACS). Alternatively, the terms "negative" or "does not express" means that expression of the mRNA for an intracellular marker or cell surface marker cannot be detected above background levels using RT-PCR. The expression level of a cell surface marker or intracellular marker can be compared to the expression level obtained from a negative control (i.e., cells known to lack the marker) or by isotype controls (i.e., a control antibody that has no relevant specificity and only binds non-specifically to cell proteins, lipids or carbohydrates). Thus, a cell that "does not express" a marker appears similar to the negative control with respect to that marker. For example, in some embodiments, an epicardial cell as described herein is negative for mesenchymal stem cell markers.

The term "marker" as used herein is used to describe a characteristic and/or phenotype of a cell. Markers can be used for selection of cells comprising characteristics of interest and can vary with specific cells. Markers are characteristics, whether morphological, structural, functional or biochemical (enzymatic) characteristics of the cell of a particular cell type, or molecules expressed by the cell type. In one aspect, such markers are proteins. Such proteins can possess an epitope for antibodies or other binding molecules available in the art. However, a marker can consist of any molecule found in or on a cell, including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method available to one of skill in the art. Markers can also be the absence of a morphological characteristic or absence of proteins, lipids etc. Markers can be a combination of a panel of unique characteristics of the presence and/or absence of polypeptides and other morphological or structural characteristics. In one embodiment, the marker is a cell surface marker.

In some embodiments, the absence of a cell surface marker can be used to distinguish e.g., an epicardial cell from a cell of another lineage (e.g., a hematopoietic cell or "blood-forming" cell). Exemplary cell surface markers that are absent on cardiogenic mesoderm cells and permit identification/selection from hemogenic mesoderm cells include, but are not limited to, KDR/CD34, SCL/TAL1, GATA1, RUNX1, HAND1, CDX1, WNT8a and WNT3a. Conversely, exemplary cell surface markers on hemogenic mesoderm cells that can be used to remove hemogenic mesoderm cells include, but are not limited to, KDR/CD34, SCL/TAL1, GATA1, RUNX1, HAND1, CDX1, WNT8a and WNT3a. One of skill in the art will recognize that a cell surface marker can be present at a particular point in development or in a particular cardiac progenitor cell type but can be lost as the cell is differentiated further down a committed lineage of cells. For example, KDR is expressed in cardiogenic mesoderm cells, but is lost upon differentiation to a cardiac progenitor cell. Thus, a cell surface marker can be used in combination with a positive selection strategy for epicardial cells and also used in combination with a negative selection strategy for other cells (e.g., hematopoietic cells).

In the context of cell ontogeny, the term "differentiate", or "differentiating" is a relative term that indicates a "differentiated cell" is a cell that has progressed further down the developmental pathway than its precursor cell. Thus in some embodiments, a stem cell as the term is defined herein, can differentiate to lineage-restricted precursor cells (such as a human cardiac progenitor cell or mid-primitive streak cardiogenic mesoderm progenitor cell), which in turn can differentiate into other types of precursor cells further down the pathway (such as a tissue specific precursor, such as a cardiomyocyte precursor), and then to an end-stage differentiated cell, which plays a characteristic role in a certain tissue type, and may or may not retain the capacity to proliferate further. Methods for in vitro differentiation of stem cells to cardiomyocytes and/or to epicardial cells are known in the art and/or described herein below.

As used herein, the terms "dedifferentiation" or "reprogramming" or "retrodifferentiation" refer to the process that generates a cell that re-expresses a more stem cell phenotype or a less differentiated phenotype than the cell from which it is derived. For example, a multipotent cell can be dedifferentiated to a pluripotent cell. That is, dedifferentiation shifts a cell backward along the differentiation spectrum of totipotent cells to fully differentiated cells. Typically, reversal of the differentiation phenotype of a cell requires artificial manipulation of the cell, for example, by expressing stem cell-specific mRNA and/or proteins. Reprogramming is not typically observed under native conditions in vivo or in vitro.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cells forming the body of an organism, as opposed to germline cells. Every cell type in the mammalian body—apart from the sperm and ova, the cells from which they are made (gametocytes) and undifferentiated stem cells—is a somatic cell: internal organs, skin, bones, blood, and connective tissue are all substantially made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated, the methods for reprogramming a differentiated cell (e.g., to generate an iPSC) can be performed both in vivo and in vitro (where in vivo is practiced when a differentiated cell is present within a subject, and where in vitro is practiced using an isolated differentiated cell maintained in culture).

The term "isolated cell" as used herein refers to a cell that has been removed from an organism in which it was originally found, or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "substantially pure," with respect to a particular cell population, refers to a population of cells that is at least about 75%, preferably at least about 85%, more preferably at least about 90%, and most preferably at least about 95% pure, with respect to the cells making up a total cell population. That is, the terms "substantially pure" or "essentially purified," with regard to a population of cardiomyocytes and/or epicardial cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not cardiomyocytes or epicardial cells, respectively.

The terms "enriching" or "enriched" are used interchangeably herein and mean that the yield (fraction) of cells of one type, such as human epicardial cell compositions and cells for use in the methods described herein, is increased by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, or by at least 75%, over the fraction of cells of that type in a starting biological sample, culture, or preparation.

The term "separation" or "selection" as used herein refers to isolating different cell types into one or more populations and collecting the isolated population as a target cell population which is enriched, for example, in a specific target cell. Selection can be performed using positive selection, whereby a target enriched cell population is retained, or negative selection, whereby non-target cell types are discarded (thereby enriching for desired target cell types in the remaining cell population).

The term "positive selection" as used herein refers to selection of a desired cell type by retaining the cells of interest. In some embodiments, positive selection involves the use of an agent to assist in retaining the cells of interest, e.g., use of a positive selection agent such as an antibody which has specific binding affinity for a surface antigen on the desired or target cell. In some embodiments, positive selection can occur in the absence of a positive selection agent, e.g., in a "touch-free" or closed system, for example, where positive selection of a target cell type is based on any of cell size, density and/or morphology of the target cell type.

The term "negative selection" as used herein refers to selection of undesired or non-target cells for depletion or discarding, thereby retaining (and thus enriching) the desired target cell type. In some embodiments, negative selection involves the use of an agent to assist in selecting undesirable cells for discarding, e.g., use of a negative selection agent such as a monoclonal antibody which has specific binding affinity for a surface antigen on unwanted or non-target cells. In some embodiments, negative selection does not involve a negative selection agent. In some embodiments, negative selection can occur in the absence of a negative selection agent, e.g., in a "touch-free" or closed system, for example, where negative selection of an undesired (non-target) cell type to be discarded is based on any of cell size, density and/or morphology of the undesired (non-target) cell type.

As used herein, the term "physical association" refers to cell-to-cell contact achieved by proximity of epicardial cells and cardiomyocytes in a composition as described herein. The cell-to-cell contact does not require that the cells comprise direct intercellular communication through e.g., gap junctions, adherens junctions etc., but rather refers to the cells being attached, either directly, or via common attachment to, e.g., a matrix or scaffold. A first cell is "physically associated with" a second cell as the term is used herein if, for example, specific capture of the first cell, e.g., by binding a marker expressed on the first cell, but not on the second cell, results in co-isolation of the first and second cells. In one embodiment, the term 'physical association' refers to epicardial cells and cardiomyocytes in a composition where factors, such as fibronectin, secreted by one cell (e.g., epicardial cell) can affect the function or viability of the second cell (e.g., cardiomyocyte).

As used herein, a "tissue particle" refers to an in vitro cultured cell composition comprising at least two different cell types in physical association with each other. In one embodiment, the cells in a tissue particle include cardiomyocytes and epicardial cells. In one embodiment, the only cells in the tissue particle are cardiomyocytes and epicardial cells. In one embodiment, the cells in a tissue particle are in vitro-differentiated cardiomyocytes and epicardial cells. A tissue particle can, but need not necessarily contain a scaffold as the term is used herein. A tissue particle will include at least two cells, i.e., at least one each of two different cell types, but can include, for example, from 2-2500 cells, e.g., at least 2 cells, at least 4 cells, at least 5 cells, at least 10 cells, at least 20 cells, at least 30 cells, at least 40 cells, at least 50 cells, at least 100 cells, at least 200 cells, at least 300 cells, at least 400 cells, at least 500 cells, at least 600 cells, at least 700 cells, at least 800 cells, at least 900 cells, at least 1000 cells, at least 1100 cells, at least 1200 cells, at least 1300 cells, at least 1400 cells, at least 1500 cells, at least 1600 cells, at least 1700 cells, at least 1800 cells, at least 1900 cells, at least 2000 cells, at least 2100 cells, at least 2200 cells, at least 2300 cells, at least 2400 cells or about 2500 cells. In one embodiment, a tissue particle includes 2500 or fewer cells, e.g., 2400 or fewer cells, 2300 or fewer cells, 2200 or fewer cells, 2100 or fewer cells, 2000 or fewer cells, 1900 or fewer cells, 1800 or fewer cells, 1700 or fewer cells, 1600 or fewer cells, 1500 or fewer cells, 1400 or fewer cells, 1300 or fewer cells, 1200 or fewer cells, 1100 or fewer cells, 1000 or fewer cells, 900 or fewer cells, 800 or fewer cells, 700 or fewer cells, 600 or fewer cells, 500 or fewer cells, 400 or fewer cells, 300 or fewer cells, 200 or fewer cells, 100 or fewer cells, 50 or fewer cells, but at least two cells. In various embodiments, a tissue particle can include, for example, 2-100 cells, 2-500 cells, 2-1000 cells, 2-1500 cells, 2-2000 cells, 2-2400 cells, 100-200 cells, 100-500 cells, 100-1000 cells, 100-1500 cells, 100-2000 cells, 100-2500 cells, 200-400 cells, 200-500 cells, 200-1000 cells, 200-1500 cells, 200-2000 cells, 200-2500 cells, 500-1000 cells, 500-1500 cells, 500-2000 cells, or 500-2500 cells. When cell numbers permit, cells in a tissue particle can be present in a ratio varying from 1:1, 1:2, 1:3, 1:4, 1:5, 1:10; 1:15, 1:20, 1:25, 1:50, 1:75 or even 1:100.

As used herein, the term "mature phenotype" when applied to cardiomyocytes refers to the phenotype of a cell that comprises a phenotype similar to adult cardiomyocytes and does not comprise at least one feature of a fetal cardiomyocyte. In some embodiments, markers which indicate increased maturity of a cardiomyocyte include, but are not limited to, an increased expression of α-actinin, c-TnT and/or b-MHC, increased anisotropy, increased cellular alignment, anisotropic arrangement of gap junctions & cadherins between cells, increased T-tubule formation and caveolin expression, wherein the increase is relative to that marker in another population of the same cardiomyocytes, e.g., in relation to a population of cardiomyocytes in the absence of co-administered epicardial cells. In some embodiments, the matured cardiomyocytes have an increased conversion of ssTnI to ctTnI, N2BA to N2B, and appropriate increase or decrease in expression of ion channels as expressed in adult cardiac tissue (voltage gated K+ channels, Na+ channels, voltage dependent Ca2+ channels, cyclic nucleotide dependent K+ channels, and other ion channels). In some embodiments, the matured cardiomyocytes have an increased contraction at single cell and multicellular level measured by contraction mapping aided by microscopy, increased strength of contraction. In some embodiments, the matured cardiomyocytes have an increased cell-cell electrical conductivity, increased syncytial nature of 2D in vitro culture in large area (cm2) allowing electrical action potential to propagate from one point to another, increased wave speed and decreased excitation threshold, increased Ca2+ transient current.

As used herein, the term "microvascular density" refers to the concentration of small blood vessels within an engrafted region of the heart. In one embodiment, the microvascular density is a measurement of new blood vessels/vasculature (e.g., angiogenesis) in a region of the heart, in particular an infarcted region or a region including grafted cardiomyocytes.

As used herein, the term "electrical connection" when referring to cardiomyocytes refers to cell-to-cell connections that permit movement of intracellular ions and other small molecules from one cell to the other (e.g., gap junctions formed by connexin 43), which in turn permits the propagation of electrical signals between the cells (e.g., propagation of an action potential). The extent of electrical connections between adjacent cardiomyocytes is also referred to herein as "electrical connectivity" or "electroconnectivity."

As used herein, the term "increasing the proliferation of transplanted cardiomyocytes," refers to an increase in the number of cardiomyocytes that occurs when epicardial cells are included in a transplant composition, as compared to the increase in the number of cardiomyocytes when they are not transplanted with epicardial cells.

As used herein, the term "scaffold" refers to a structure, comprising a biocompatible material that provides a surface suitable for adherence and proliferation of cells. A scaffold can further provide mechanical stability and support. A scaffold can be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used herein, the term "implantable in a subject" refers to any non-living (e.g., acellular) implantable structure that upon implantation does not generate an appreciable immune response in the host organism. Thus, an implantable structure should not for example, be or contain an irritant, or contain LPS etc.

As used herein, the term "biodegradable" refers to the ability of a scaffold to degrade under physiological conditions, for example, under conditions that do not adversely affect cell viability of the delivered cells or cells in vivo. Such biodegradable scaffolds will preferably not be or contain an irritant or an allergen that can cause a systemic reaction in the subject to which the composition has been implanted. In some embodiments, biodegradable means that the scaffold can be metabolized and the metabolites cleared from the subject by physiological excretion mechanisms (e.g., urine, feces, liver detoxification etc.).

As used herein, the term "treating" includes reducing or alleviating at least one adverse effect or symptom of a condition, disease or disorder. For example, the term "treating" and "treatment" refers to administering to a subject an effective amount of a composition, e.g., an effective amount of a composition comprising a population of e.g., epicardial cells, cardiomyocytes etc. so that the subject has a reduction in at least one symptom of the disease or an improvement in the disease, for example, beneficial or desired clinical results (e.g., improved cardiac function in an infarcted area of the heart, improved engraftment of cardiomyocytes etc.). For purposes of this disclosure, beneficial or desired clinical results include, but are not limited to, alleviation of one or more symptoms, diminishment of extent of disease, disease stabilization (e.g., not worsening), delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition, but may not be a complete cure for the disease. In some embodiments, treatment can include prophylaxis. However, in alternative embodiments, treatment does not include prophylaxis.

"Treatment" of a cardiac disorder, a cardiac disease, or a cardiac injury (e.g., myocardial infarction) as referred to herein refers to therapeutic intervention that enhances cardiac function and/or enhances cardiomyocyte engraftment and/or enhances cardiomyocyte transplant or graft vascularization in a treated area, thus improving the function of e.g., the heart. That is, cardiac "treatment" is oriented to the function of the heart (e.g., enhanced function within an infarcted area), and/or other site treated with the compositions described herein. A therapeutic approach that improves the function of the heart, for example as assessed by measuring left-ventricular end-systolic dimension (LVESD)) by at least 10%, and preferably by at least 20%, 30%, 40%, 50%, 75%, 90%, 100% or more, e.g., 2-fold, 5-fold, 10-fold or more, up to and including full function, relative to such function prior to such therapy is considered effective treatment. Effective treatment need not cure or directly impact the underlying cause of the heart disease or disorder to be considered effective treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "prevention" or "preventing," when used in reference to a disease, disorder or symptoms thereof, refers to a reduction in the likelihood that an individual will develop a disease or disorder, e.g., heart failure following myocardial infarction, as but one example. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 10% on a clinically accepted scale for that disease or disorder) or delayed (e.g., by days, weeks, months or years) symptoms is considered effective prevention.

As used herein, the term "induced to differentiate" refers to a chemical/biological treatment, a physical environment or a genetic modification that is conducive to the formation of more differentiated cells (e.g., epicardial cells) from pluripotent or multipotent stem cells. Differentiation can be assessed by the appearance of distinct cell-type specific markers or by the loss of stem cell specific markers, or both.

The terms "decrease", "reduced", "reduction", or "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level.

The terms "increased", "increase" or "enhance" or "activate" are all used herein to generally mean an increase of a property, level, or other parameter by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Cell Preparations

The methods and compositions described herein can use cardiomyocytes and epicardial cells differentiated in vitro, e.g., from embryonic stem cells, pluripotent stem cells, such as induced pluripotent stem cells, or other stem cells that permit such differentiation. The following describes various stem cells that can be used to prepare cardiomyocytes and epicardial cells.

Embryonic Stem Cells: Stem cells are cells that retain the ability to renew themselves through mitotic cell division and can differentiate into more specialized cell types. Three broad types of mammalian stem cells include: embryonic stem (ES) cells that are found in blastocysts, induced pluripotent stem cells (iPSCs) that are reprogrammed from somatic cells, and adult stem cells that are found in adult tissues. Other sources of pluripotent stem cells can include amnion-derived or placental-derived stem cells. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues. Pluripotent stem cells can differentiate into cells derived from any of the three germ layers.

Cardiomyocytes and epicardial cells useful in the methods and compositions described herein can be differentiated from both embryonic stem cells and induced pluripotent stem cells, among others. In one embodiment, the compositions and methods provided herein use human cardiomyocytes and/or epicardial cells differentiated from embryonic stem cells. Alternatively, in some embodiments, the compositions and methods provided herein do not encompass generation or use of human cardiogenic cells and/or epicardial cells made from cells taken from a viable human embryo.

Embryonic stem cells and methods for their retrieval are well known in the art and are described, for example, in Trounson A O (Reprod Fertil Dev (2001) 13: 523), Roach M L (Methods Mol Biol (2002) 185: 1), and Smith A G (Annu Rev Cell Dev Biol (2001) 17:435). The term "embryonic stem cell" is used to refer to the pluripotent stem cells of the inner cell mass of the embryonic blastocyst (see e.g., U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235,970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

Cells derived from embryonic sources can include embryonic stem cells or stem cell lines obtained from a stem cell bank or other recognized depository institution. Other means of producing stem cell lines include methods comprising the use of a blastomere cell from an early stage embryo prior to formation of the blastocyst (at around the 8-cell stage). Such techniques correspond to the pre-implantation genetic diagnosis technique routinely practiced in assisted reproduction clinics. The single blastomere cell is co-cultured with established ES-cell lines and then separated from them to form fully competent ES cell lines.

Embryonic stem cells are considered to be undifferentiated when they have not committed to a specific differentiation lineage. Such cells display morphological characteristics that distinguish them from differentiated cells of embryo or adult origin. Undifferentiated embryonic stem (ES) cells are easily recognized by those skilled in the art, and typically appear in the two dimensions of a microscopic view in colonies of cells with high nuclear/cytoplasmic ratios and prominent nucleoli. In some embodiments, the human cardiomyocytes and/or epicardial cells described herein are not derived from embryonic stem cells or any other cells of embryonic origin.

Adult stem cells are stem cells derived from tissues of a post-natal or post-neonatal organism or from an adult organism. An adult stem cell is structurally distinct from an embryonic stem cell not only in markers it does or does not express relative to an embryonic stem cell, but also by the presence of epigenetic differences, e.g. differences in DNA methylation patterns.

Induced Pluripotent Stem Cells (iPSCs)

In some embodiments, the methods and compositions described herein utilize cardiomyocytes and/or epicardial cells that are differentiated in vitro from induced pluripotent stem cells. An advantage of using iPSCs to generate cardiomyocyte and/or epicardial cells for the compositions described herein is that the cells can be derived from the same subject to which the desired human cardiomyocytes and/or epicardial cells are to be administered. That is, a somatic cell can be obtained from a subject, reprogrammed to an induced pluripotent stem cell, and then re-differentiated into a human cardiomyocyte and/or an epicardial cell to be administered to the subject (e.g., autologous cells). Since the cardiomyocytes and/or epicardial cells (or their differentiated progeny) are essentially derived from an autologous source, the risk of engraftment rejection or allergic responses is reduced compared to the use of cells from another subject or group of subjects. In some embodiments, the cardiomyocytes and/or epicardial cells useful for the compositions described herein are derived from non-autologous sources. In addition, the use of iPSCs negates the need for cells obtained from an embryonic source. Thus, in one embodiment, the stem cells used to generate epicardial cells or cardiomyocytes for use in the compositions and methods described herein are not embryonic stem cells.

Although differentiation is generally irreversible under physiological contexts, several methods have been developed in recent years to reprogram somatic cells to induced pluripotent stem cells. Exemplary methods are known to those of skill in the art and are described briefly herein below.

Reprogramming is a process that alters or reverses the differentiation state of a differentiated cell (e.g., a somatic cell). Stated another way, reprogramming is a process of driving the differentiation of a cell backwards to a more undifferentiated or more primitive type of cell. It should be noted that placing many primary cells in culture can lead to some loss of fully differentiated characteristics. However, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character when differentiated cells are placed in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state with the capacity for self-renewal and differentiation to cells of all three germ cell lineages. The resulting cells are referred to as "reprogrammed cells," or "induced pluripotent stem cells (iPSCs or iPS cells)."

The specific approach or method used to generate pluripotent stem cells from somatic cells (e.g., any cell of the body with the exclusion of a germ line cell; fibroblasts etc.) is not critical to the claimed invention. Thus, any method that re-programs a somatic cell to the pluripotent phenotype would be appropriate for use in the methods described herein.

iPS cells can be generated or derived from terminally differentiated somatic cells, as well as from adult stem cells, or somatic stem cells. That is, a non-pluripotent progenitor cell can be rendered pluripotent or multipotent by reprogramming.

The efficiency of reprogramming (i.e., the number of reprogrammed cells) derived from a population of starting cells can be enhanced by the addition of various small molecules as shown by Shi, Y., et al (2008) *Cell-Stem Cell* 2:525-528, Huangfu, D., et al (2008) *Nature Biotechnology* 26(7):795-797, and Marson, A., et al (2008) Cell-Stem Cell 3:132-135. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

When reprogrammed cells are used for generation of human cardiomyocytes and/or epicardial cells to be used in the therapeutic treatment of disease, it is desirable, but not required, to use somatic cells isolated from the patient being treated. For example, somatic cells involved in diseases, and somatic cells participating in therapeutic treatment of diseases and the like can be used. In some embodiments, a method for selecting the reprogrammed cells from a heterogeneous population comprising reprogrammed cells and somatic cells from which they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; β-III-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; β-catenin, and Bmi1. Such cells can also be characterized by the down-regulation of markers characteristic of the somatic cell from which the induced pluripotent stem cell is derived.

In Vitro Differentiation

The methods and compositions described herein can use in vitro differentiated cardiomyocytes and epicardial cells. Methods for the differentiation of either cell type from ESCs or IPSCs are known in the art. See, e.g., LaFlamme et al., *Nature Biotech* 25:1015-1024 (2007), which describes the differentiation of cardiomyocytes and Witty et al., *Nature Biotech.* 32:1026-1035 (2014) and Iyer et al., *Development* 142:1528-1541 (2015), which describe the differentiation of epicardial cells. These approaches use various factors and conditions to activate and guide differentiation programs leading to their respective cell types. Pathways and certain of the factors involved in them are discussed in the following.

Typically, the step-wise differentiation of ESCs or IPSCs epicardial cells begins with an embryonic stem cell or induced pluripotent stem cell, which is differentiated into an early mesoderm cell, then through a lateral mesoderm cell phenotype to an epicardial cell.

In certain embodiments, the step-wise differentiation of ESCs or iPSCs to cardiomyocytes proceeds in the following order: ESC or iPSC>cardiogenic mesoderm>cardiac progenitor cells>cardiomyocytes (see e.g., US 2017024086, the contents of which are incorporated herein by reference in its entirety).

As will be appreciated by those of skill in the art, in vitro-differentiation of epicardial cells and/or cardiomyocytes produces an end-result of a cell having the phenotypic and morphological features of an epicardial cell or cardiomyocyte but that the differentiation steps of in vitro-differentiation need not be the same as the differentiation that occurs naturally in the embryo. That is, during differentiation to an epicardial cell or cardiomyocyte, it is specifically contemplated herein that the step-wise differentiation approach utilized to produce such cells need not proceed through every progenitor cell type that has been identified during embryogenesis and can essentially "skip" over certain stages of development that occur during embryogenesis.

TGF-β signaling pathway modulation: In some embodiments, one or more TGF-β agonists (e.g., Activin A) are used to promote a particular differentiation step of a pluripotent cell to an epicardial cell or in some instances, a cardiomyocyte. With respect to epicardial cells, TGF-β signaling can also promote epithelial-to-mesenchymal cell transition of epicardial cells. In such embodiments, an activating agent specific for TGF-β signaling can be a TGF-β polypeptide or an active fragment thereof, a fusion protein comprising a TGF-β polypeptide or an active fragment thereof, an agonist antibody to a TGF-β receptor, or a small molecule agonist of a TGF-β receptor.

In some embodiments, the dose of TGF-β agonist (e.g., Activin A) used in the methods described herein, for example, in differentiating cardiomyocytes from human embryonic stem cells or iPS cells, is between 50 ng/mL and 100 ng/mL, between 75 ng/mL and 125 ng/mL, between 50 and 200 ng/mL, between 50 and 500 ng/mL, between 100 ng/mL and 1000 ng/mL, between 100 ng/mL and 750 ng/mL, between 100 ng/mL and 500 ng/mL, between 100 ng/mL and 400 ng/mL, between 100 ng/mL and 300 ng/mL, between 100 ng/mL and 200 ng/mL, between 90 ng/mL and 150 ng/mL, or between 80 ng/mL and 120 ng/mL.

In some embodiments, the dose of TGF-β agonist (e.g., Activin A) is e.g., at least 25 ng/mL, at least 50 ng/mL, at least 75 ng/mL, at least 80 ng/mL, at least 85 ng/mL, at least 90 ng/mL, at least 95 ng/mL, at least 99 ng/mL, at least 100 ng/mL, at least 105 ng/mL, at least 110 ng/mL, at least 120 ng/mL, at least 150 ng/mL or more.

BMP receptor pathway activation: In some embodiments, a BMP agonist is used in the differentiation of epicardial cells and/or cardiomyocytes for use in the compositions and methods described herein. In certain embodiments, BMP4 is used in a differentiation step of (i) human pluripotent stem cells to early mesoderm cells, (ii) early mesoderm cells to lateral plate mesoderm cells, and/or (iii) lateral plate mesoderm cells to epicardial cells.

In one embodiment, one or more BMP agonists are used to promote a particular differentiation step of a pluripotent cell. In such embodiments, an activating agent specific for BMP signaling can be a BMP polypeptide or an active fragment thereof, a fusion protein comprising a BMP polypeptide or an active fragment thereof, an agonist antibody to a BMP receptor, or a small molecule agonist of a BMP receptor. In one embodiment, the BMP used with the methods described herein is BMP4.

In some embodiments, the dose of BMP4 is e.g., at least 5 ng/mL, at least 10 ng/mL, at least 25 ng/mL, at least 30 ng/mL, at least 40 ng/mL, at least 50 ng/mL, at least 60 ng/mL, at least 70 ng/mL, at least 75 ng/mL, at least 80 ng/mL, at least 85 ng/mL, at least 90 ng/mL, at least 95 ng/mL, at least 99 ng/mL, at least 100 ng/mL, at least 105 ng/mL, at least 110 ng/mL, at least 120 ng/mL, at least 150 ng/mL, at least 175 ng/mL, at least 200 ng/mL, at least 225 ng/mL or more.

In certain embodiments, the dose of BMP4 is within the range of 5-200 ng/mL, 5-150 ng/mL, 5-100 ng/mL, 5-75 ng/mL, 5-50 ng/mL, 5-15 ng/mL, 25-50 ng/mL, 25-75 ng/mL, 25-100 ng/mL, 40-60 ng/mL, 45-55 ng/mL, 50-100 ng/mL, 50-150 ng/mL, 50-200 ng/mL, 150-200 ng/mL, 100-200 ng/mL, 75-200 ng/mL, or any range therebetween.

FGF activation: In some embodiments, FGF2 is used in a differentiation step to induce (i) differentiation of human pluripotent stem cells (e.g., hESC or hIPSCs) to early mesoderm cells, or (ii) differentiation of early mesoderm cells to lateral plate mesoderm cells. These cells can then be further differentiated to produce cardiomyocytes and/or epicardial cells useful in the methods and compositions described herein, for example, for the treatment or prevention of heart failure.

In some embodiments, the dosage range useful for FGF2 is between 1 and 30 ng/mL, for example between 1 and 25 ng/mL, between 1 and 20 ng/mL, between 1 and 15 ng/mL, between 1 and 10 ng/mL, between 1 and 5 ng/mL, between 1.5 and 30 ng/mL, between 2 and 30 ng/mL, between 5 and 30 ng/mL, between 10 and 30 ng/mL, between 15 and 25 ng/mL, between 15 and 30 ng/mL, between 20 and 30 ng/mL, between 25 and 30 ng/mL, between 8 and 12 ng/mL, between 9 and 15 g/mL, between 9 and 11 ng/mL, between 8 and 20 ng/mL or any range therebetween.

In some embodiments the dose of FGF2 is e.g., at least 1 ng/mL, at least 2 ng/mL, at least 3 ng/mL, at least 4 ng/mL, at least 5 ng/mL, at least 6 ng/mL, at least 7 ng/mL, at least 8 ng/mL, at least 9 ng/mL, at least 10 ng/mL, at least 12 ng/mL, at least 14 ng/mL, at least 15 ng/mL, at least 16 ng/mL, at least 18 ng/mL, at least 20 ng/mL, at least 22 ng/mL, at least 24 ng/mL, at least 25 ng/mL or more.

Wnt Antagonists: Provided herein are methods for directing mesoderm cells into the cardiac lineage by contacting a cell with a Wnt antagonist. Some non-limiting examples of Wnt antagonists include Wnt pathway inhibitor V (also known as (E)-4-(2,6-Difluorostyryl)-N,N-dimethylaniline), IWR-1 endo, IWP-2, CCT036477, XAV-939 (tankyrase inhibitor), and a peptide comprising the sequence t-Boc-NH-Met-Asp-Gly-Cys-Glu-Leu-CO2H.

In some embodiments, the dosage range useful for a Wnt antagonist (e.g. XAV-939) is between 0.5 and 5 µM, between 0.5 and 4 µM, between 0.5 and 3 µM, between 0.5 and 2 µM, between 0.5 and 1 µM, between 4 and 5 µM, between 3 and 5 µM, between 2 and 5 µM, between 1 and M, between 0.5 and 2 µM, between 0.75 and 2 µM, between 0.9 µM and 2 M, or any range therebetween.

In some embodiments the dose of a Wnt antagonist is e.g., at least 20 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 110 ng/mL, at least 120 ng/mL, at least 130 ng/mL, at least 140 ng/mL, at least 150 ng/mL, at least 160 ng/mL, at least 170 ng/mL, at least 180 ng/mL, at least 190 ng/mL, at least 200 ng/mL, or more.

Wnt Agonists: In some embodiments, epicardial cells useful in the methods and compositions described herein can be generated using a protocol comprising, in part, treating a lateral plate mesoderm cell with a Wnt agonist (e.g., Wnt3A). Wnt agonists can include Wnt peptides, small molecules, peptidomimetics etc. In certain embodiments, the Wnt agonist is 2-amino-4-[3,4-(methylenedioxy)benzyl-amino]-6-(3-methoxyphenyl)pyrimidine, WAY-316606, (hetero) arylpyrimidines, IQ1, QS11, SB-216763, or dichloroacetate (DCA). Wnt agonists can also be obtained commercially from sources, such as Sigma-Aldrich, ApexBio, Santa Cruz Biotechnology, Cayman Chemicals, among others. In one embodiment, the Wnt agonist is Wnt3A.

In some embodiments the dose of Wnt3A is e.g., at least 10 ng/mL, at least 15 ng/mL, at least 20 ng/mL, at least 25 ng/mL, at least 30 ng/mL, at least 40 ng/mL, at least 50 ng/mL, at least 60 ng/mL, or more.

PI3-K inhibitors: In some embodiments, the production of epicardial cells or cardiomyocytes useful in the compositions and methods described herein proceeds through the production of early mesoderm cells. For example, embryonic stem cells or induced pluripotent stem cells can be differentiated to early mesoderm cells using a protocol comprising, in part, contacting a hESC or hIPSC with a PI3K inhibitor (e.g., Ly294002).

Exemplary PI3K inhibitors include, but are not limited to, wortmannin, demethoxyviridin, LY294002, idelalisib, copanlisib, perifosine, buparlisib, duvelisib, alpelisib, umbralisib, copanlisib, PX-866, dactolisib, CUDC-997, ME-401, IPI-549, SF-1126, RP6530, INK1117, pictilisib, XL147, XL765, palomid 529, GSK1059615, ZSTK474, PWT33596, IC87114, TG100-115, CAL263, RP6503, PI-103, GNE-477, and AEZS-136. As the PI3K inhibitors as used herein are early in the differentiation process of embryonic or iPS cells to epicardial cells and PI3K activity may be required at later stages of differentiation, it may be preferable to select a reversible PI3K, such as Ly294002, for such differentiation steps.

In some embodiments, the dosage range for Ly294002 is between 1 and 25 µM, between 1 and 20 µM, between 1 and 15 µM, between 1 and 2 µM, between 5 and 15 µM, between 5 and 20 µM, between 5 and 25 µM, between 20 and 25 µM, between 10 and 25 µM, between 8 and 12 µM, between 8 and 15 µM, between 9 µM and 11 µM, or any range therebetween.

Retinoic acid: In some embodiments, production of an in vitro-differentiated epicardial cell, as that term is used herein, is performed, in part, by contacting a lateral mesoderm cell with retinoic acid or a derivative thereof. In some embodiments, the dosage range of retinoic acid is between 1 and 10 M, between 1 and 7.5 µM, between 1 and 5 µM, between 1 and 2 µM, between 7.5 and 10 µM, between 5 and 10 µM, between 3 and 10 µM, between 2 and 8 µM, between 3 and 7 µM, between 3 and 6 µM, between 3 and 5 µM, or any range therebetween.

Monitoring Differentiation of Cardiac Progenitor Cells to Cardiomyocytes and/or Epicardial Cells Provided herein are epicardial cells or cardiomyocytes generated by differentiating or redifferentiating a pluripotent stem cell (e.g., a mesoderm cell, a mid-streak primitive mesoderm cell, an ES cell or an iPSC). Such methods are exemplified in the Examples section herein. As will be appreciated by one of skill in the art, an in vitro-differentiated human cardiomyocyte or an in vitro-differentiated epicardial cell described herein will lack markers of hematopoietic or hemogenic cells, vascular endothelial cells, embryonic stem cells or induced pluripotent stem cells. In one embodiment of the methods described herein, one or more cell surface markers are used to determine the degree of differentiation along the spectrum of embryonic stem cells or iPSCs to e.g., fully differentiated cardiomyocytes or epicardial cells.

Cell surface markers, particularly stem cell surface markers, are useful with the methods and compositions described herein to identify the differentiation or dedifferentiation state of a cell. Since both the epicardial cells and cardiomyocytes share common cardiac progenitor cell markers, such early cardiac markers (e.g., Isl1+, SlK-1+, Nkx2.5+) can be used to determine commitment to the cardiac lineage, while later markers of differentiation can be used to differentiate epicardial cells from cardiomyocytes (e.g., pro-epicardial markers such as WT1+, TBX18+, or epicardial markers such as WT1+, TBX18+, ALDH1A2+). Both cell surface markers and intracellular markers can be detected, for example, using an antibody for binding, e.g., cell surface markers or by PCR for intracellular markers.

In some embodiments, antibodies or similar agents specific for a given marker, or set of markers, can be used to separate and isolate the desired cells using fluorescent activated cell sorting (FACS), panning methods, magnetic particle selection, particle sorter selection and other methods known to persons skilled in the art, including density separation (Xu et al. (2002) Circ. Res. 91:501; U.S.S.N. 20030022367) and separation based on other physical properties (Doevendans et al. (2000) J. Mol. Cell. Cardiol. 32:839-851). Negative selection can be performed, including selecting and removing cells with undesired markers or characteristics, for example fibroblast markers, epithelial cell markers etc.

Undifferentiated ES cells express genes that can be used as markers to detect the presence of undifferentiated cells. Exemplary ES cell markers include stage-specific embryonic antigen (SSEA)-3, SSEA-4, TRA-1-60, TRA-1-81, alkaline phosphatase or those described in e.g., U.S.S.N. 2003/0224411; or Bhattacharya (2004) Blood 103(8):2956-64, each herein incorporated by reference in their entirety. Exemplary markers expressed on cardiac progenitor cells include, but are not limited to, TMEM88, GATA4, ISL1, MYL4, and NKX2-5.

Exemplary markers expressed on cardiomyocytes include, but are not limited to, NKX2-5, MYH6, MYL7, TBX5, ATP2a2, RYR2, and cTnT.

In some embodiments, the desired cells (e.g., in vitro-differentiated epicardial cells) are an enriched population of cells; that is, the percentage of human in vitro-differentiated epicardial cells (e.g., percent of cells) in a population of cells is at least 10% of the total number of cells in the population. For example, an enriched population comprises at least 15% definitive epicardial cells, at least 20%, at least 30%, at least 40%, at least 50%, at least 60%, at least 70%, at least 80%, at least 90%, at least 95%, at least 99% or even 100% of the population comprises human in vitro-differentiated epicardial cells. In some embodiments, a population of cells comprises at least 100 cells, at least 500 cells, at least 1000 cells, at least $1\times10^4$ cells, at least $1\times10^5$ cells, at least $1\times10^6$ cells, at least $1\times10^7$ cells, at least $1\times10^8$ cells, at least $1\times10^9$ cells, at least $1\times10^{10}$ cells, at least $1\times10^{11}$ cells, at least $1\times10^{12}$ cells, at least $1\times10^{13}$ cells, at least $1\times10^{14}$ cells, at least $1\times10^{15}$ cells, or more.

Scaffold Compositions

In one aspect, the cardiomyocytes and/or epicardial cells described herein can be admixed with or grown in or on a preparation that provides a scaffold to support the cells. Such a scaffold can provide a physical advantage in securing the cells in a given location, e.g., after implantation, as well as a biochemical advantage in providing, for example, extracellular cues for the further maturation or, e.g., maintenance of phenotype until the cells are established.

Biocompatible synthetic, natural, as well as semi-synthetic polymers, can be used for synthesizing polymeric particles that can be used as a scaffold material. In general, for the practice of the methods described herein, it is preferable that a scaffold biodegrades such that the cardiomyocytes and/or epicardial cells can be isolated from the polymer prior to implantation or such that the scaffold degrades over time in a subject and does not require removal. Thus, in one embodiment, the scaffold provides a temporary structure for growth and/or delivery of cardiomyocytes and/or epicardial cells to a subject in need thereof. In some embodiments, the scaffold permits human cells to be grown in a shape suitable for transplantation or administration into a subject in need thereof, thereby permitting removal of the scaffold prior to implantation and reducing the risk of rejection or allergic response initiated by the scaffold itself.

Examples of polymers which can be used include natural and synthetic polymers, although synthetic polymers are preferred for reproducibility and controlled release kinetics. Synthetic polymers that can be used include biodegradable polymers such as poly(lactide) (PLA), poly(glycolic acid) (PGA), poly(lactide-co-glycolide) (PLGA), and other polyhydroxyacids, poly(caprolactone), polycarbonates, polyamides, polyanhydrides, polyphosphazene, polyamino acids, polyorthoesters, polyacetals, polycyanoacrylates and biodegradable polyurethanes; non-biodegradable polymers such as polyacrylates, ethylene-vinyl acetate polymers and other acyl-substituted cellulose acetates and derivatives thereof, polyurethanes, polystyrenes, polyvinyl chloride, polyvinyl fluoride, poly(vinyl imidazole), chlorosulphonated polyolefins, and polyethylene oxide. Examples of biodegradable natural polymers include proteins such as albumin, collagen, fibrin, silk, synthetic polyamino acids and prolamines; polysaccharides such as alginate, heparin; and other naturally occurring biodegradable polymers of sugar units. Alternately, combinations of the aforementioned polymers can be used. In one aspect, a natural polymer that is not generally found in the extracellular matrix can be used.

PLA, PGA and PLA/PGA copolymers are particularly useful for forming biodegradable scaffolds. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136; 3,531,561 to Trehu.

PGA is a homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture", Chemistry and Industry, 905 (1970).

Fibers can be formed by melt-spinning, extrusion, casting, or other techniques well known in the polymer processing area. Preferred solvents, if used to remove a scaffold prior to implantation, are those which are completely removed by the processing or which are biocompatible in the amounts remaining after processing.

Polymers for use in the matrix should meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy.

Scaffolds can be of any desired shape and can comprise a wide range of geometries that are useful for the methods described herein. A non-limiting list of shapes includes, for example, patches, hollow particles, tubes, sheets, cylinders, spheres, and fibers, among others. The shape or size of the scaffold should not substantially impede cell growth, cell differentiation, cell proliferation or any other cellular process, nor should the scaffold induce cell death via e.g., apoptosis or necrosis. In addition, care should be taken to ensure that the scaffold shape permits appropriate surface area for delivery of nutrients from the surrounding medium to cells in the population, such that cell viability is not impaired. The scaffold porosity can also be varied as desired by one of skill in the art.

In some embodiments, attachment of the cells to a polymer is enhanced by coating the polymers with compounds such as basement membrane components, fibronectin, agar, agarose, gelatin, gum arabic, collagens types I, II, III, IV, and V, laminin, glycosaminoglycans, polyvinyl alcohol, mixtures thereof, and other hydrophilic and peptide attachment materials known to those skilled in the art of cell culture or tissue engineering. Examples of a material for coating a polymeric scaffold include polyvinyl alcohol and collagen. As will be appreciated by one of skill in the art, Matrigel™ is not suitable for administration to a human subject, thus the compositions described herein do not include Matrigel™.

In some embodiments it can be desirable to add bioactive molecules/factors to the scaffold. A variety of bioactive molecules can be delivered using the matrices described herein.

In one embodiment, the bioactive factors include growth factors. Examples of growth factors include platelet derived growth factor (PDGF), transforming growth factor alpha or beta (TGFβ), bone morphogenic protein 4 (BMP4), fibroblastic growth factor 7 (FGF7), fibroblast growth factor 10 (FGF10), epidermal growth factor (EGF/TGFα), vascular endothelium growth factor (VEGF), some of which are also angiogenic factors.

These factors are known to those skilled in the art and are available commercially or described in the literature. Bioactive molecules can be incorporated into the matrix and released over time by diffusion and/or degradation of the matrix, or they can be suspended with the cell suspension.

Treatment of Cardiac Disease and/or Injury

The heart is made of three major tissue layers: the endocardium, myocardium, and epicardium. The epicardium is the outermost epithelial layer of the heart and is responsible for the formation of coronary vascular smooth muscle cells. The epicardium can be re-activated to a more fetal form and/or the epicardial cells can undergo epithelial-to-mesenchymal transition (EMT) in response to an acute injury to the myocardium (e.g., a myocardial infarction). Provided herein are epicardial cells and uses thereof (e.g., co-administration with cardiomyocytes) in the treatment of cardiac injury, cardiac disease/disorder, and/or promoting vascularization and engraftment of co-administered cardiomyocytes.

The methods and compositions provided herein relate to a therapeutically effective amount of cardiomyocytes and/or epicardial cells (e.g., human cardiomyocytes and human epicardial cells). Thus, in some embodiments a therapeutically effective amount of cardiomyocytes is co-administered with epicardial cells to a subject to (i) repair infarcted zones of cardiac injury, (ii) promote recovery following cardiac ischemia or injury, and/or (iii) promote tissue repair and/or tissue engineering.

Accordingly, provided herein are methods for the treatment and prevention of a cardiac injury or a cardiac disease or disorder in a subject in need thereof. The methods described herein can be used to treat, ameliorate, prevent or slow the progression of a number of cardiac diseases or their symptoms, such as those resulting in pathological damage to the structure and/or function of the heart. The terms "cardiac disease," "cardiac disorder," and "cardiac injury," are used interchangeably herein and refer to a condition and/or disorder relating to the heart, including the functional engraftment and vascularization of cardiomyocytes into e.g., infarcted zones.

Such cardiac diseases or cardiac-related disease include, but are not limited to, myocardial infarction, heart failure, cardiomyopathy, congenital heart defect (e.g., non-compaction cardiomyopathy), hypertrophic cardiomyopathy, dilated cardiomyopathy, myocarditis, heart failure, and cardiomegaly.

As used herein, the terms "administering," "introducing" and "transplanting" are used interchangeably in the context of the placement of cells, e.g. cardiomyocytes and/or epicardial cells, as described herein into a subject, by a method or route which results in at least partial localization of the introduced cells at a desired site, such as a site of injury or repair, such that a desired effect(s) is produced. The cells e.g. epicardial cells, or their differentiated progeny (e.g. cardiac fibroblasts etc.) and cardiomyocytes can be implanted directly to the heart, or alternatively be administered by any appropriate route which results in delivery to a desired location in the subject where at least a portion of the implanted cells or components of the cells remain viable. The period of viability of the epicardial cells after administration to a subject can be as short as a few hours, e.g., twenty-four hours, to a few days, to as long as several years, i.e., long-term engraftment. As one of skill in the art will appreciate, long-term engraftment of the cardiomyocytes is desired as cardiomyocytes do not proliferate to an extent that the heart can heal from an acute injury comprising cardiomyocyte death. In other embodiments, the cells can be administered via an indirect systemic route of administration, such as an intraperitoneal or intravenous route.

When provided prophylactically, the cardiomyocytes and/or epicardial cells can be administered to a subject in advance of any symptom of a cardiac disorder, e.g., heart failure due to prior myocardial infarction or left ventricular insufficiency, congestive heart failure etc. Accordingly, the prophylactic administration of a population of cardiomyocytes and/or epicardial cells serves to prevent a cardiac heart failure disorder or maladaptive cardiac remodeling, as disclosed herein.

In some embodiments of the aspects described herein, the population of cells being administered according to the methods described herein comprises allogeneic cells or their obtained from one or more donors. As used herein, "allogeneic" refers to a cardiomyocyte and/or epicardial cell obtained from or derived from (e.g., differentiated from) one or more different donors of the same species, where the genes at one or more loci are not identical. For example, cardiomyocytes and/or epicardial cells being administered to a subject can be derived from umbilical cord blood obtained from one more unrelated donor subjects, or from one or more non-identical siblings. In some embodiments, syngeneic cell populations can be used, such as those obtained from genetically identical animals, or from identical twins. In other embodiments of this aspect, the cardiomyocytes and/or epicardial cells are autologous cells; that is, the cells are obtained or isolated from a subject (or derived from) and administered to the same subject, i.e., the donor and recipient are the same.

Pharmaceutically Acceptable Carriers

The methods of administering human cardiomyocytes and/or epicardial cells to a subject as described herein involve the use of therapeutic compositions comprising such cells. Therapeutic compositions contain a physiologically tolerable carrier together with the cell composition and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset, transplant rejection, allergic reaction, and the like. A pharmaceutically acceptable carrier will not promote the raising of an immune response to an agent with which it is admixed, unless so desired. The preparation of a composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared.

In general, the compositions comprising cardiomyocytes and/or epicardial cells described herein are administered are suspension formulations where the cells are admixed with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the human cardiac progenitor cells as described herein using routine experimentation.

A cell composition can also be emulsified or presented as a liposome composition, provided that the emulsification procedure does not adversely affect cell viability. The cells and any other active ingredient can be mixed with excipients which are pharmaceutically acceptable and compatible with the active ingredient and in amounts suitable for use in the therapeutic methods described herein.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

Administration and Efficacy

Provided herein are methods for treating a cardiac disease, a cardiac disorder, or a cardiac injury comprising administering cardiomyocytes and/or epicardial cells to a subject in need thereof. In some embodiments, methods and compositions are provided herein for the prevention of an anticipated cardiac disorder e.g., heart failure following myocardial injury.

Measured or measurable parameters include clinically detectable markers of disease, for example, elevated or depressed levels of a clinical or biological marker, as well as parameters related to a clinically accepted scale of symptoms or markers for a disease or disorder. It will be understood, however, that the total usage of the compositions and formulations as disclosed herein will be decided by the attending physician within the scope of sound medical judgment. The exact amount required will vary depending on factors such as the type of disease being treated.

The term "effective amount" as used herein refers to the amount of a population of cardiomyocytes and/or epicardial cells needed to alleviate at least one or more symptoms of a disease or disorder, including but not limited to a cardiac injury or a cardiac disease or disorder. An "effective amount" relates to a sufficient amount of a composition to provide the desired effect, e.g., treat a subject having an infarct zone following myocardial infarction, improve cardiomyocyte engraftment, prevent onset of heart failure following cardiac injury, enhance vascularization of a graft etc. The term "therapeutically effective amount" therefore refers to an amount of human cardiomyocytes and/or epicardial cells or a composition such cells that is sufficient to promote a particular effect when administered to a typical subject, such as one who has, or is at risk for, a cardiac disease or disorder. An effective amount as used herein would also include an amount sufficient to prevent or delay the development of a symptom of the disease, alter the course of a disease symptom (for example but not limited to, slow the progression of a symptom of the disease), or reverse a symptom of the disease. It is understood that for any given case, an appropriate "effective amount" can be determined by one of ordinary skill in the art using routine experimentation.

In some embodiments, the subject is first diagnosed as having a disease or disorder affecting the myocardium prior to administering the cells according to the methods described herein. In some embodiments, the subject is first diagnosed as being at risk of developing cardiac disease (e.g., heart failure following myocardial injury) or disorder prior to administering the cells.

For use in the various aspects described herein, an effective amount of human cardiomyocytes and/or epicardial cells comprises at least $1\times10^3$, at least $1\times10^4$, at least $1\times10^5$, at least $5\times10^5$, at least $1\times10^6$, at least $2\times10^6$, at least $3\times10^6$, at least $4\times10^6$, at least $5\times10^6$, at least $6\times10^6$, at least $7\times10^6$, at least $8\times10^6$, at least $9\times10^6$, at least $1\times10^7$, at least $1.1\times10^7$, at least $1.2\times10^7$, at least $1.3\times10^7$, at least $1.4\times10^7$, at least $1.5\times10^7$, at least $1.6\times10^7$, at least $1.7\times10^7$, at least $1.8\times10^7$, at least $1.9\times10^7$, at least $2\times10^7$, at least $3\times10^7$, at least $4\times10^7$, at least $5\times10^7$, at least $6\times10^7$, at least $7\times10^7$, at least $8\times10^7$, at least $9\times10^7$, at least $1\times10^8$, at least $2\times10^8$, at least $5\times10^8$, at least $7\times10^8$, at least $1\times10^9$, at least $2\times10^9$, at least $3\times10^9$, at least $4\times10^9$, at least $5\times10^9$ or more cardiomyocytes and/or epicardial cells.

In one embodiment, the ratio of cardiomyocytes to epicardial cells (CM:EPI) is 2:1. In other embodiments, the ratio of cardiomyocytes to epicardial cells is 1:1, 1.5:1, 2.25:1, 2.5:1, 2.75:1, 3:1, 3.5:1, 4:1, 5:1, 7.5:1, 10:1, 15:1, 20:1, 1:1.5, 1:2, 1:2.25, 1:2.5, 1:2.75, 1:3, 1:3.5, 1:4, 1:5, 1:7.5, 1:10, 1:15, 1:20 or any therapeutically effective ratio. One of skill in the art will appreciate that a desired ratio (e.g., optimal ratio) of cardiomyocytes to epicardial cells (e.g., for a given injury size) can be determined through animal studies or human clinical trials by assessing parameters such as engraftment size, functional engraftment, positive changes in LVESD or LVEDD etc.

In some embodiments, a composition comprising cardiomyocytes and epicardial cells permits engraftment of the cells in the heart at an efficiency at least 20% greater than the engraftment when such cardiomyocytes are administered alone; in other embodiments, such efficiency is at least 30%, at least 40%, at least 50%, at least 60%, at least 70%, at least 80%, at least 90%, at least 1-fold, at least 2-fold, at least 5-fold, at least 10-fold, at least 100-fold or more than the efficiency of engraftment when cardiomyocytes are administered alone.

In some embodiments, a therapeutically effective amount of cardiomyocytes and epicardial cells when administered in combination (e.g., co-administered) refers to an increase in the size of the cardiomyocyte graft of at least 10% (e.g., at least 20%, at least 30%, at least 40%, at least 50%, at least 60%, at least 70%, at least 80%, at least 90%, at least 1-fold, at least 2-fold, at least 5-fold, at least 10-fold, at least 100-fold or more) than the administration of substantially the same number of cardiomyocytes lacking epicardial cells. In one embodiment, the cardiomyocytes and/or epicardial cells are human cells.

In some embodiments, a therapeutically effective amount of cardiomyocytes and epicardial cells refers to an increase in the microvascular density or a marker thereof (e.g., of vascularization) by at least 20% (e.g., at least 30%, at least 40%, at least 50%, at least 60%, at least 70%, at least 80%, at least 90%, at least 1-fold, at least 2-fold, at least 5-fold, at least 10-fold, at least 100-fold or more) compared to the microvascular density or a marker thereof that occurs when cardiomyocytes are administered in the absence of epicardial cells. Exemplary markers of microvascular density include increased expression in one or more markers including, but not limited to, CD31, VE cadherin, von Willebrand factor (vWF), or by staining with a lectin that preferentially binds vascular endothelium (e.g., SNA-I, MAA, AIA, VAA I-III, WGA and/or LEA).

The cardiomyocytes and/or epicardial cells can be derived from one or more donors, or can be obtained from an autologous source. In some embodiments of the aspects described herein, the cardiomyocytes and/or epicardial cells are expanded in culture prior to administration to a subject in need thereof.

Exemplary modes of administration for use in the methods described herein include, but are not limited to, injection, intracardiac delivery, systemic administration and implantation (with or without a scaffold material). "Injection" includes, without limitation, intracardiac, intravenous, intramuscular, intraarterial, intradermal, intraperitoneal and subcutaneous.

In some embodiments, a therapeutically effective amount of cardiomyocytes and/or epicardial cells is administered using direct injection into the heart including, but not limited to administration during open-heart surgery or by intracardiac injection through an intact chest. In some aspects of these methods, a therapeutically effective amount of cardiomyocytes and/or epicardial cells are administered using a systemic, such as an intraperitoneal or intravenous route. In other aspects of these methods, a therapeutically effective amount of cardiomyocytes and/or epicardial cells is administered using systemic or intraperitoneal administration. These methods are particularly aimed at therapeutic and prophylactic treatments of human subjects having, or at risk of having, a cardiac disease or disorder. The human cardiomyocytes and/or epicardial cells) described herein can be administered to a subject having any cardiac disease or disorder by any appropriate route which results in an effective treatment in the subject. In some embodiments of the aspects described herein, a subject having a cardiac disorder is first selected prior to administration of the cells.

In some embodiments, an effective amount of cardiomyocytes and/or epicardial cells are administered to a subject by intracardiac administration or delivery. As defined herein, "intracardiac" administration or delivery refers to all routes of administration whereby a population of cardiomyocytes and/or epicardial cells is administered in a way that results in direct contact of these cells with the myocardium of a subject, including, but not limited to, direct cardiac injection, intra-myocardial injection(s), intra-infarct zone injection, injection during surgery (e.g., cardiac bypass surgery, during implantation of a cardiac mini-pump or a pacemaker, etc.). In some such embodiments, the cells are injected into the myocardium (e.g., cardiomyocytes), or into the cavity of the atria and/or ventricles. In some embodiments, intracardiac delivery of cells includes administration methods whereby cells are administered, for example as a cell suspension, to a subject undergoing surgery via a single injection or multiple "mini" injections into the desired region of the heart.

In some embodiments, an effective amount of cardiomyocytes and/or epicardial cells is administered to a subject by systemic administration, such as intravenous administration.

The phrases "systemic administration," "administered systemically", "peripheral administration" and "administered peripherally" are used herein refer to the administration of a population of cardiomyocytes and/or epicardial cells other than directly into a target site, tissue, or organ, such as the heart, such that it enters, instead, the subject's circulatory system.

The choice of formulation will depend upon the specific composition used and the number of cardiomyocytes and/or epicardial cells to be administered; such formulations can be adjusted by the skilled practitioner. However, as an example, where the composition is cardiomyocytes and/or epicardial cells in a pharmaceutically acceptable carrier, the composition can be a suspension of the cells in an appropriate buffer (e.g., saline buffer) at an effective concentration of cells per mL of solution. The formulation can also include cell nutrients, a simple sugar (e.g., for osmotic pressure regulation) or other components to maintain the viability of the cells. Alternatively, the formulation can comprise a scaffold, such as a biodegradable scaffold.

In some embodiments, additional agents to aid in treatment of the subject can be administered before or following treatment with the cardiomyocytes and/or epicardial cells as described. Such additional agents can be used to prepare the target tissue for administration of the progenitor cells. Alternatively, the additional agents can be administered after the cardiomyocytes and/or epicardial cells to support the engraftment and growth of the administered cell into the heart or other desired administration site. In some embodiments, the additional agent comprises growth factors, such as VEGF or PDGF. Other exemplary agents can be used to reduce the load on the heart while the cardiomyocytes are engrafting (e.g., beta blockers, medications to lower blood pressure etc.).

The efficacy of treatment can be determined by the skilled clinician. However, a treatment is considered "effective treatment," as the term is used herein, if any one or all of the symptoms, or other clinically accepted symptoms or markers of disease, e.g., cardiac disease, heart failure, cardiac injury and/or a cardiac disorder are reduced, e.g., by at least 10% following treatment with a composition comprising human cardiomyocytes and/or epicardial cells as described herein. Methods of measuring these indicators are known to those of skill in the art and/or described herein.

Indicators of cardiac disease or cardiac disorder, or cardiac injury include functional indicators or parameters, e.g., stroke volume, heart rate, left ventricular ejection fraction, heart rate, heart rhythm, blood pressure, heart volume, regurgitation, etc. as well as biochemical indicators, such as a decrease in markers of cardiac injury, such as serum lactate dehydrogenase, or serum troponin, among others. As one example, myocardial ischemia and reperfusion are associated with reduced cardiac function. Subjects that have suffered an ischemic cardiac event and/or that have received reperfusion therapy have reduced cardiac function when compared to that before ischemia and/or reperfusion. Measures of cardiac function include, for example, ejection fraction and fractional shortening. Ejection fraction is the fraction of blood pumped out of a ventricle with each heartbeat. The term ejection fraction applies to both the right and left ventricles. LVEF refers to the left ventricular ejection fraction (LVEF). Fractional shortening refers to the difference between end-diastolic and end-systolic dimensions divided by end-diastolic dimension.

Non-limiting examples of clinical tests that can be used to assess cardiac functional parameters include echocardiography (with or without Doppler flow imaging), electrocardiogram (EKG), exercise stress test, Holter monitoring, or measurement of β-natriuretic peptide.

Where necessary or desired, animal models of cardiac injury or cardiac disease can be used to gauge the effectiveness of a particular composition as described herein. For example, an isolated working rabbit or rat heart model, or a coronary ligation model in either canines or porcines can be used. Animal models of cardiac function are useful for monitoring infarct zones, coronary perfusion, electrical conduction, left ventricular end diastolic pressure, left ventricular ejection fraction, heart rate, blood pressure, degree of hypertrophy, diastolic relaxation function, cardiac output, heart rate variability, and ventricular wall thickness, etc.

In some embodiments, a composition comprising the cardiomyocytes and/or epicardial cells as described herein is delivered at least 6 hours following the initiation of reperfusion, for example, following a myocardial infarction. During an ischemic insult and subsequent reperfusion, the microenvironment of the heart or that of the infarcted zone can be too "hostile" to permit engraftment of cardiomyocytes and/or epicardial cells administered to the heart. Thus, in some embodiments it is preferable to administer such compositions at least 6 hours, at least 12 hours, at least 18 hours, at least 24 hours, at least 36 hours, at least 48 hours, at least 60 hours, at least 72 hours, at least 84 hours, at least 96 hours, at least 5 days, at least 6 days, at least 7 days, at least 8 days, at least 9 days, at least 10 days or more following the initiation of reperfusion. In some embodiments, the compositions comprising cardiomyocytes and/or epicardial cells as described herein can be administered to an infarcted zone, peri-infarcted zone, ischemic zone, penumbra, or the border zone of the heart at any length of time after a myocardial infarction (e.g., at least 1 month, at least 6 months, at least one year, at least 2 years, at least 5 years, at least 10 years, at least 20 years, at least 30 years or more), however as will be appreciated by those of skill in the art, the success of engraftment following a lengthy interval of time after infarct will depend on a number of factors, including but not limited to, amount of scar tissue deposition, density of scar tissue, size of the infarcted zone, degree of vascularization surrounding the infarcted zone, etc. As such, earlier intervention by administration of compositions comprising cardiomyocytes and/or epicardial cells may be more efficacious than administration after e.g., a month or more after infarct.

Compositions comprising cardiomyocytes and/or epicardial cells as described herein can be administered to any desired region of the heart including, but not limited to, an infarcted zone, peri-infarcted zone, ischemic zone, penumbra, the border zone, areas of wall thinning, areas of non-compaction, or in area(s) at risk of maladaptive cardiac remodeling.

Screening Assays

Compositions comprising cardiomyocytes and epicardial cells as described herein can be used in screening assays for determining the toxicity, or alternatively the efficacy of a bioactive agent on cardiomyocyte viability, cardiomyocyte maturation, cardiomyocyte electroconductivity etc. The use of e.g., a co-culture of cardiomyocytes and epicardial cells more closely mimics the tissue of an intact heart than simply culturing cardiomyocytes alone. In particular, adult cardiomyocytes are difficult to culture as they do not reproduce and thus cannot be expanded in vitro. Thus, differentiation of human stem cells to cardiac progenitors in vitro and their subsequent maturation using a co-culture of cardiomyocytes and epicardial cells is especially useful in producing epicardial and cardiomyocyte cells for screening bioactive agents for the treatment of disease, or to monitor cell toxicity of a variety of agents.

In some embodiments, a co-culture of cardiomyocytes and epicardial cells comprises a 3-dimensional cell culture, or are cast in a tissue construct as described herein in the working Examples.

In some embodiments, co-cultured human cardiomyocytes and epicardial cells can be used in methods, assays, systems and kits to develop specific in vitro assays. Such assays for drug screening and toxicology studies have an advantage over existing assays because they are of human origin, do not require immortalization of cell lines, nor do they require tissue from cadavers, which poorly reflect the physiology of normal human cells. For example, the methods, assays, systems, and kits described herein can be used to identify and/or test agents that can promote cardiomyocyte maturation (e.g., as assessed by measuring sarcomere length), cell viability, cardiomyocyte electroconductivity (e.g., morphologically beating in unison or near-unison; expression of connexin 43; propagation of an action potential when stimulated with an electrode) etc. In addition, or in the alternative, the methods, assays, systems, and kits can be used to identify and/or test for agents useful in treating a cardiac disease or disorder, or for preventing/treating a cardiac injury (e.g., cardiac hypertrophy, heart failure etc.).

Accordingly, provided herein are methods for screening a test compound for biological activity, the method comprising (a) contacting a co-culture of human cardiomyocytes and epicardial cells with a test compound and (b) determining any effect of the compound on the cell(s) or a desired cell parameter. The effect on the cell can be one that is observable directly, or indirectly by use of reporter molecules.

As used herein, the term "biological activity" or "bioactivity" refers to the ability of a test compound to affect a biological sample. Biological activity can include, without limitation, elicitation of a stimulatory, inhibitory, regulatory, toxic or lethal response in a biological assay. For example, a biological activity can refer to the ability of a compound to modulate the effect of an enzyme, block a receptor, stimulate a receptor, modulate the expression level of one or more genes, modulate cell proliferation, modulate cell division, modulate cell metabolism, modulate cell morphology, or a combination thereof. In some instances, a biological activity can refer to the ability of a test compound to produce a toxic effect in a biological sample.

As discussed above, the specific lineage of an in vitro-derived cardiomyocyte and/or epicardial cell can be a lineage which is phenotypic and/or genotypic of a disease (e.g., a cardiac disease).

As used herein, the term "test compound" or "candidate agent" refers to an agent or collection of agents (e.g., compounds) that are to be screened for their ability to have an effect on the cell. Test compounds can include a wide variety of different compounds, including chemical compounds, mixtures of chemical compounds, e.g., polysaccharides, small organic or inorganic molecules (e.g. molecules having a molecular weight less than 2000 Daltons, less than 1000 Daltons, less than 1500 Dalton, less than 1000 Daltons, or less than 500 Daltons), biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

Depending upon the particular embodiment being practiced, the test compounds can be provided free in solution, or can be attached to a carrier, or a solid support, e.g., beads. A number of suitable solid supports can be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group.

A number of small molecule libraries are known in the art and are commercially available. These small molecule libraries can be screened using the screening methods described herein. A chemical library or compound library is a collection of stored chemicals that can be used in conjunction with the methods described herein to screen candidate agents for a particular effect. A chemical library also comprises information regarding the chemical structure, purity, quantity, and physiochemical characteristics of each compound. Compound libraries can be obtained commercially, for example, from Enzo Life Sciences, Aurora Fine Chemicals, Exclusive Chemistry Ltd., ChemDiv, ChemBridge, TimTec Inc., AsisChem, and Princeton Biomolecular Research, among others.

Without limitation, the compounds can be tested at any concentration that can exert an effect on the cells relative to a control over an appropriate time period. In some embodiments, compounds are tested at concentrations in the range of about 0.01 nM to about 100 mM, about 0.1 nM to about 500 µM, about 0.1 µM to about 20 µM, about 0.1 µM to about 10 µM, or about 0.1 µM to about 5 µM.

The compound screening assay can be used in a high through-put screen. High through-put screening is a process in which libraries of compounds are tested for a given activity. High through-put screening seeks to screen large numbers of compounds rapidly and in parallel. For example, using microtiter plates and automated assay equipment, a laboratory can perform as many as 100,000 assays per day in parallel.

The compound screening assays described herein can involve more than one measurement of the cell or reporter function (e.g., measurement of more than one parameter and/or measurement of one or more parameters at multiple points over the course of the assay). Multiple measurements can allow for following the biological activity over incubation time with the test compound. In one embodiment, the reporter function is measured at a plurality of times to allow monitoring of the effects of the test compound at different incubation times.

The screening assay can be followed by a subsequent assay to further identify whether the identified test compound has properties desirable for the intended use. For example, the screening assay can be followed by a second assay selected from the group consisting of measurement of any of: bioavailability, toxicity, or pharmacokinetics, but is not limited to these methods.

Kits

Another aspect of the technology described herein relates to kits for treating a cardiac disease or disorder, kits for screening a candidate agent, and/or kits for co-culturing cardiomyocytes and epicardial cells. Described herein are kit components that can be included in one or more of the kits described herein.

Another aspect of the technology disclosed herein relates to kits to produce cardiomyocyte or epicardial cell according to the methods as disclosed herein.

In some embodiments, the components described herein can be provided singularly or in any combination as a kit. The kit includes the components described herein, e.g., a composition(s) that includes a compound(s) described herein, e.g., a compound or cocktail of compounds or reagents for differentiating a human stem cell to a cardiomyocyte or epicardial cell. Such kits can optionally include one or more agents that permit the detection of a cardiac progenitor cell marker or a cardiac cell marker or set thereof. In addition, the kit optionally comprises informational material.

In some embodiments, the compound in the kit can be provided in a watertight or gas tight container which in some embodiments is substantially free of other components of the kit. For example, a signaling pathway or differentiation pathway modulating compound can be supplied in more than one container, e.g., it can be supplied in a container having sufficient reagent for a predetermined number of differentiation reactions, e.g., 1, 2, 3 or greater. One or more compound as described herein can be provided in any form, e.g., liquid, dried or lyophilized form. It is preferred that the compound(s) described herein are substantially pure and/or sterile. When the one or more signaling pathway modulating compounds described herein is provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The informational material can be descriptive, instructional, marketing or other material that relates to the methods described herein and/or the use of a compound(s) described herein for the methods described herein. The informational material of the kits is not limited in its form. In one embodiment, the informational material can include information about production of the compound, molecular weight of the compound, concentration, date of expiration, batch or production site information, and so forth. In one embodiment, the informational material relates to methods for using or administering the compound.

In one embodiment, the informational material can include instructions to administer a human cardiomyocyte and/or epicardial cell thereof as described herein in a suitable manner to effect treatment of a cardiac injury or a cardiac disease or disorder, e.g., in a suitable dose, dosage form, or mode of administration (e.g., a dose, dosage form, or mode of administration described herein). In another embodiment, the informational material can include instructions for differentiating a human stem cell to a human cardiomyocyte or epicardial cell. Alternatively, the informational material can include instructions for screening a candidate agent for treating a cardiac disease or disorder.

In addition to a compound(s) described herein, the composition of the kit can include other ingredients, such as a solvent or buffer, a stabilizer, a preservative, and/or an additional agent, e.g., for differentiating stem cells (e.g., in vitro) or for treating a condition or disorder described herein. Alternatively, the other ingredients can be included in the kit, but in different compositions or containers than a cell or signaling pathway or differentiation pathway modulating compound described herein. In such embodiments, the kit can include instructions for admixing a compound(s) described herein and the other ingredients, or for using a compound(s) described herein together with the other ingredients, e.g., instructions on combining the two agents prior to use or administration.

The kit can include a component for the detection of a marker for human cardiac progenitor cells, ES cells iPS cells, cardiomyocytes, epicardial cells, hematopoietic cells, vascular endothelial cells etc. In addition, the kit can include one or more antibodies that bind a cell marker, or primers for an RT-PCR or PCR reaction, e.g., a semi-quantitative or quantitative RT-PCR or PCR reaction. Such components can be used to assess the activation of cardiac cell-specific markers or the loss of ES cell, iPSC, or adult stem cell markers. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The kit can also include one or more reagents for enhancing the efficiency of induced pluripotent stem cell production, such as an HDAC inhibitor (e.g., valproic acid) or a DNA methyltransferase inhibitor (e.g., 5azaC).

In one embodiment, the kit comprises a cell or tissue medium for cardiac mesoderm generation. In one embodiment, the medium comprises Activin A and BMP4.

The kit will typically be provided with its various elements included in one package, e.g., a fiber-based, e.g., a cardboard, or polymeric, e.g., a Styrofoam box. The enclosure can be configured so as to maintain a temperature differential between the interior and the exterior, e.g., it can provide insulating properties to keep the reagents at a preselected temperature for a preselected time.

The present invention may be as described in any one of the following numbered paragraphs:

1. A transplant composition comprising human cardiomyocytes and in vitro-differentiated human epicardial cells or the differentiated progeny of such human epicardial cells.

2. The transplant composition of paragraph 1, wherein the human cardiomyocytes are in vitro-differentiated.

3. The transplant composition of paragraph 1 or paragraph 2, wherein the epicardial cells or their progeny, the cardiomyocytes, or both, are differentiated from embryonic stem cells or from induced pluripotent stem cells.

4. The transplant composition of any one of paragraphs 1-3, wherein the epicardial cells or their progeny, the cardiomyocytes, or both, are differentiated from iPS cells autologous to a transplant recipient.

5. The transplant composition of any one of paragraphs 1-4, wherein the epicardial cells express fibronectin.

6. The transplant composition of any one of paragraphs 1-5, further comprising one or more of ZVAD-FMK, Bcl-XL, cyclosporine A, pinacidil, and IGF-1.

7. The transplant composition of any one of paragraphs 1-6, wherein the cardiomyocytes are present at a ratio of about 2:1 relative to the epicardial cells or progeny thereof.

8. The transplant composition of any one of paragraphs 1-7, which engrafts at least 20% more efficiently than a similar composition lacking the epicardial cells or their progeny.

9. A cardiac delivery device comprising a transplant composition of any one of paragraphs 1-8.

10. A tissue particle comprising a human cardiomyocyte in physical association with an in vitro-differentiated human epicardial cell or differentiated progeny thereof, in a culture medium or a cocktail comprising one or more of ZVAD-FMK, Bcl-XL, cyclosporine A, pinacidil, and IGF-1.

11. The tissue particle of paragraph 10, wherein the particle comprises from 2 to 2500 cells.

12. The tissue particle of paragraph 10, wherein the ratio of cardiomyocytes to epicardial cells or differentiated progeny thereof is about 2:1.

13. The tissue particle of any one of paragraphs 10-12, wherein the epicardial cell, the cardiomyocyte, or both is differentiated from an embryonic stem cell or an induced pluripotent stem cell.

14. The tissue particle of any one of paragraphs 10-13, wherein the cardiomyocyte is in vitro differentiated.

15. The tissue particle of any one of paragraphs 10-14, wherein the cardiomyocyte(s), the epicardial cell(s), or both is/are in vitro differentiated from an embryonic stem cell or an induced pluripotent stem cell.

16. A method of promoting engraftment of cardiomyocytes into cardiac tissue, comprising administering to cardiac tissue of a subject in need thereof a composition comprising epicardial cells in admixture with cardiomyocytes.

17. The method of paragraph 16, wherein the subject has suffered a cardiac infarction.

18. The method of paragraph 16, wherein the composition comprising epicardial cells in admixture with cardiomyocytes is a transplant composition of any one of paragraphs 1-8 or comprises a tissue particle of any one of paragraphs 10-15.

19. A method of promoting a mature phenotype of transplanted human cardiomyocytes, the method comprising administering to cardiac tissue of a subject in need thereof, a composition comprising human cardiomyocytes in admixture with human epicardial cells.

20. The method of paragraph 19, wherein the subject has suffered a cardiac infarction.

21. The method of paragraph 19, wherein the composition comprising human cardiomyocytes in admixture with human epicardial cells is a transplant composition of any one of paragraphs 1-8 or comprises a tissue particle of any one of paragraphs 10-15.

22. The method of any one of paragraphs 19-21, wherein the cardiomyocyte maturity is indicated by one or more of an increase in sarcomere length, an increase in cardiomyocyte diameter or length, expression of the cardiac isoform, cTnT, of troponin, and connexin 43 expression when cardiomyocytes are transplanted in admixture with epicardial cells, relative to cardiomyocyte transplantation alone.

23. A method of increasing microvascular density at the site of a cardiac cardiomyocyte transplant, the method comprising administering to cardiac tissue of a subject in need thereof a composition comprising human cardiomyocytes in admixture with human epicardial cells.

24. The method of paragraph 23, wherein the subject has suffered a cardiac infarction.

25. The method of paragraph 23 or 24, wherein the composition comprising human cardiomyocytes in admixture with human epicardial cells is a transplant composition of any one of paragraphs 1-8 or comprises a tissue particle of any one of paragraphs 10-15.

26. The method of any one of paragraphs 23-25, wherein microvascular density or a marker thereof is increased by at least 10% relative to that occurring when a cardiomyocyte transplant lacking epicardial cells is administered.

27. The method of any one of paragraphs 23-26, wherein microvascular density is indicated by expression of one or more of CD31, VE cadherin, von Willebrand factor (vWF) or by staining with a lectin that preferentially binds vascular endothelium.

28. A method of increasing cardiomyocyte graft size in a cardiac tissue, the method comprising administering to cardiac tissue of a subject in need thereof a composition comprising human cardiomyocytes in admixture with human epicardial cells.

29. The method of paragraph 28, wherein the subject has suffered a cardiac infarction.

30. The method of paragraph 28 or 29, wherein the composition comprising human cardiomyocytes in admixture with human epicardial cells is a transplant composition of any one of paragraphs 1-8 or comprises a tissue particle of any one of paragraphs 10-15.

31. The method of any one of paragraphs 28-30, wherein cardiomyocyte graft size is increased at least 10% by administering a composition comprising human cardiomyocytes in admixture with human epicardial cells relative to administration of a composition comprising substantially the same number of human cardiomyocytes but lacking human epicardial cells.

32. A method of promoting the maturity of in vitro-differentiated cardiomyocytes, the method comprising culturing in vitro differentiated cardiomyocytes in the presence of epicardial cells, differentiated progeny thereof, or epicardial cell conditioned medium.

33. The method of paragraph 32, wherein the cardiomyocytes and epicardial cells are human.

34. The method of paragraph 32 or 33, wherein the epicardial cells are in vitro differentiated.

35. The method of any one of paragraphs 32-34, wherein the epicardial cells, the cardiomyocytes or both are in vitro differentiated from embryonic stem cells or from induced pluripotent stem cells.

36. The method of any one of paragraphs 32-35, wherein cardiomyocyte maturity is indicated by one or more of an increase in sarcomere length in an engineered tissue or in a graft, an increase in cardiomyocyte diameter or length, expression of the cardiac isoform, cTnT, of troponin, and connexin 43 expression.

37. A method of promoting electrical connection between transplanted and recipient cardiomyocytes, the method comprising administering a transplant composition comprising cardiomyocytes in admixture with epicardial cells.

38. The method of paragraph 37, wherein the cardiomyocytes and epicardial cells are human.

39. The method of paragraph 37 or 38, wherein the cardiomyocytes, the epicardial cells, or both are in vitro differentiated.

40. The method of any one of paragraphs 37-39, wherein the epicardial cells, the cardiomyocytes or both are in vitro differentiated from embryonic stem cells or from induced pluripotent stem cells.

41. The method of any one of paragraphs 37-40, wherein the expression of connexin 43 is increased in transplanted cardiomyocytes administered in admixture with epicardial cells relative to connexin 43 expression in transplanted cardiomyocytes administered without epicardial cells.

42. A method of increasing the proliferation of transplanted cardiomyocytes, the method comprising administering a transplant composition comprising cardiomyocytes in admixture with epicardial cells or the differentiated progeny thereof.

43. The method of paragraph 42, wherein the cardiomyocytes, the epicardial cells or both are in vitro differentiated.

44. The method of paragraph 42 or 43, wherein the cardiomyocytes, the epicardial cells or both are in vitro differentiated from embryonic stem cells or from induced pluripotent stem cells.

45. The method of any one of paragraphs 42-44, wherein the transplant composition comprises a composition of any one of paragraphs 1-8, or comprises a tissue particle of any one of paragraphs 10-15.

46. A method of treating a cardiac infarction, the method comprising administering to cardiac tissue of a subject in need thereof a composition of any one of paragraphs 1-8, or a tissue particle of any one of paragraphs 10-15.

47. The method of paragraph 46, wherein one or more of engraftment, proliferation, maturity or function of transplanted cardiomyocytes is improved relative to administration of a composition comprising substantially the same number of cardiomyocytes, but lacking epicardial cells.

48. A method of making a cardiomyocyte transplant composition, the method comprising: providing a preparation of in vitro-differentiated human cardiomyocytes; providing a preparation of in vitro-differentiated human epicardial cells; and admixing the cardiomyocytes with the epicardial cells in a composition comprising one or more of ZVAD-FMK, Bcl-XL, cyclosporin A, pinacidil and IGF-1.

49. The method of paragraph 48, wherein the cardiomyocytes, the epicardial cells, or both are differentiated from embryonic stem cells or induced pluripotent stem cells.

50. The method of paragraph 48 or 49, wherein the cardiomyocytes and epicardial cells are present in admixture at a ratio of about 2:1.

51. The method of any one of paragraphs 48-50, further comprising heat shocking the epicardial cells and the cardiomyocytes prior to transplantation.

52. The method of any one of paragraphs 48-51, wherein the cardiomyocytes are heat shocked prior to being frozen for storage, and thawed to provide the preparation of cardiomyocytes used in the method.

53. The method of any one of paragraphs 48-52, wherein the epicardial cells are heat shocked on the day before they are to be used to make a cardiomyocyte transplant composition.

EXAMPLES

Summary hESC-derived epicardium was tested in 3D-engineered heart tissue (EHT) in vitro to study its inductive effects on cardiomyocyte maturation, and then the regenerative potency of directly injected epicardial cells was evaluated in a rat model of myocardial infarction. Cardiomyocytes derived from human embryonic stem cells (hESC) have advanced efforts to repair the infarcted heart. However, limitations such as immaturity of the cells, suboptimal cell survival and proliferation rates remain as a barrier to therapeutic cardiac repair. Seeking to overcome these challenges, hESC-derived epicardial cells are used in this study. Such cells are recognized for their pivotal role during embryonic heart development.

As shown in this study, epicardial cells promoted cardiomyocyte maturation and function in 3D-EHT. Co-transplantation of epicardial cells and cardiomyocytes in vivo resulted in greater cardiac graft size, superior host tissue remodeling and higher cardiac function compared with controls receiving either cardiomyocytes or epicardial cells alone or vehicle. The ability of epicardial cells to promote cardiac graft size and function make them a promising adjuvant therapeutic for cardiac regeneration following myocardial infarction and encourages their use in the long-standing dilemma of cardiac maturation.

Example 1: Human Embryonic Stem Cell Derived Epicardial Cells Augment Cardiomyocyte-Driven Heart Regeneration Despite major advances in the treatment of heart failure due to systolic impairment, therapeutic approaches have fallen short of addressing the cause of the problem; injury of the mammalian heart leads to irreversible loss of contractile myocardial tissue which is incapable of regeneration. At the turn of the millennium heart failure was widely identified as an emerging epidemic (1). To date 5.6 million patients in the US alone and 23 million worldwide are suffering from heart failure with 50% dying within 5 years after being diagnosed (2, 3). Current treatment is limited to ameliorating symptoms and slowing the natural progression of the disease but fails to compensate for the loss of contractile myocardium post-injury.

Regenerative medicine may hold the key to effectively treating heart failure by using stem cell-derived cardiovascular cells and tissues to restore full contractile function. Of all stem cell types, human embryonic stem cells (hESC) have the greatest potential for forming cardiovascular tissues, reliably giving rise to cardiomyocytes (4-6), endothelial cells (7, 8), smooth muscle cells (9) and more recently also epicardial cells (10, 11) under chemically defined conditions. Furthermore, hESC-derived cardiomyocytes have been successfully used to remuscularize infarcted rodent hearts, resulting in electrical integration and preserving cardiac function (6, 12). The clinical applicability of this technology has also been demonstrated in non-human primate models, where transplantation of human pluripotent stem cell (hPSC)-derived cardiomyocytes resulted in substantial reconstitution of the infarcted heart (13, 14).

While attempts to regenerate the mammalian heart have made some progress, hurdles such as relative immaturity of transplanted cells, suboptimal graft retention, cellular proliferation and graft size remain. Currently the hPSC-derived cardiomyocytes at best resemble cardiomyocytes found in a first trimester embryo, which may limit the functional benefits post-transplantation (15). To date little attention has been devoted to a supportive cell type that would promote maturity of hESC-derived cardiomyocytes and their survival post-transplantation in vivo.

In early mammalian heart development, the epicardium plays a pivotal role as a cardiovascular progenitor source and provides trophic support for developing cardiomyocytes. Giving rise to coronary smooth muscle cells, it is essential for the formation of a functioning coronary vasculature (16, 17). Moreover, epicardium-derived cells are paramount for cardiac proliferation, compaction and maturation (1820). Given its trophic role in embryonic heart development it was hypothesized that epicardial cells could promote cardiomyocyte maturation and contractility in hESC-based 3D-EHTs in vitro and by co-transplanting them with hESC-derived cardiomyocytes in vivo.

Data provided herein indicate that hESC-derived epicardium promoted the development of 3D-EHTs in vitro and cardiac grafts in vivo via cardiomyocyte maturation, proliferation and contraction. HESC-derived epicardial cells increased endogenous neo-vessel development, thus creating a favorable niche for hESC-derived cardiomyocytes in a hostile environment. Recapitulating key developmental steps, the epicardium augmented cardiomyocyte function making it a promising adjuvant therapy in regenerative medicine.

Figure 1E:
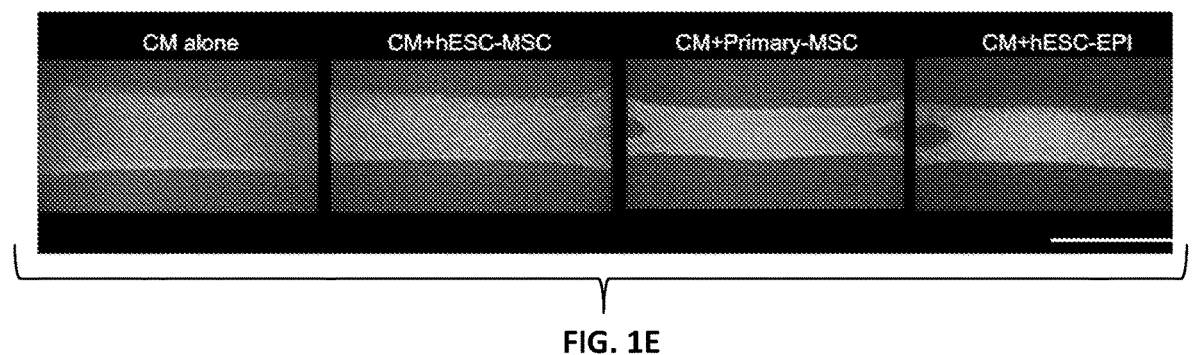
Figure 1F:
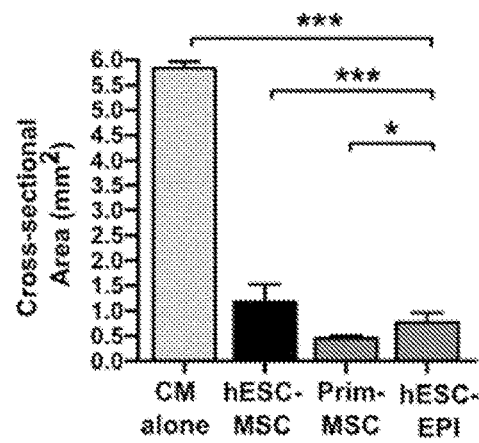
Figure 1G:
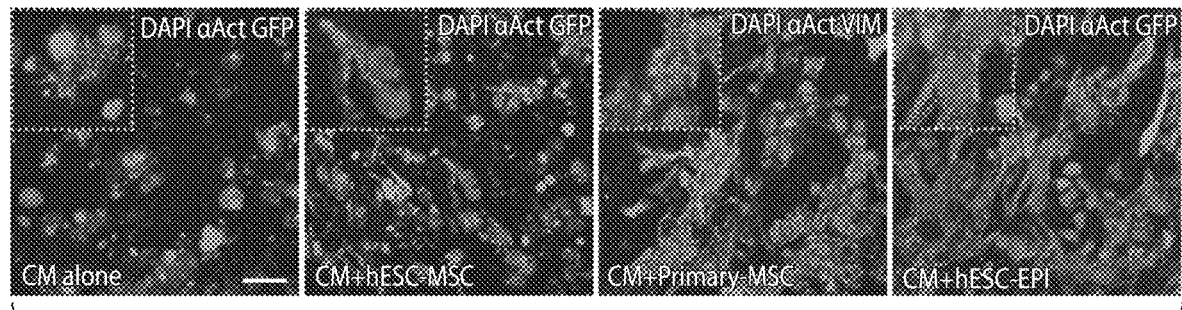
Figure 1H:
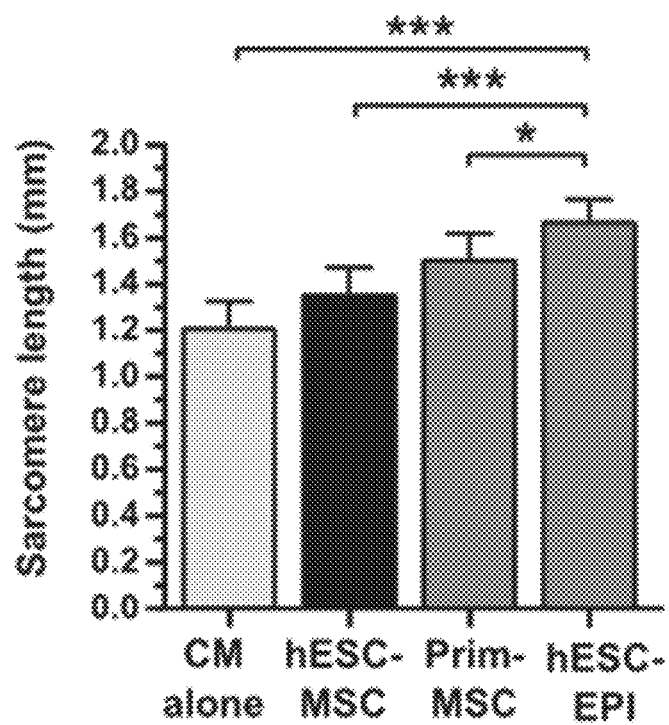
Figure 6A:
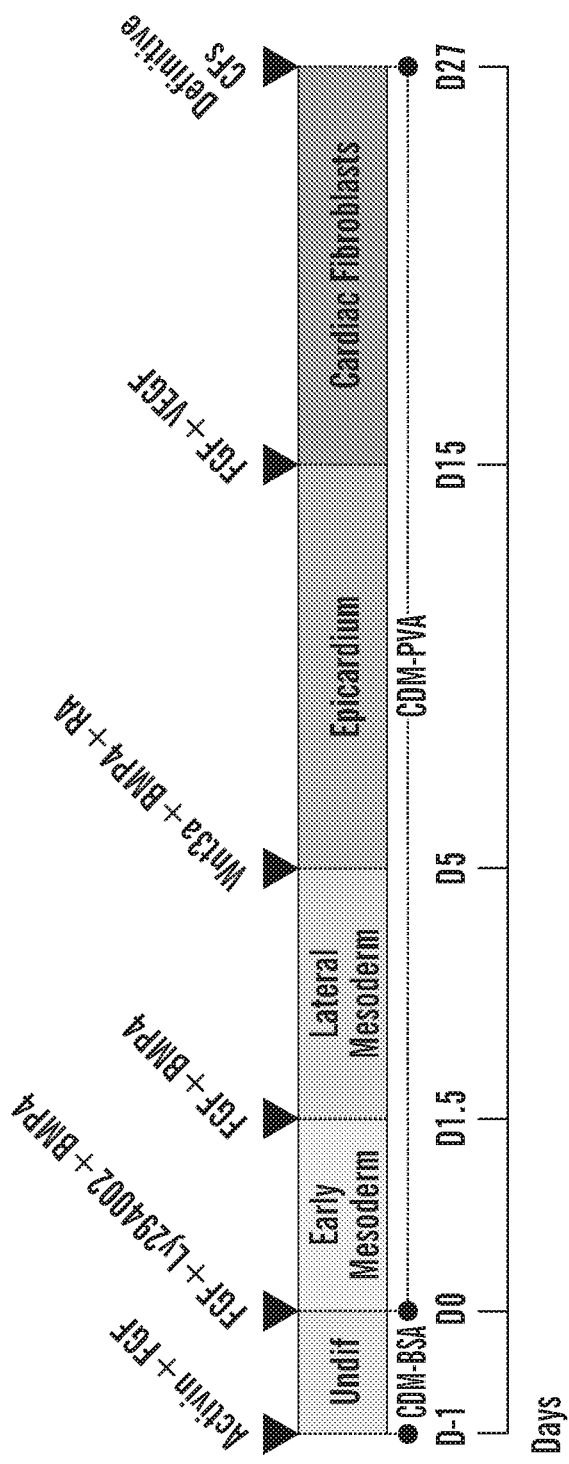
FIGS. 6A-6C. HESC-derived epicardial cells undergo EMT to cardiac fibroblasts in vitro under chemically defined conditions.
Figure 6B:
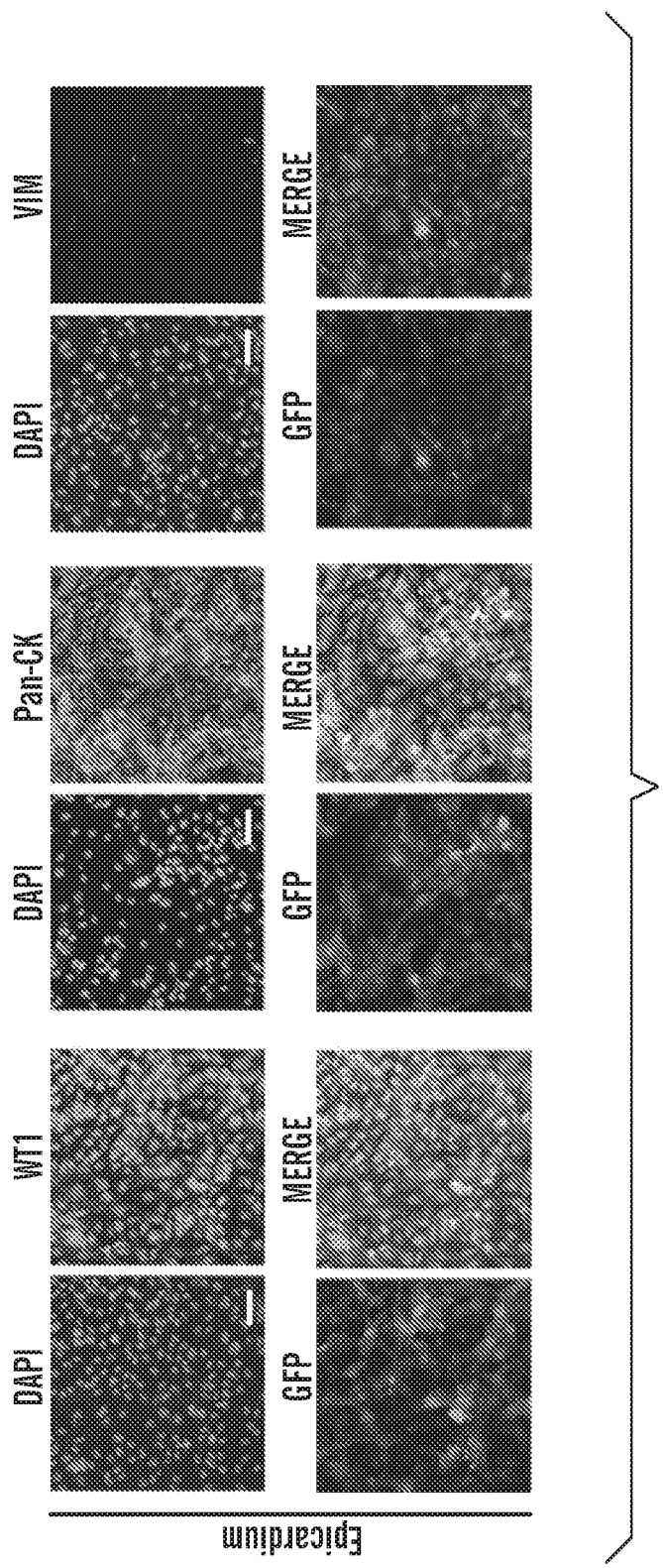
Figure 6C:
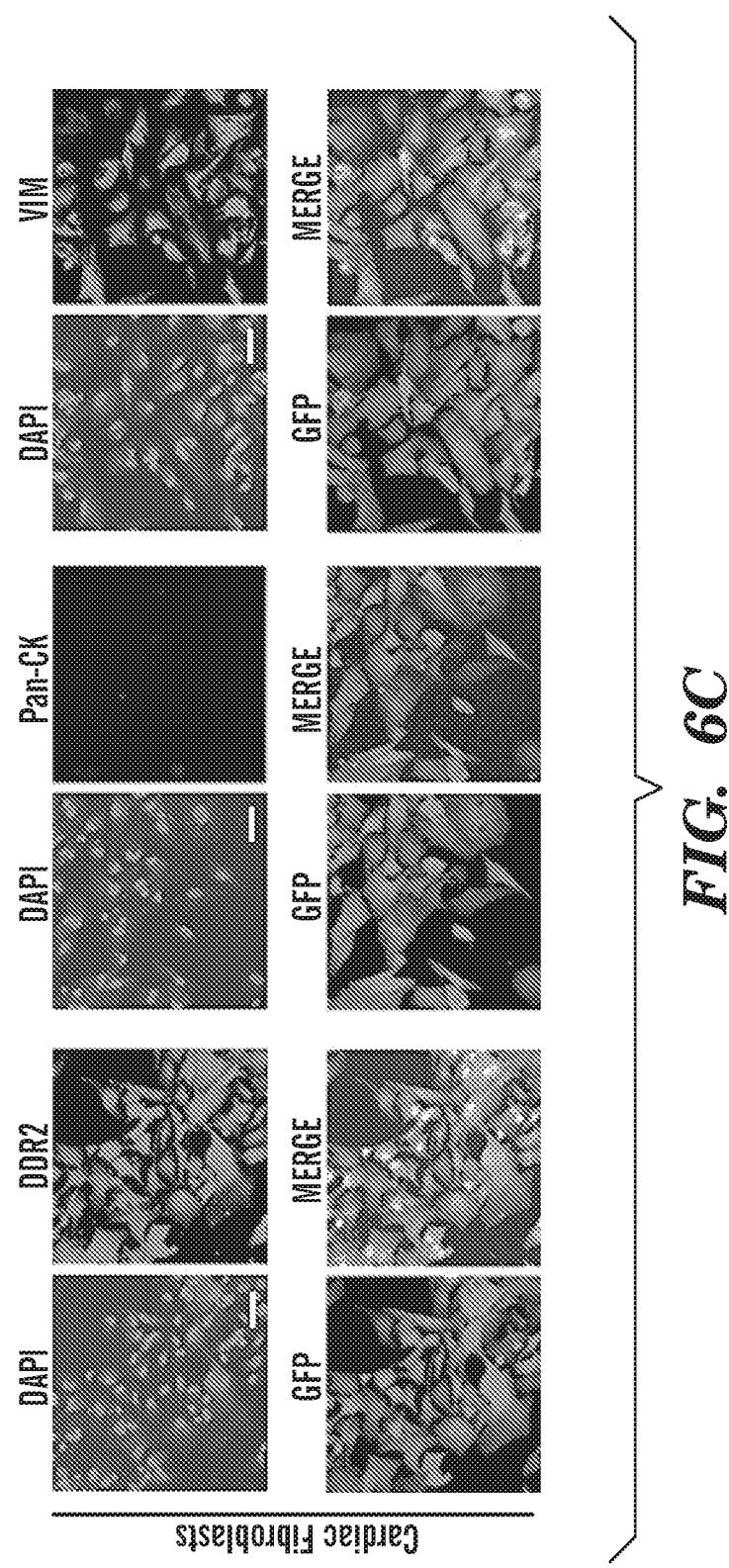
Figure 7A:
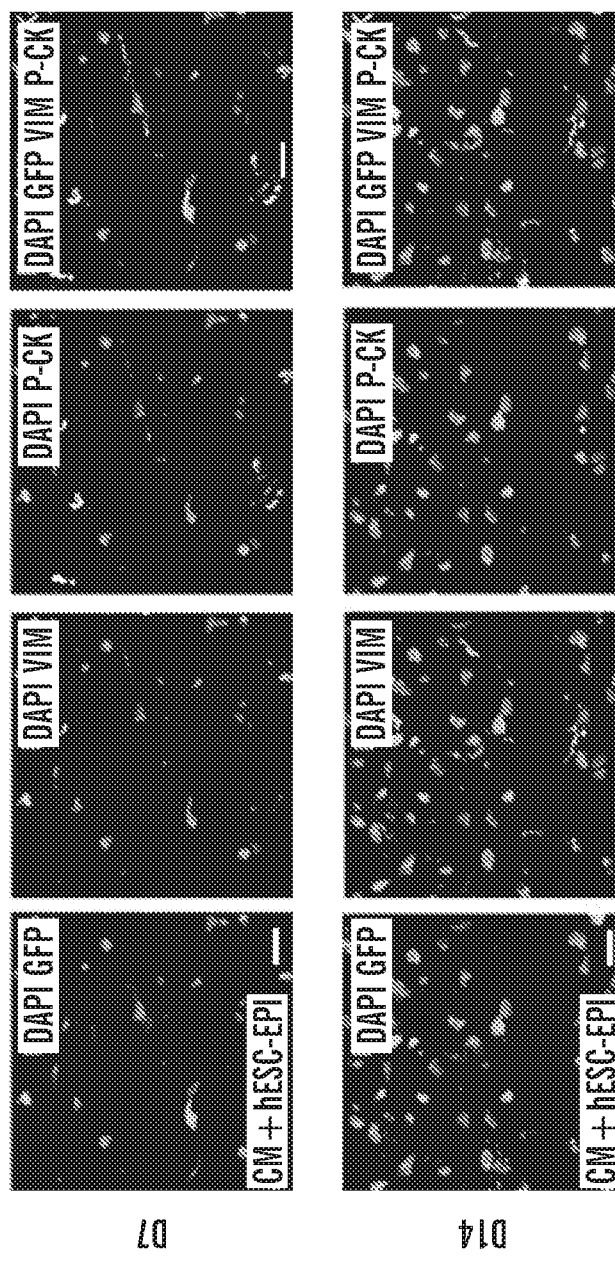
FIGS. 7A-7C. HESC-derived epicardial cells undergo EMT in 3D-EHT and promote electrical connectivity of hESC-derived cardiomyocytes.
Figure 7B:
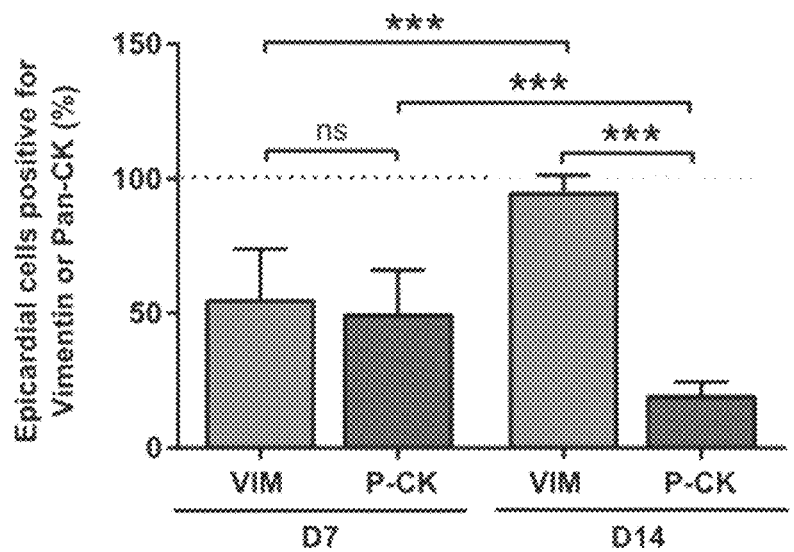
Figure 7C:
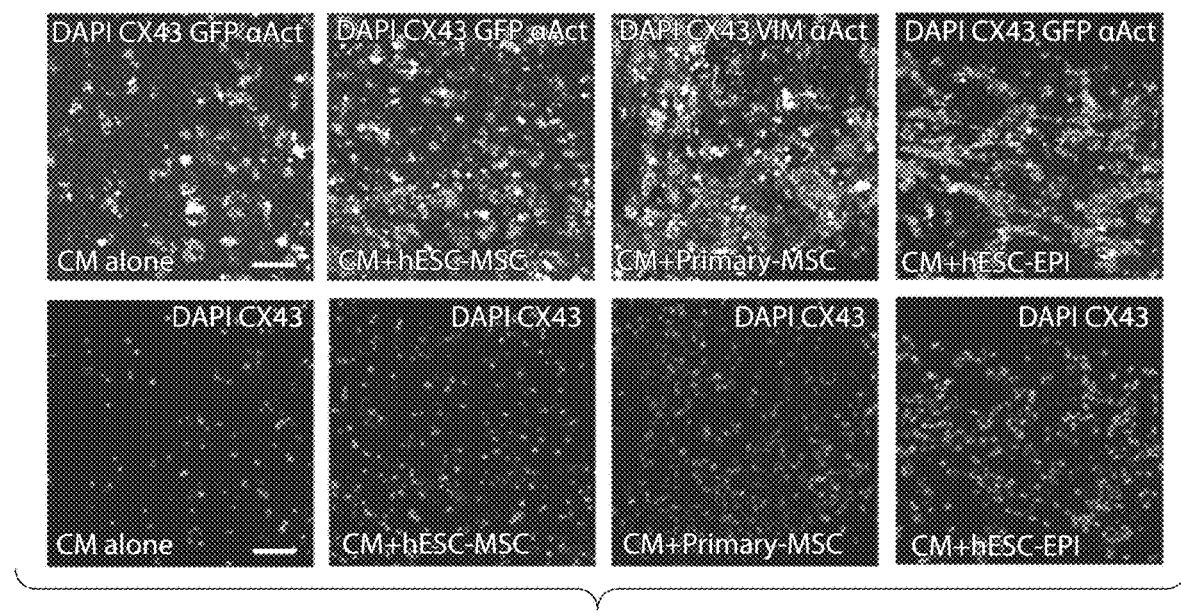

HESC-Derived Epicardial Cells Promote Cardiomyocyte Maturation in 3D-EHT hESC-derived GFP-transgenic epicardial cells and wild-type (WT) cardiomyocytes were generated as previously described (6, 10). Both epicardial cells, as well as cardiomyocytes, were generated at a high purity (94-97%). Cells were then incorporated into collagen-based 3D-EHTs, which developed for 14 days under passive stress before they were subjected to histological and functional assessment (FIGS. 1A-1D). The functionality of epicardial cells was first demonstrated through differentiating them to cardiac fibroblasts in vitro under chemically defined conditions. Epicardial cells expressed epicardial and epithelial markers (i.e., WT1 and pan-cytokeratin) but no mesenchymal markers after their derivation in vitro. At the end of the cardiac fibroblast differentiation protocol they expressed the fibroblast and mesenchymal markers, DDR2 and vimentin, but lost their epithelial character indicating successful epithelial to mesenchymal transition (FIGS. 6A-6C). To assess the potency of epicardial cells in 3D-EHT, the cells were compared with compositions containing cardiomyocytes alone, or cardiomyocytes and hESC-derived mesenchymal cells, or cardiomyocytes and primary mesenchymal cell types. Both epicardial cells as well as primary mesenchymal cells had the strongest effects on tissue remodeling and compaction, whereas tissues containing high-purity cardiomyocytes alone demonstrated a complete lack of compaction (FIGS. 1E, 1F). When in the tissues hESC-derived epicardial cells undergo EMT, as seen by the increase in expression of vimentin and decrease in pan-cytokeratin comparing constructs after 7 days and 14 days of their development (FIGS. 7A-7B). To determine the state of cardiomyocyte maturity, histological sections were stained for sarcomeric proteins and the sarcomere length was quantified. HESC-derived epicardial cells had the strongest effect on sarcomere length which correlates with cardiomyocyte maturation, compared to primary MSCs, hESC-derived MSCs or CM alone (FIGS. 1G-1H). Furthermore, constructs containing hESC-derived epicardial cells accounted for the most connexin 43 staining, a marker of electrical connectivity between cardiomyocytes, compared to the other groups (FIG. 7C). Taken together, these data indicate that hESC-derived epicardial cells replicate key steps of early embryonic heart development in 3D-EHTs resulting in increased cardiomyocyte maturation.

Functional Effects of hESC-Derived Epicardium in 3D-EHT

Figure 2A:
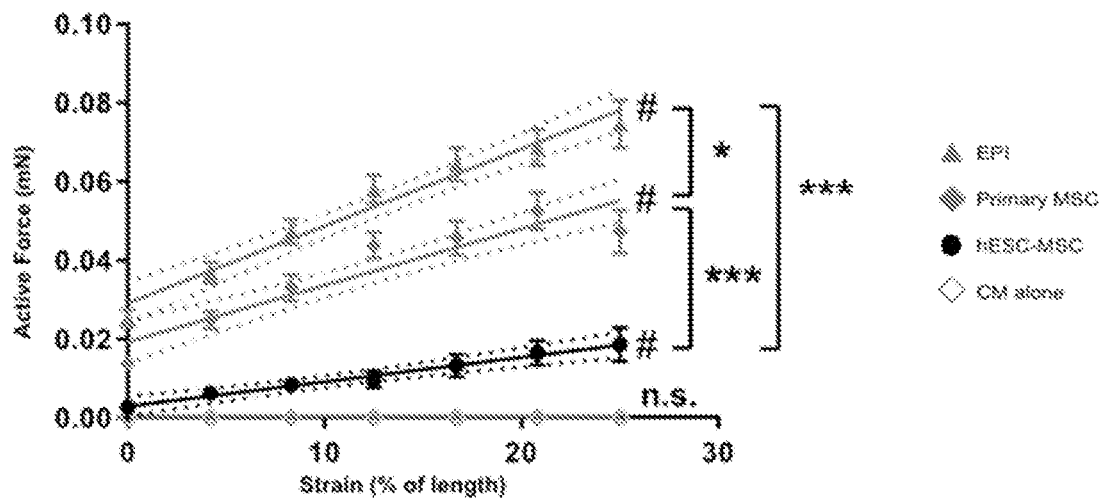
FIGS. 2A-2E. HESC-derived epicardial cells promote contractility and $Ca^{2+}$-handling of 3D-EHT.
Figure 2B:
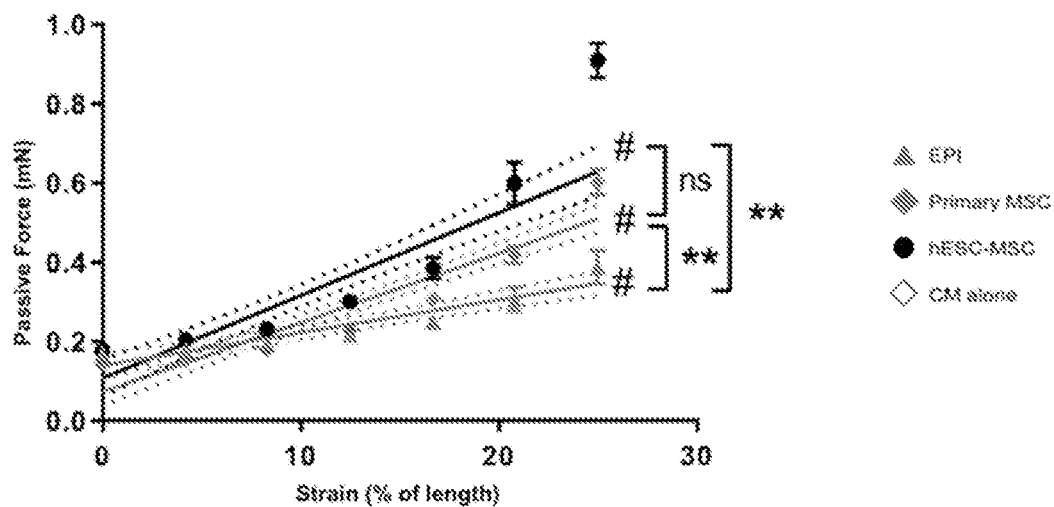
Figure 2C:
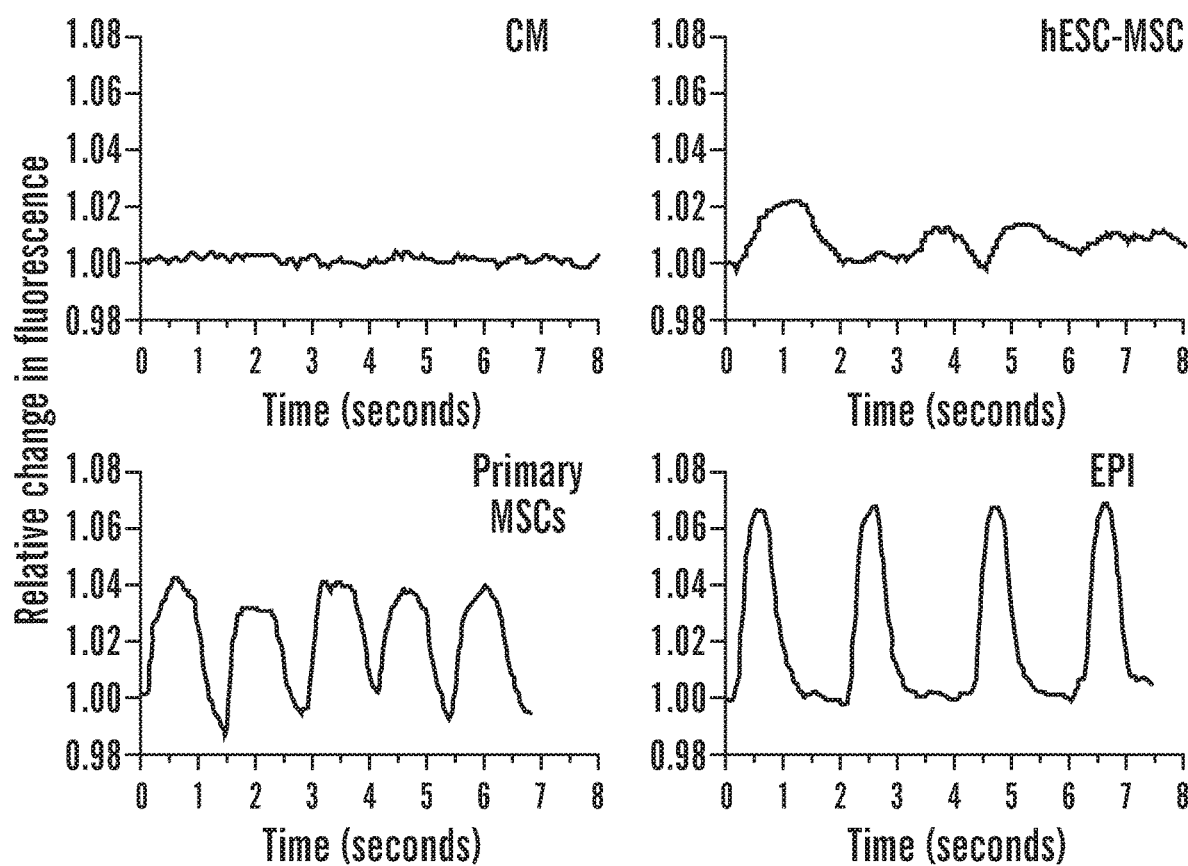
Figure 2D:
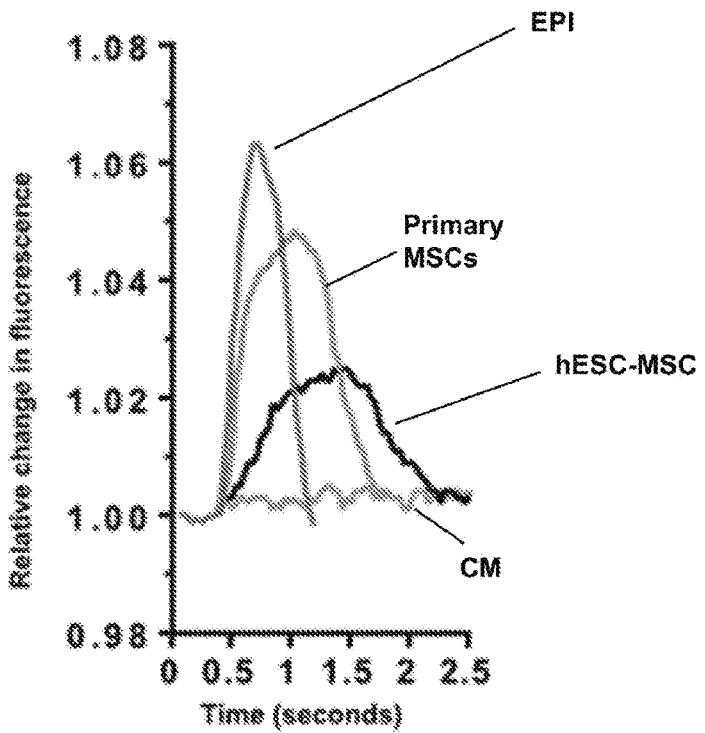
Figure 8A:
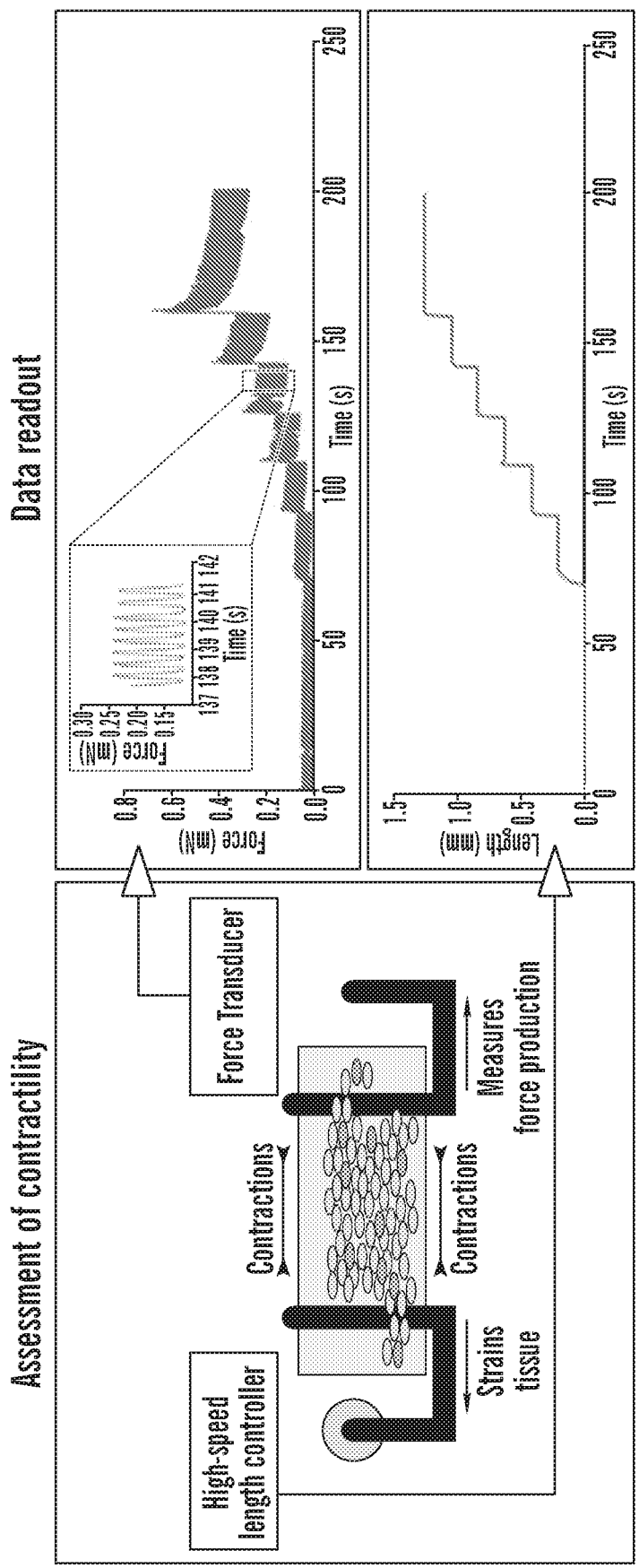
FIGS. 8A-8C. Functional characterization of 3D-EHT containing hESC-epicardial cells and cardiomyocytes.
Figure 8B:
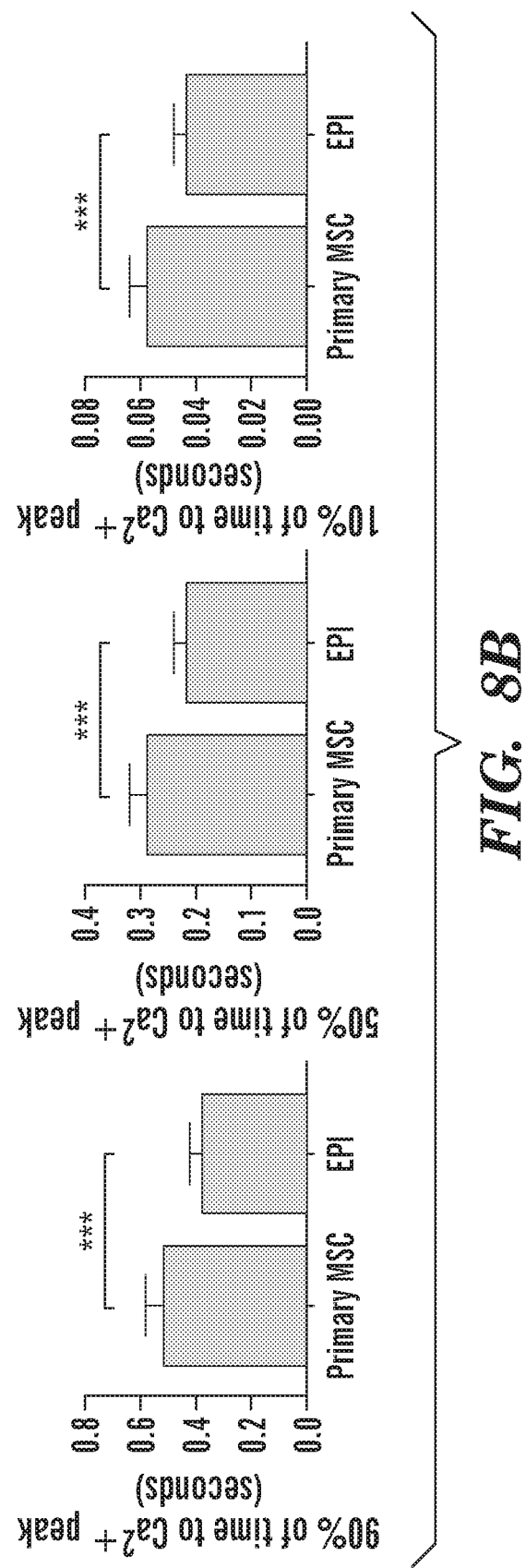
Figure 8C:
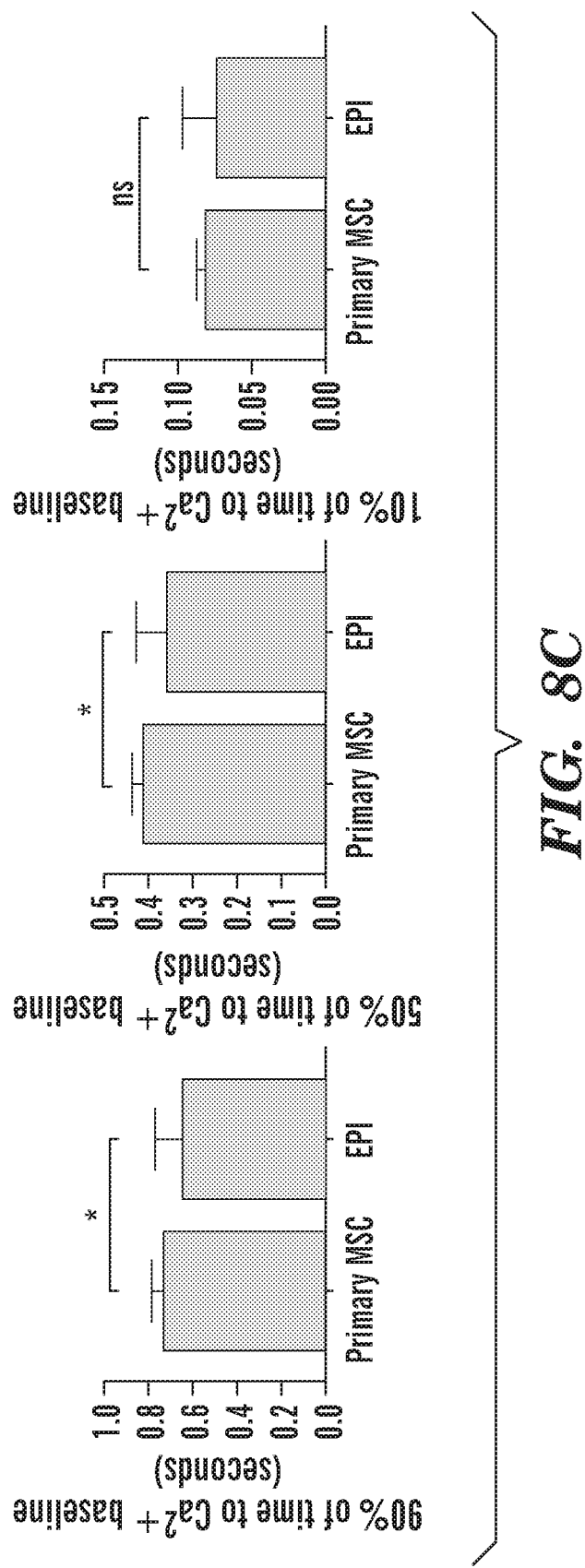

It was next tested whether the beneficial effects of hESC-derived epicardial cells observed histologically also translated to an increase in cardiac contractility. EHT constructs were transferred to a myograph with a length controller and a force transducer (FIG. 8A); constructs containing CM and either hESC-MSC or primary MSC or hESC-Epi exhibited a Frank-Starling relationship. In line with the histological finding that high-purity CM alone do not result in efficient tissue remodeling, cardiomyocyte maturation or electrical connectivity, coordinated contraction or measurable force production was not observed in 3D-EHTs containing CM alone. Constructs containing hESC-derived epicardial cells accounted for the greatest increase in active force production with increasing strain and produced most active force at each step in the strain regimen compared to primary MSCs and hESC-MSCs (FIG. 7A). At the same time 3D-EHTs containing hESC-Epi produced the least passive force compared to primary MSCs or hESC-MSCs, which would correspond to a more compliant tissue that may display better relaxation during diastole post transplantation in the infarct (FIG. 7B). When assessing the $Ca^{2+}$-handling of the constructs, those containing hESC-Epi and primary MSCs accounted for the most physiological signals. Constructs containing hESC-MSC displayed irregular and broad $Ca^{2+}$- waves while in those containing CM only no coordinated $Ca^{2+}$-waves were detectable at all. Rather, in the CM only group, uncoordinated contraction of single non-connected cardiomyocytes was observed (FIGS. 2C-2D). Constructs containing epicardial cells also accounted for steeper slopes of the $Ca^{2+}$-upstroke and shorter $Ca^{2+}$-upstroke times compared to primary MSCs (FIG. 2E; FIGS. 8B-8C). Taken together, these data indicate that hESC-derived epicardial cells promote functional maturation of 3D-EHT encouraging their use in vivo.

TABLE 1

Animal death after myocardial infarction and cellular engraftment.

| Parameter | EPI-Only | CM-Only | EPI + CM | Control |
|---|---|---|---|---|
| Animals that received cell injection | 15 | 15 | 15 | 13 |
| Acute death after myocardial infarction | 0 | 0 | 0 | 1 |
| Acute death after cell injection | 0 | 1 | 1 | 0 |
| Animals excluded prior to myocardial infarction | 0 | 0 | 0 | 1 |
| Animals included in the study | 15 | 14 | 14 | 013 |
| Overall mortality | 0/15 (0%) | 1/15 (6.6%) | 1/15 (6.6%) | 2/15 (13.3%) |
| Grafts present at 4 weeks | 10/10 | 8/9 | 9/9 | 0/8 |
| Grafts present at 12 weeks | 5/5 | 3/5 | 4/5 | 0/5 |

Engraftment and Fate in the Myocardial Infarct

Figure 9C:
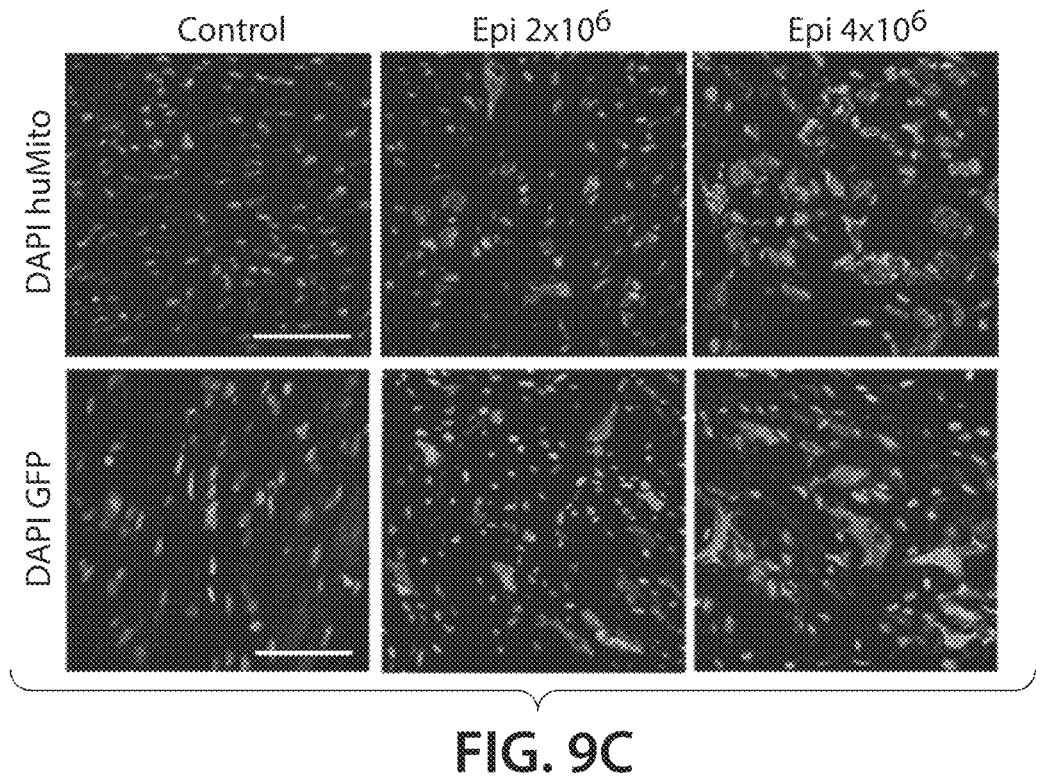
Figure 9D:
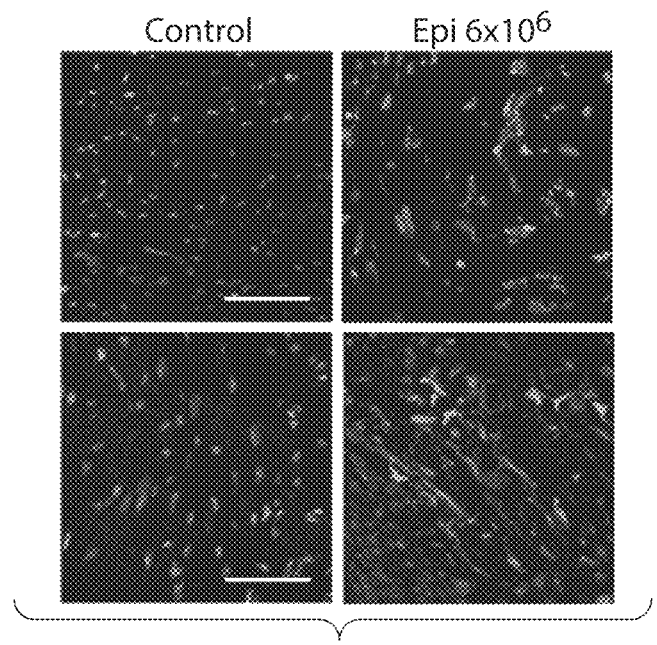
Figure 9E:
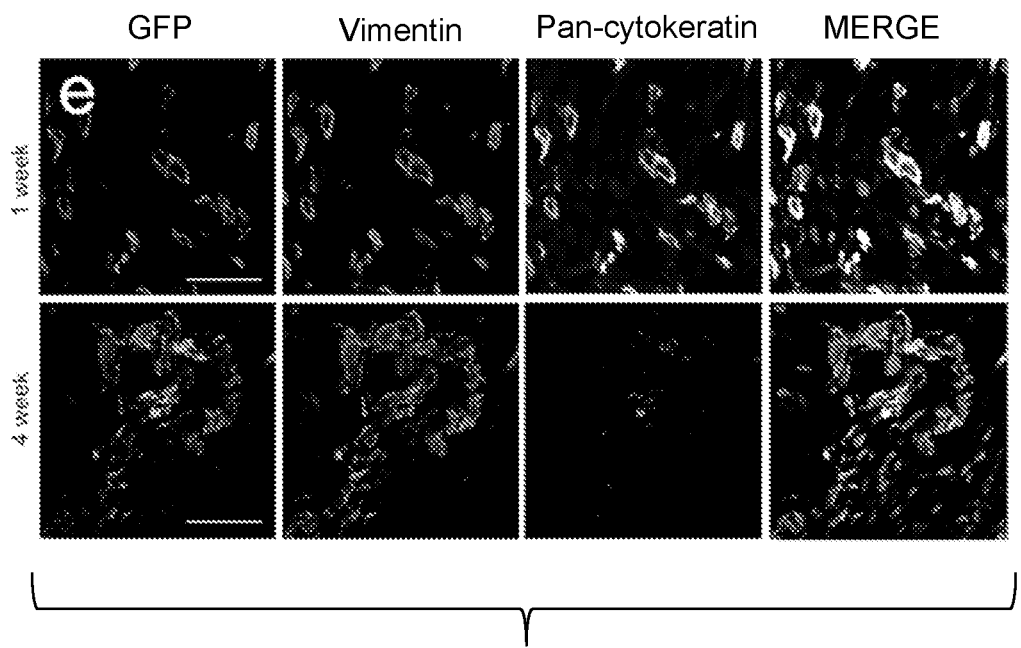
Figure 9F:
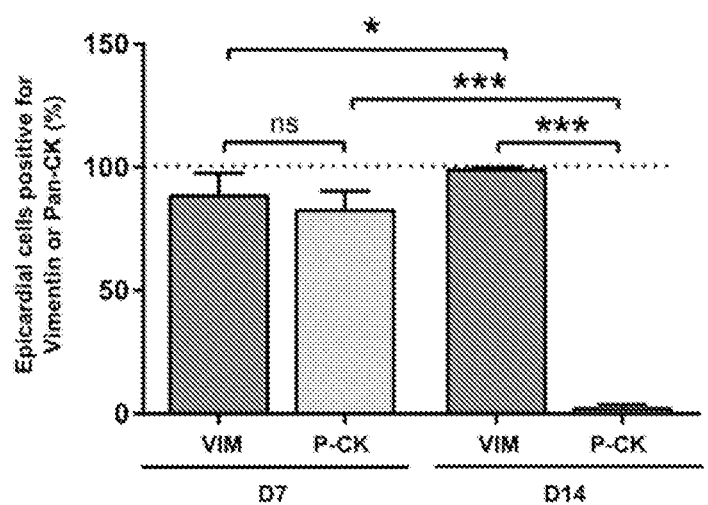
Figure 10A:
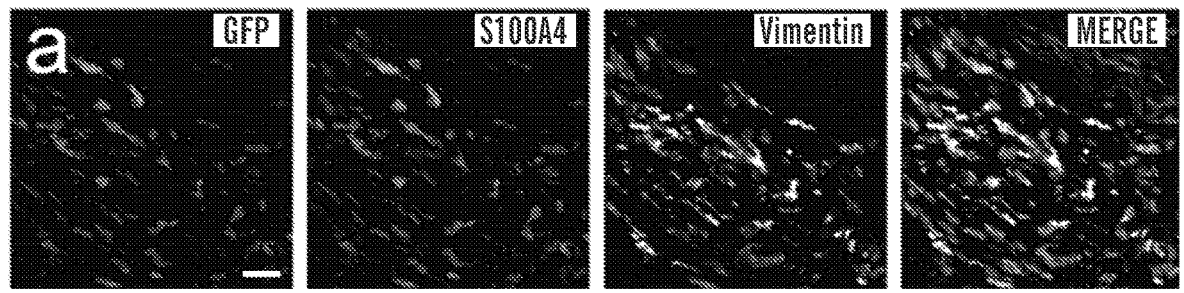
Figure 10B:
Figure 10C:

To assess the functional properties of hESC-derived epicardial cells in vivo it was first investigated whether epicardial cells survive transplantation and engraft in the infarct zone of athymic rats. Animals either received an intramyocardial injection of $2\times10^6$ (n=4) or $4\times10^6$ epicardial cells (n=4) or vehicle only (n=4) four days after 60 min ischemia in the left anterior descending territory. Grafted epicardial cells were readily detected at 7 days post-grafting with antibodies directed against GFP and human mitochondria. While a cell dose of $4\times10^6$ yielded robust grafts among all animals, a dose of $2\times10^6$ cells resulted in substantially smaller grafts and one animal without a detectable graft (FIGS. 9A-9C). In a second study, long-term engraftment was assessed and animals either underwent an injection of $6\times10^6$ epicardial cells (n=6) or a control injection (n=4). Four weeks post transplantation robust grafts were still detectable in the infarct zone (FIG. 9D). Comparing the expression of epithelial and mesenchymal markers of grafted epicardial cells at 7 days with the expression at 28 days post transplantation, it was found that EMT was ongoing but incomplete after 7 days and finally complete after 28 days with all grafted cells expressing Vimentin and almost no detectable expression of Pan-Cytokeratin (FIGS. 9E-9F). When assessing the fate of grafted epicardial cells, 28 days post-transplantation cells were found to be strongly positive for Vimentin and S100A4 suggesting a fibroblast phenotype. Only a small number expressed SMA but no significant integration into the wall of existing blood vessels was observed, corresponding to a myofibroblast phenotype (FIGS. 10A-10B). Grafted cells were negative for the cardiac marker α-Actinin and the endothelial marker human Lectin (FIG. 10D-10F). Taken together, these data indicate that hESC-derived epicardial cells form robust grafts in the infarct zone 28 days post transplantation and undergo EMT to a fibroblast phenotype.

Effects on Microvascular Density

Figures 2E, 3A:
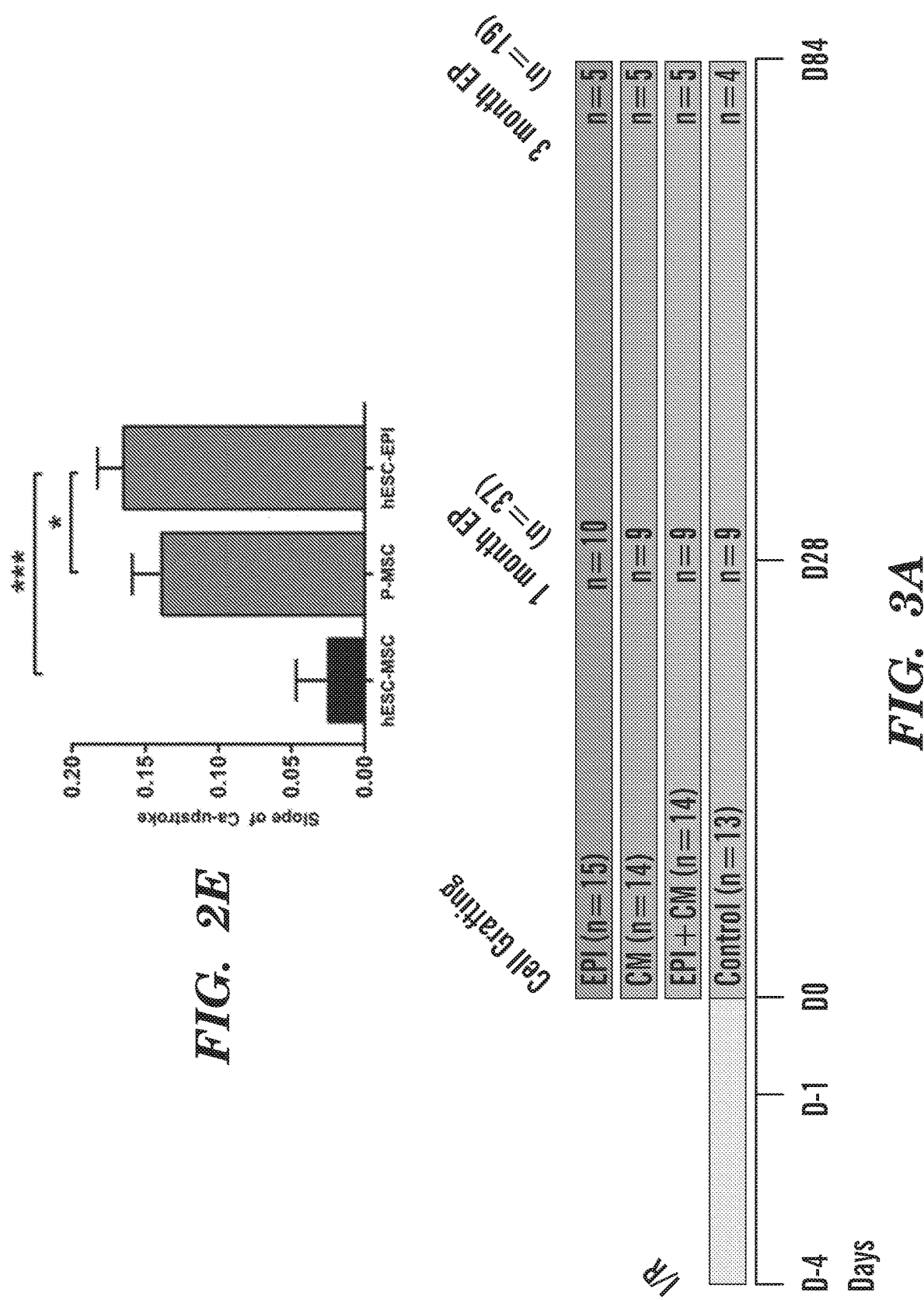
FIGS. 3A-3G. Co-transplantation of hESC-derived epicardial cells with cardiomyocytes promotes microvascular density.
Figure 3B:
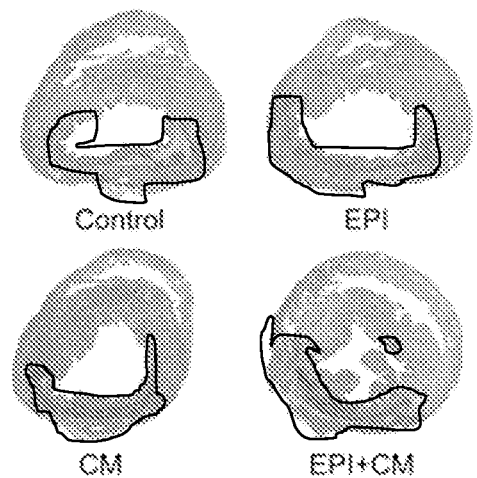
Figure 3C:
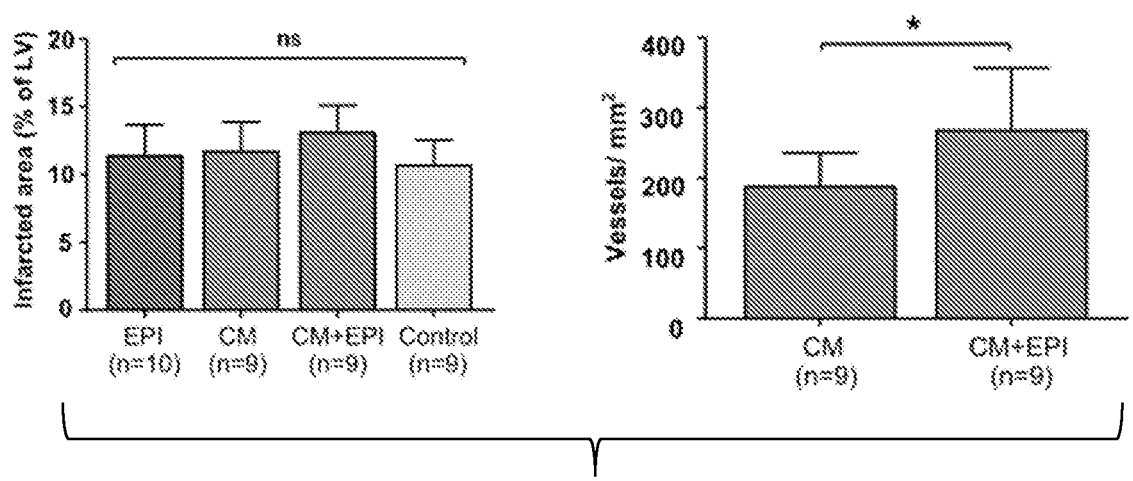
Figure 3D:
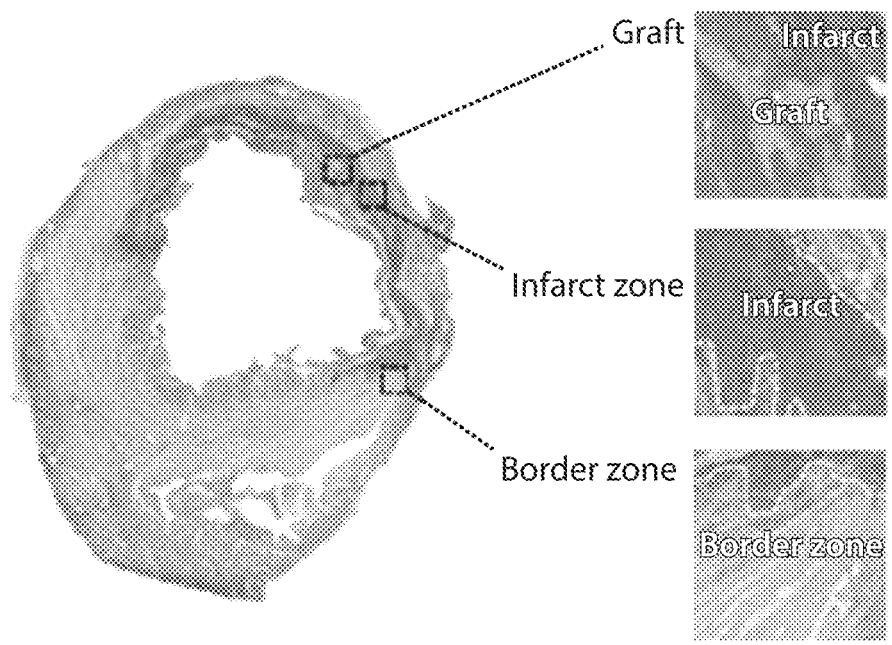
Figure 3E:
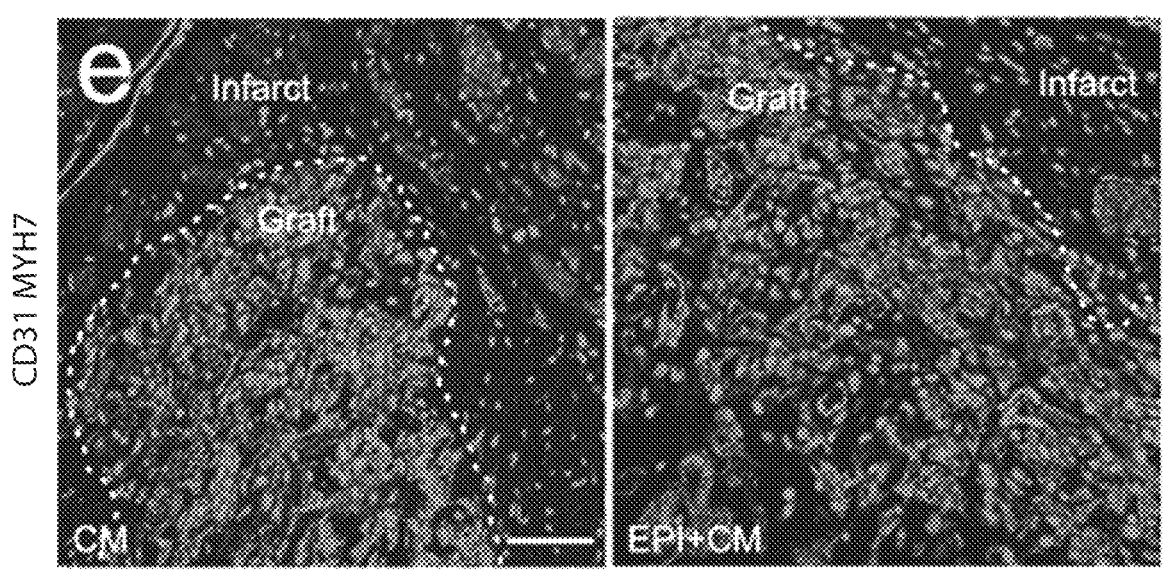
Figure 3F:
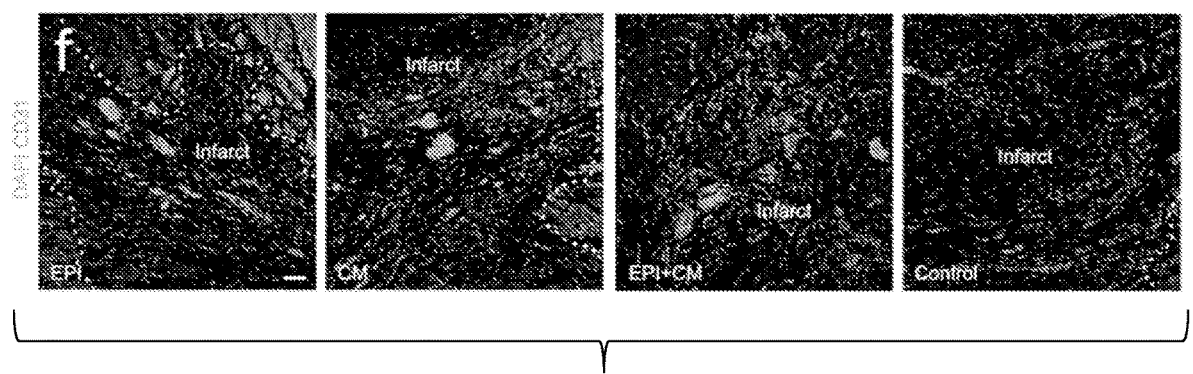
Figure 3F:
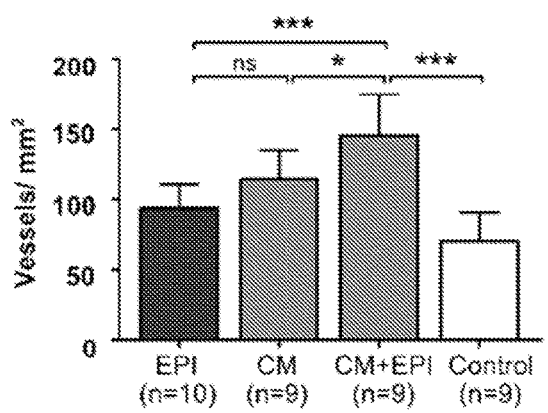
Figure 3G:
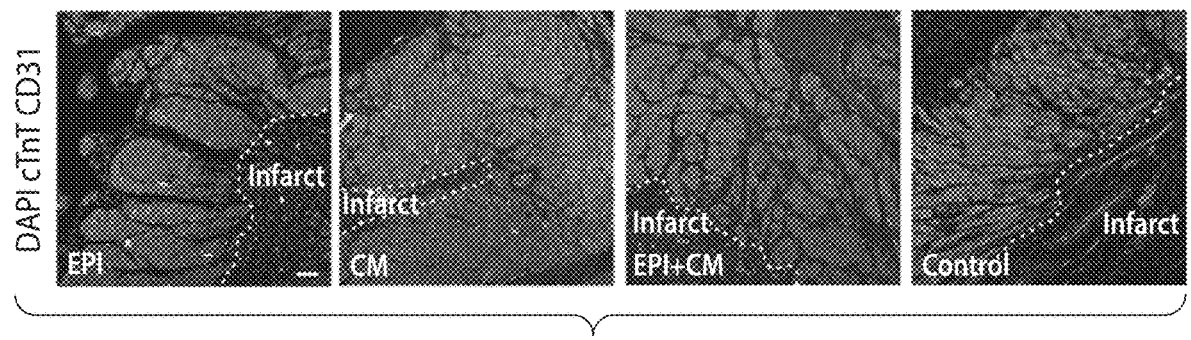
Figure 3G:
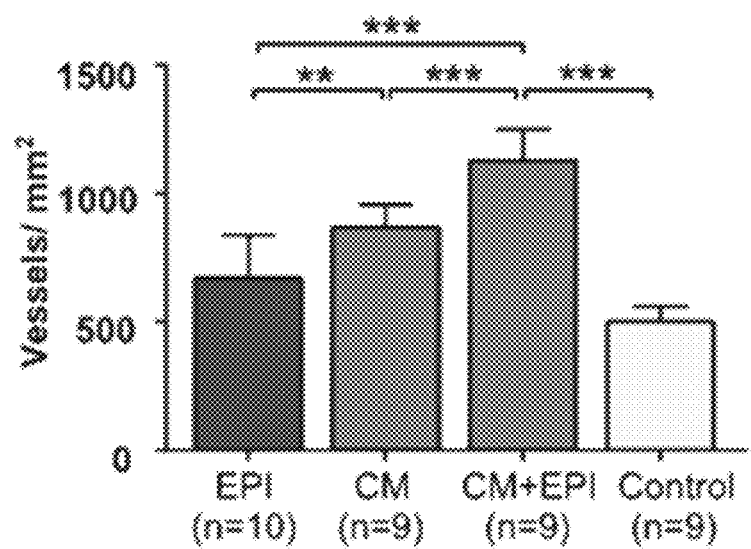
Figure 11A:
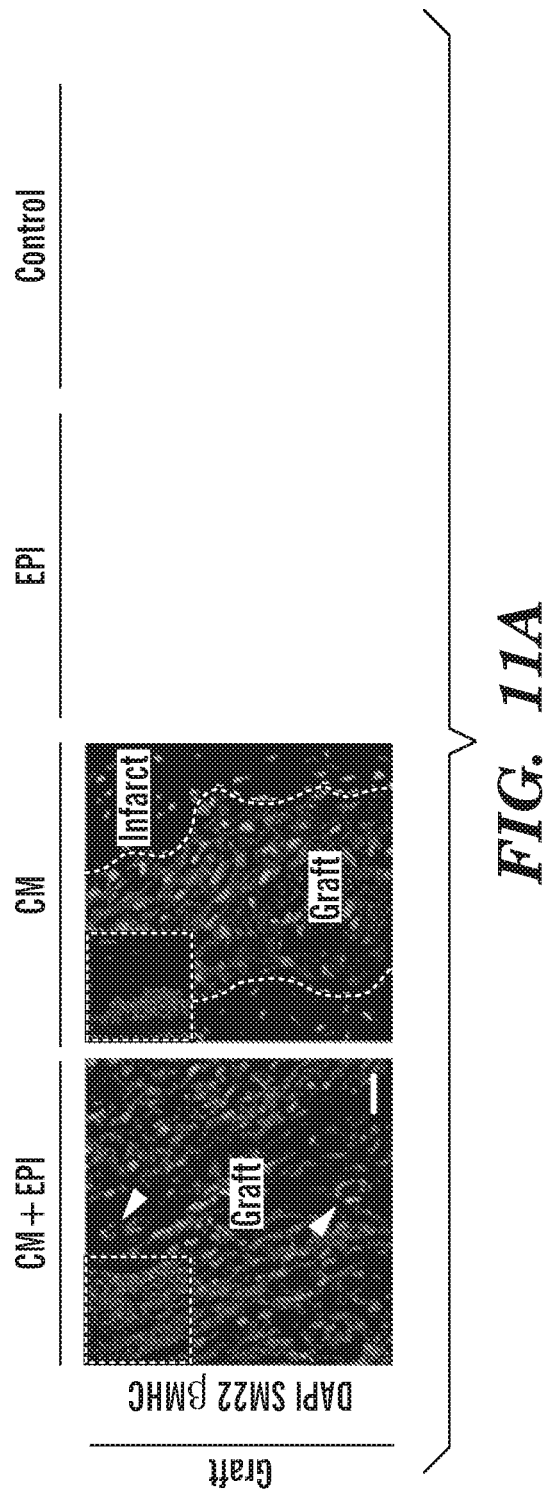
FIGS. 11A-11C. Presence of coronary arteries in cardiac grafts, infarct zone and border zone.
Figure 11B:
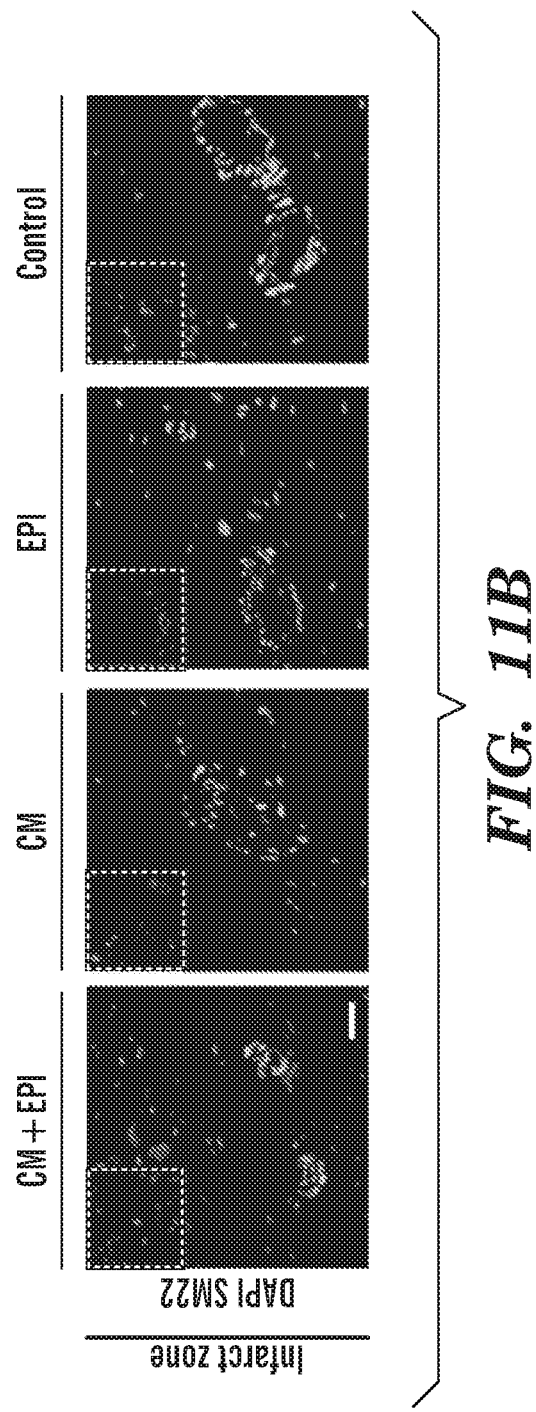
Figure 11C:
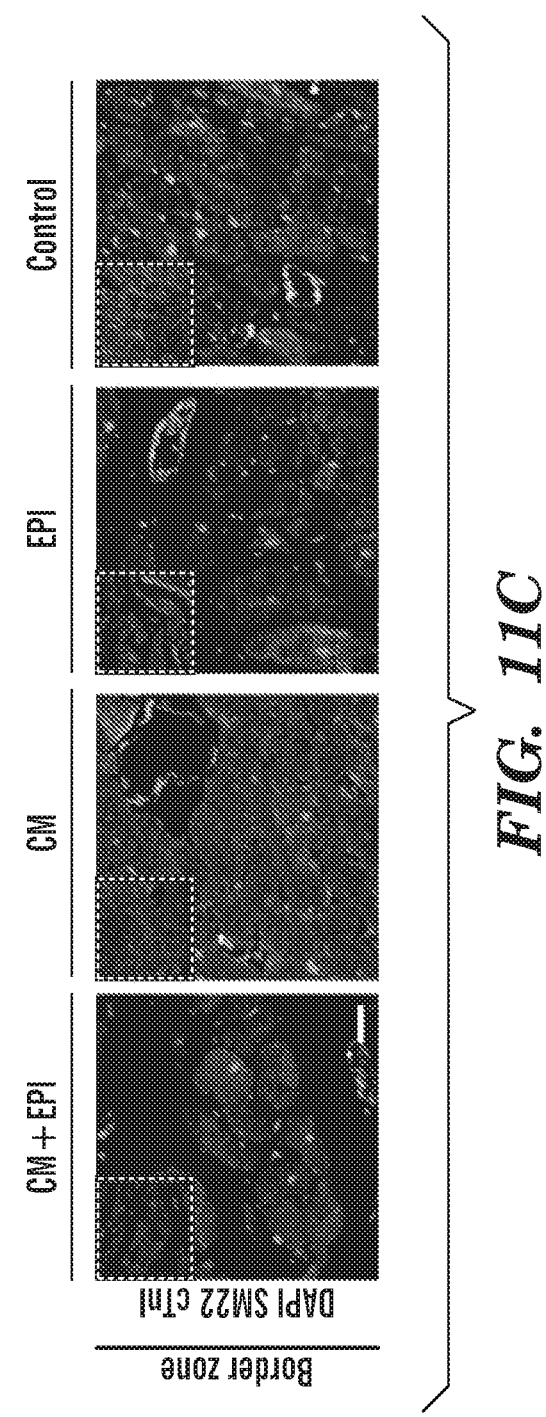

To assess whether hESC-derived epicardial cells exhibit a trophic effect similar to the one seen in embryonic heart formation, a co-transplantation study was performed. Animals either received an injection of $5\times10^6$ hESC-derived epicardial cells or $10\times10^6$ hESC-derived cardiomyocytes or the combination of both ($5\times10^6$ hESC-derived epicardial cells and $10\times10^6$ cardiomyocytes) or vehicle control (FIG. 3A). Four weeks post transplantation, no difference in infarct size was found between the groups, ruling out effects on infarct scar healing (FIGS. 3B-3C). To assess whether cell transplantation had an effect on host vessel recruitment the microvascular density in the cardiac grafts was quantified in the infarct zone and the non-injured border zone (FIG. 3D). Microvascular density was significantly increased in cardiac grafts of animals that were co-transplanted with epicardial cells and cardiomyocytes. Furthermore, the lumen of the vessels was perfused and erythrocytes were readily detectable (FIG. 3E). An increase in microvascular recruitment in the infarct zone and in the non-injured border zone of the infarct was observed, which was highest in EPI+CM, followed by CM, then EPI and finally vehicle control (FIGS. 3F-3G). To address the question of maturity of detected neo-vessels, three designated areas of interest were screened for the presence of smooth muscle cell coated arteries. Vessels containing mural cells were abundant in the infarct zone and the border zone of all groups. However, when assessing their presence within cardiac grafts smooth muscle cell coated vessels were observed in the EPI+CM group but not in the CM alone group, indicating epicardial effects on vascular maturation (FIGS. 11A-11C). In summary, hESC-derived epicardial cells create a favorable niche for cardiac grafts in a hostile environment, perhaps in part through an increase in vessel recruitment.

Co-Transplantation Promotes Cardiac Graft Size and Properties

Figure 4A:
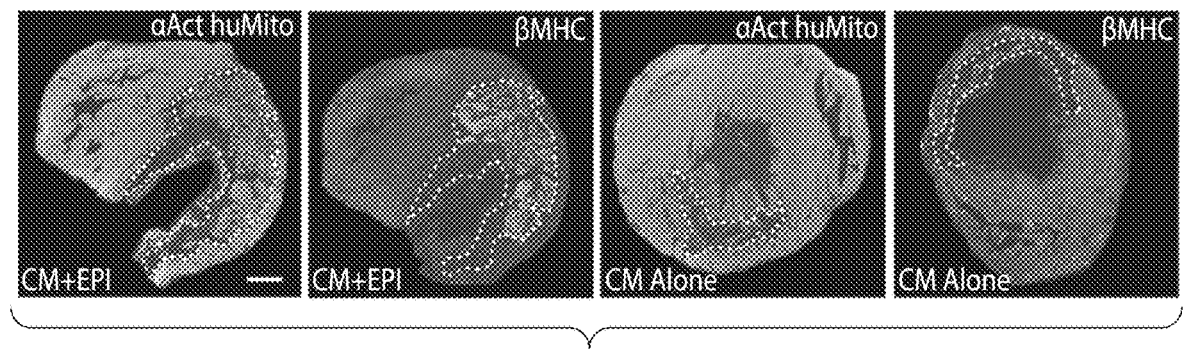
FIGS. 4A-4G. HESC-derived epicardial cells potentiate cardiac regeneration.
Figure 4B:
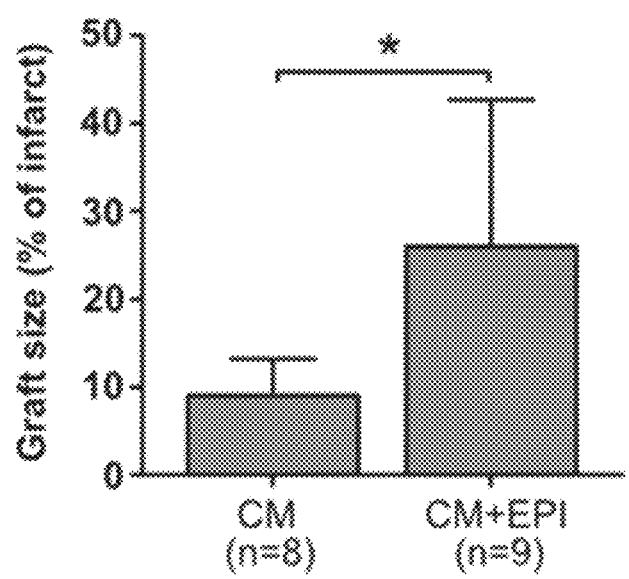
Figure 4C:
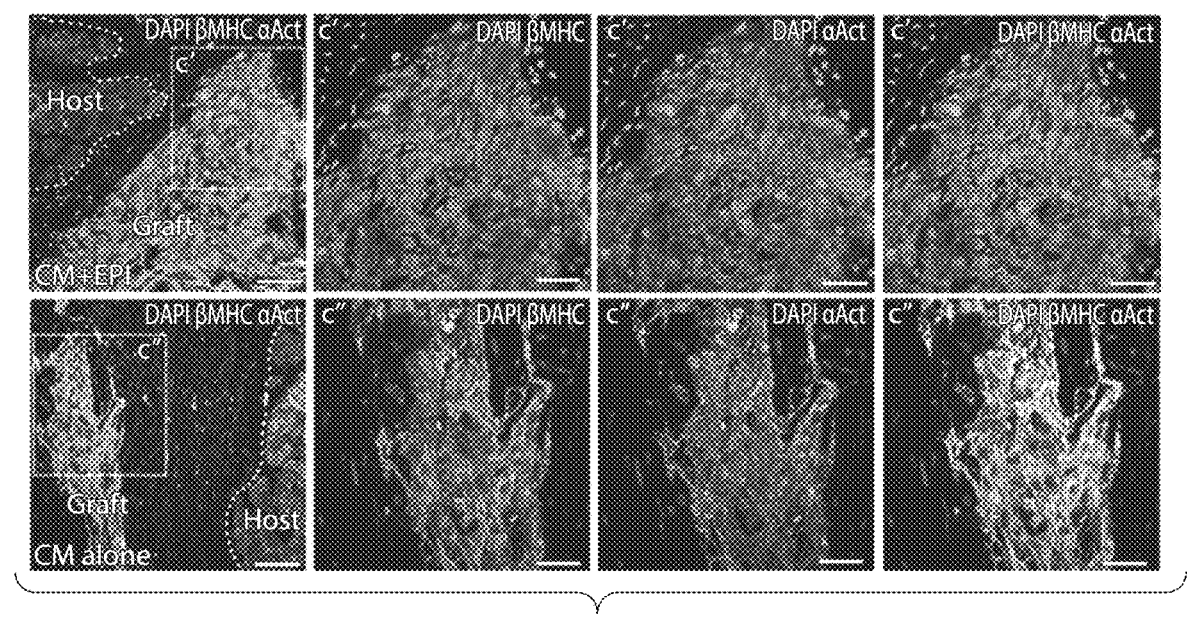
Figure 4D:
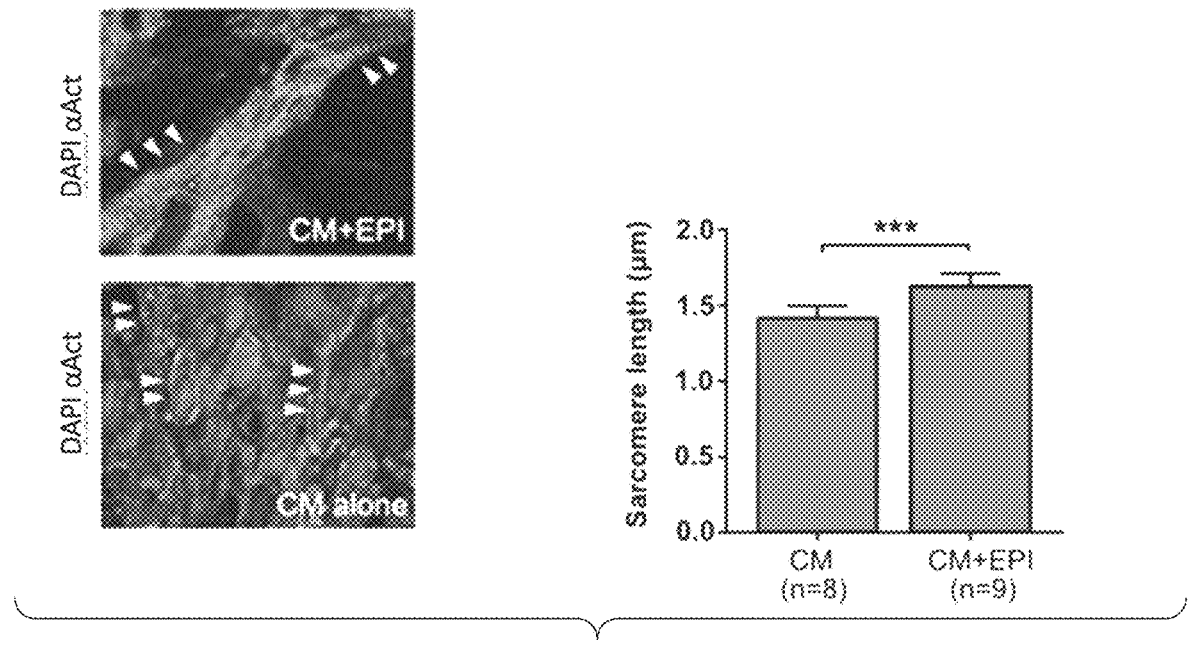
Figure 4E:
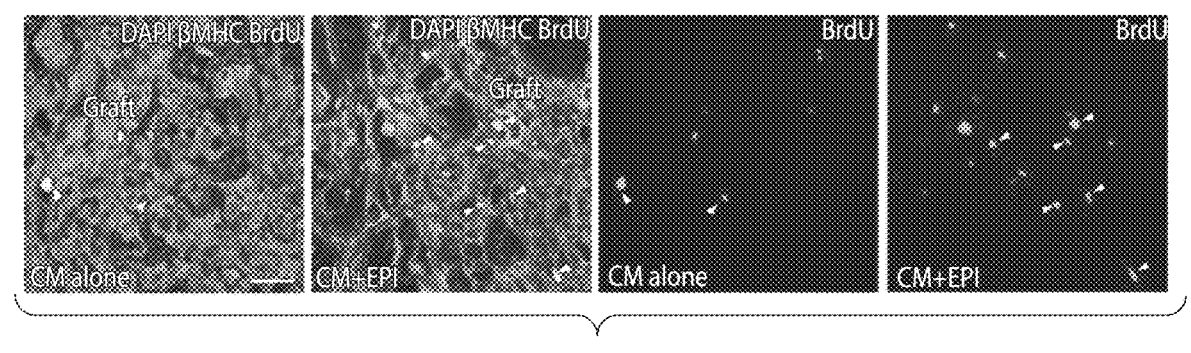
Figure 4F:
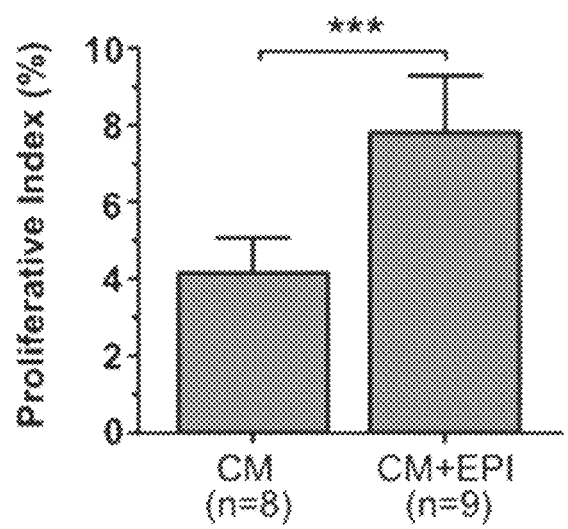

The effects of epicardial cells on cardiac graft were then assessed. Given the trophic effects of epicardial cells on cardiomyocytes in vitro and cardiac grafts in vivo it was first investigated whether this would affect cardiac graft size. Cardiac grafts were readily identified with antibodies directed against human mitochondria and α-Actinin or beta-MHC (i.e., expressed both α-Actinin and β-MHC). Cardiac grafts were found to be substantially larger if cardiomyocytes were co-transplanted with epicardial cells, compared to cardiomyocytes alone (FIGS. 4A-4C). Given the epicardial effects on cardiomyocyte maturation in vitro, the ultrastructure of the cardiac grafts was assessed. In line with these findings in vitro, cardiomyocytes that were co-transplanted with epicardial cells exhibited a greater sarcomeric length than those that were transplanted alone, being indicative of a more mature phenotype (FIG. 4D). To address whether epicardial cells would affect proliferation of cardiomyocytes within the grafts, tissue was stained with antibodies directed against the synthetic nucleoside BrdU and the human specific cardiac marker D-MHC. The proliferative index of D-MHC positive cells was higher in animals that received the combination of hESC-derived epicardial cells and cardiomyocytes compared with cardiomyocytes alone (FIGS. 4E-4F).

Figure 4G:
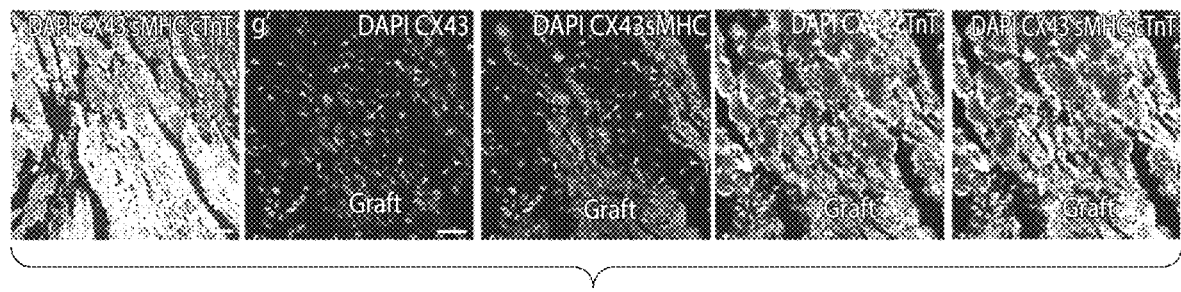

To address whether cardiac grafts were electrically connected with the host myocardium the tissue was stained with antibodies against β-MHC, α-Actinin and the electrical gap junction protein Connexin43. Potential electrical integrity was seen in several areas across all animals, demonstrated by Connexin43 expression between neighboring human and rat cardiomyocytes (FIG. 4G). In conclusion, hESC-derived epicardial cells promote cardiac graft size and properties such as maturation and proliferation and may improve electrical integration with the recipient myocardium.

Co-Transplantation Promotes Cardiac Function

Figure 5A:
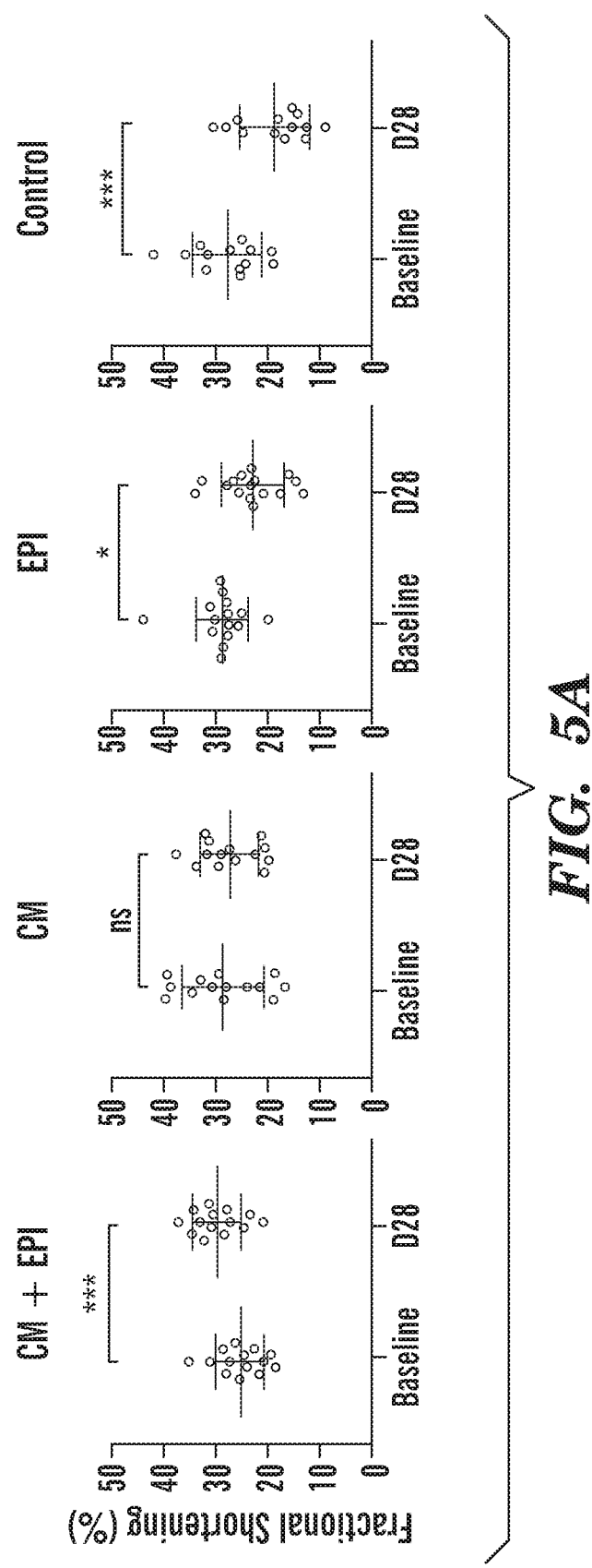
FIGS. 5A-5F. Co-transplantation of epicardial cells and cardiomyocytes promotes cardiac regeneration.
Figure 5B:
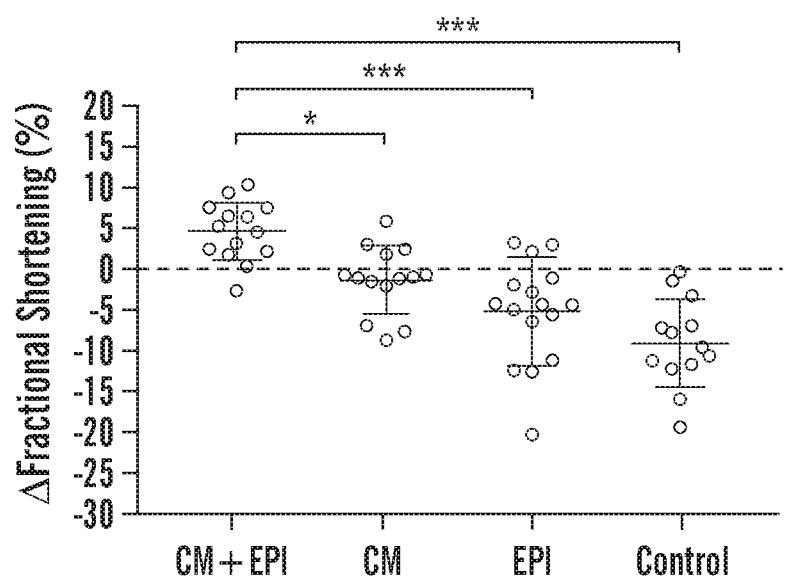
Figure 5C:
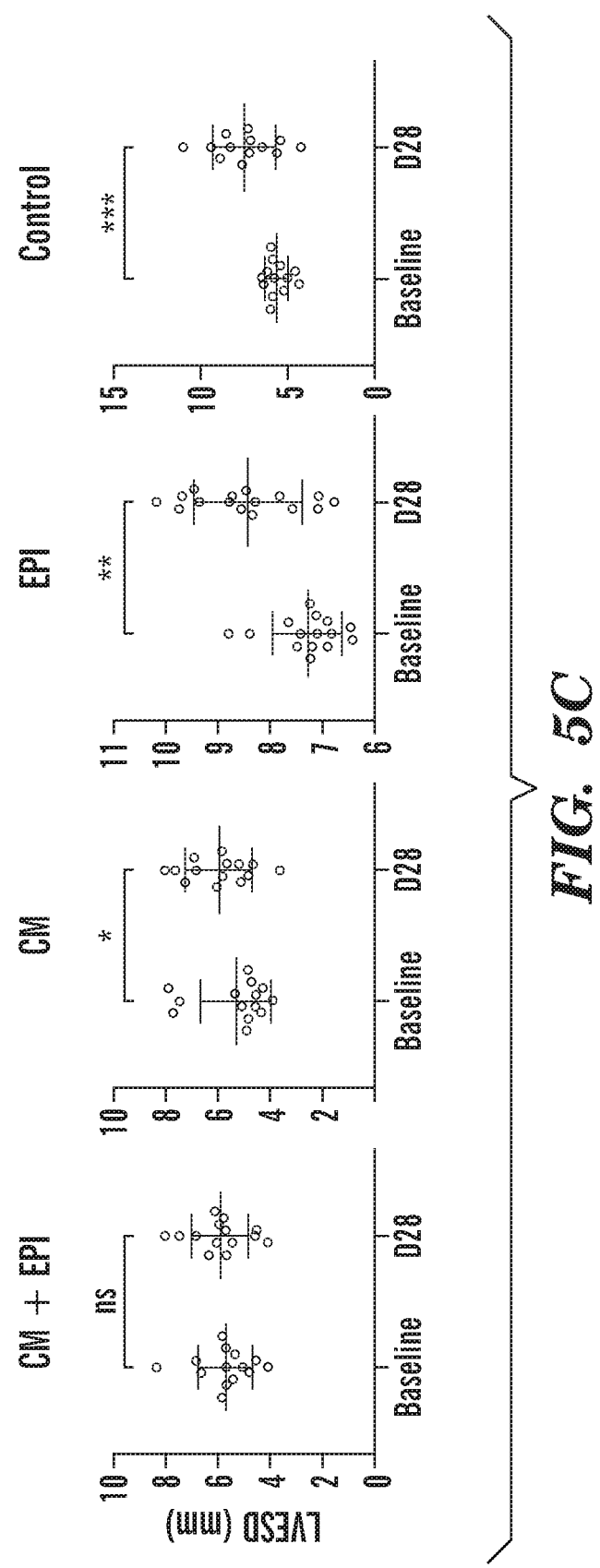
Figure 5D:
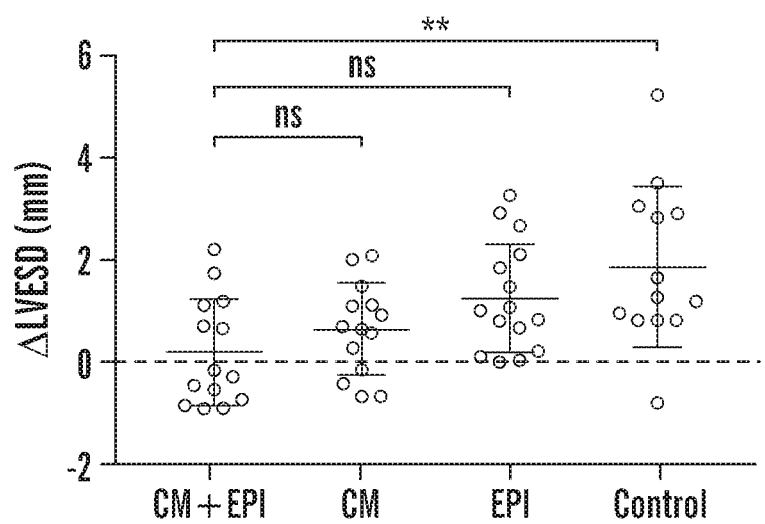
Figure 5E:
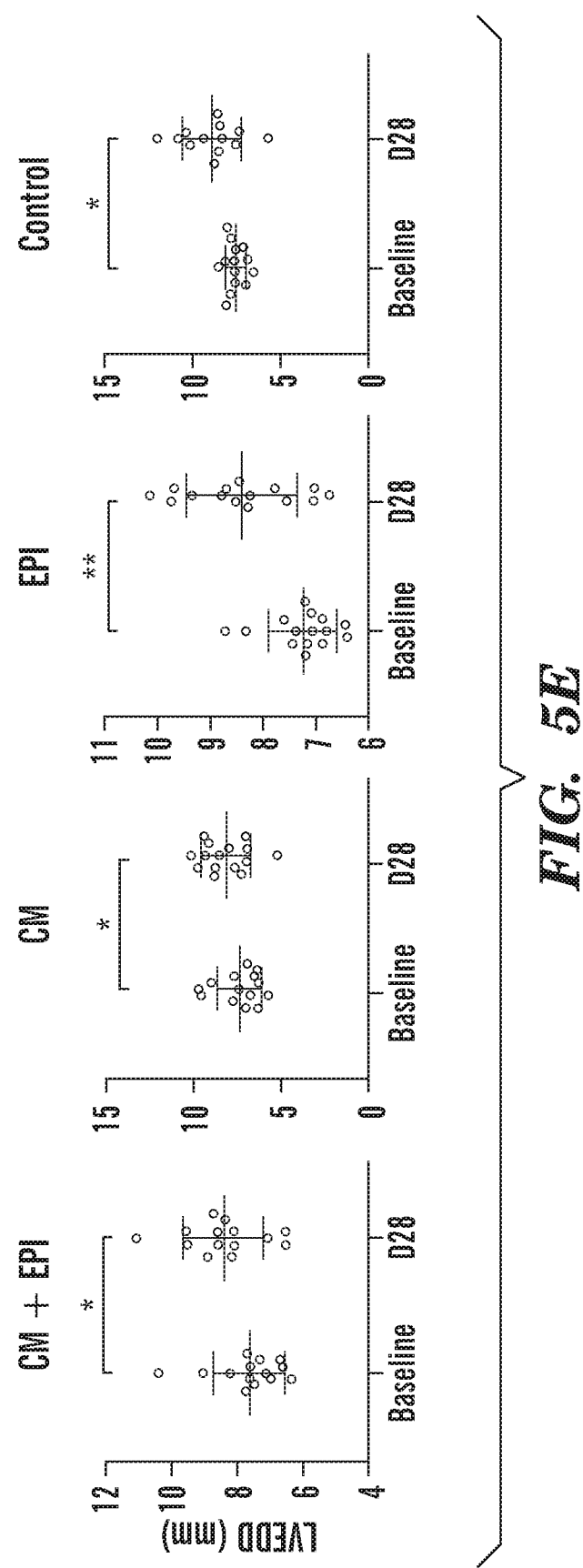
Figure 5F:
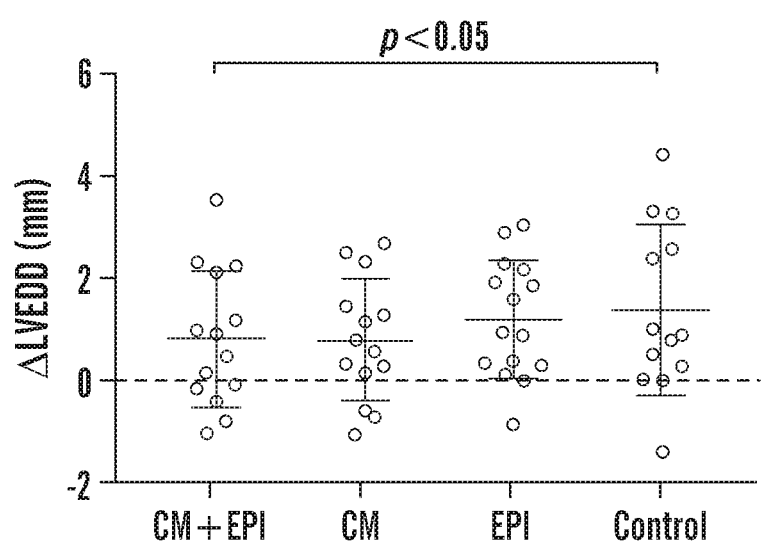

To assess the functional effects of cardiac grafts on global host heart function, cardiac ultrasound was performed on all animals prior to infarction, immediately before cell injection and after 28 days of follow-up. Compared with their pre-injection values, the vehicle control group displayed a decline in fractional shortening after injection, while the epicardial only group appeared to slow this process down. The CM only group preserved cardiac function and prevented further functional deterioration while the CM+EPI group led to an increase in function (FIGS. 5A-5B; Table 2). Left ventricular dilatation increased in all groups post infarction.

gested an overall group difference but post-hoc testing did not confirm this (FIGS. 5E-5F). Taken together, these data indicate that co-transplantation of hESC-derived epicardial cells with cardiomyocytes led to a greater increase in cardiac function compared to transplantation of cardiomyocytes alone.

Figure 12D:
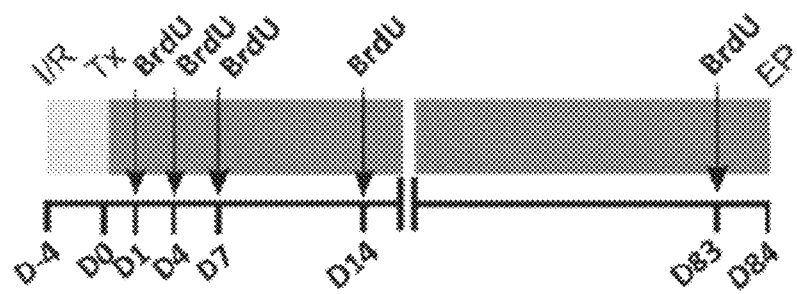
Figure 12E:
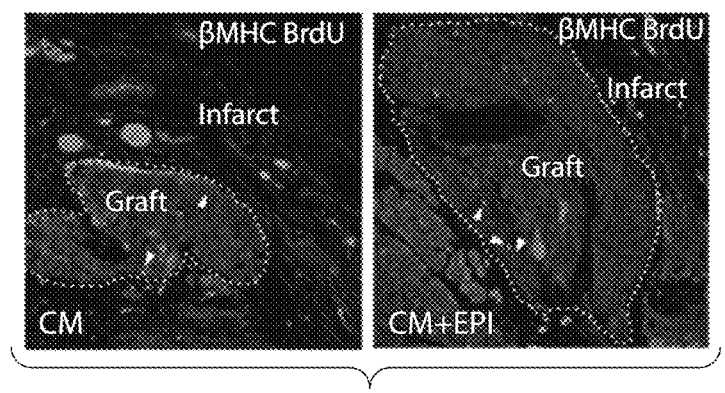
Figure 12F:
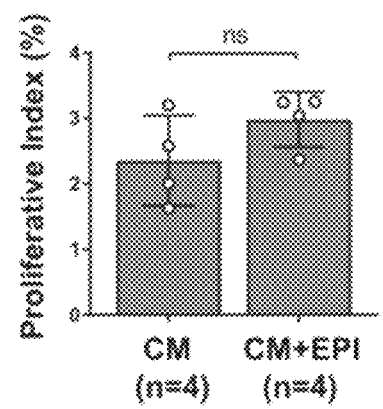

To investigate whether these effects would be present in the long term a subset of animals was followed for up for 3 months. Three months after cell grafting, hESC-derived epicardial cells as well as hESC-derived cardiomyocytes were still present in the infarct zone as confirmed by anti-human mitochondrial staining (FIGS. 12A-12B). In line with the 28-day follow-up, no differences were found in infarct size between the four study groups at 84-days post transplantation. (FIG. 12C). Furthermore, when assessing the proliferative index, cardiac grafts containing epicardial cells accounted for a non-significant trend of higher BrdU incorporation compared to animals that received cardiomyocytes alone (FIGS. 12D-12F). To summarize, although this study was not powered to detect functional differences at 3 months, hESC-derived cellular grafts persist in the long term. Given the graft persistence, it is specifically contemplated herein that the functional differences also persist at this time point.

It is demonstrated herein that hESC-derived epicardial cells augment hESC-derived cardiomyocyte maturation and function in vitro and in vivo, recapitulating their functional role in embryonic heart development. Previous studies have

TABLE 2

Histologic and echocardiographic parameters.

| Parameter | EPI-Only | CM-only | EPI + CM | Control |
|---|---|---|---|---|
| Histologic | | | | |
| Infarct area (% LV area) | 11.46 ± 0.7 | 11.77 ± 0.7 | 13.2 ± 0.6 | 10.75 ± 0.6 |
| Echocardiographic | | | | |
| Fractional shortening, 96 hours (%) | 28.8 ± 1.3 | 28.9 ± 2.0 | 25.3 ± 1.3 | 27.5 ± 1.8 |
| LVEDD, 96 hours (mm) | 7.2 ± 0.2 | 7.4 ± 0.3 | 7.6 ± 0.3 | 7.6 ± 0.2 |
| LVESD, 96 hours (mm) | 5.2 ± 0.2 | 5.3 ± 0.4 | 5.7 ± 0.3 | 5.5 ± 0.2 |
| Fractional shortening, 4 weeks (%) | 23 ± 1.4 #,* | 27.6 ± 1.5 | 29.7 ± 1.2 ### | 18.5 ± 1.9 ###, *** |
| LVEDD, 4 weeks (mm) | 8.4 ± 0.3 ## | 8.2 ± 0.4 # | 8.4 ± 0.3 # | 8.9 ± 0.5 # |
| LVESD, 4 weeks (mm) | 6.4 ± 0.3 ### | 5.9 ± 0.3 # | 5.9 ± 0.3 | 7.3 ± 0.5 ### |
| Fractional shortening, change from baseline (%) | −5.3 ± 1.7 *** | −1.3 ± 1.1 * | 4.5 ± 1.0 | −9.02 ± 1.5 *** |
| LVEDD, change from baseline (mm) | 1.1 ± 0.3 | 0.8 ± 0.3 | 0.8 ± 0.4 | 1.4 ± 0.4 |
| LVESD, change from baseline (mm) | 1.3 ± 0.3 | 0.6 ± 0.2 | 0.2 ± 0.2 | 1.9 ± 0.4 ** |

Abbreviations: EPI, epicardial cells; CM, cardiomyocytes; LV, left ventricle; LVEDD, left ventricular end-diastolic dimension; LVESD, left ventricular end-systolic dimension.
, significantly different versus paired 96 hr time point with $p < 0.05$;
, significantly different versus paired 96 hr time point with $p < 0.01$;
, significantly different versus paired 96 hr time point with $p < 0.001$;
*, significant difference from EPI + CM at same time point with $p < 0.05$;
**, significant difference from EPI + CM at same time point with $p < 0.01$;
***, significant difference from EPI + CM at same time point with $p < 0.001$.

Comparing pre- and post-injection values, left-ventricular end-systolic dimension (LVESD) remained stable in the CM+EPI group and increased in the CM only group, followed by greater increases in the EPI and the vehicle control group. The change in LVESD in the CM+EPI group was significantly smaller than in the vehicle control group but the difference to the CM only group or the EPI group did not reach statistical significance (FIGS. 5C-5D). For left ventricular end diastolic dimension (LVEDD) ANOVA sugdemonstrated that hESC-derived cardiomyocytes can remuscularize the mammalian infarct and preserve cardiac function (6). At the same time a detailed understanding of embryonic heart development has highlighted the trophic role of the epicardium, while in vitro studies using hPSCs have enabled chemically defined derivation of this essential embryonic tissue (10, 11). Exploiting these developmental insights can help to optimize current cardiac regeneration strategies by providing an adjunctive therapy for hESC-derived cardiomyocyte transplantation.

The data provided herein show that co-culture of hESC-derived epicardial cells and cardiomyocytes results in compaction and structural, as well as functional, maturation of 3D-EHT. More specifically, it is demonstrated herein that hESC-derived epicardium outcompetes both hESC-derived as well as primary MSCs in terms of force generation and $Ca^{2+}$-handling, corroborating the functional role of its embryonic identity. The functional potency of epicardial cells may prove broadly applicable to current tissue engineering strategies, that would benefit from enhanced structural integrity and function of cardiomyocytes (25).

Linked to its key role in development, the epicardium also becomes re-activated and proliferative following cardiac injury. In the adult mammalian heart the epicardial response to injury is inadequate to effect cardiac repair, as evidenced by the poor regenerative capacity of adult myocardial tissue following cardiac injury. In contrast, neonatal mouse and zebrafish hearts are capable of cardiac regeneration and the epicardium plays a critical role in this process (26, 27). Hence, the embryonic identity or state of exogenous hESC-derived epicardium may be of functional relevance. In this context it has been demonstrated that embryonic cardiac fibroblasts induce greater cardiomyocyte proliferation than their adult counterparts, which cause cardiac hypertrophy, providing further evidence that the embryonic origin might be instructive for regeneration (20). The data herein show that upon transplantation in the infarct the epicardium gives rise primarily to cardiac fibroblasts, which is in line with previous work confirming the epicardial origin of fibroblasts in the injured myocardium (28, 29). Moreover, the increase in proliferation of grafted cardiomyocytes as well as their subsequent maturation induced by the hESC-derived epicardium further confirms that the transplanted epicardium reprises its embryonic role in vivo. Indeed, incomplete maturation of the hESC-epicardium at the time of transplantation, consistent with the finding that nearly all cell types derived from hESCs display an immature or fetal phenotype, may be beneficial for optimal support of transplanted hESC-cardiomyocytes.

Epicardial cells thus allow for formation of larger cardiac grafts that are also better vascularized. This is of particular interest as the hostile post-infarct environment results in high cell death and low engraftment rates, which constitute a long-standing intricacy in heart regeneration endeavors. Ultimately superior graft integrity and size also translate to an increase in cardiac function, compared to cardiomyocytes alone.

The observed effects raise the question by which mechanisms they occur. Without wishing to be bound by theory, one direct explanation is that epicardial cells exert pro-proliferative and pro-survival effects on co-transplanted cardiomyocytes resulting in larger grafts, which generate more force. Furthermore, the observed increase in the recruitment of host neo-vessels might combine with these effects and further improve cell survival. It has been shown that endothelial cell secreted factors such as neuregulin and nitric oxide reduce cardiac cell death upon injury (30, 31). Additionally, a vascular supply is critical for optimal graft function and its maintenance on the long-term.

Without wishing to be bound by theory, another factor that might benefit cardiac graft survival and maturation is the provision of extracellular matrix by epicardial cells. It has been demonstrated that the secretion of fibronectin by epicardial cells is required for heart regeneration in zebrafish (32). In line with these findings, it was demonstrated that the orchestrated secretion of fibronectin, collagen and heparin-binding EGF-like growth factor by embryonic but not adult fibroblasts resulted in cardiomyocyte proliferation (20). Hence, without wishing to be bound by theory the matrix laid down by hESC-derived epicardial cells is likely to exhibit developmental cues that are absent in mature post-infarct myocardium, providing an advantageous niche in a hostile environment.

Cardiovascular regenerative medicine has made substantial progress but certain limitations remain. Pioneering efforts have allowed for cardiomyocyte survival sufficient to remuscularize infarcted rodent and non-human primate hearts entailing rescue of, or even increase, in left ventricular systolic function (6, 13, 14). Nevertheless, hPSC-derived cardiomyocyte transplantation is hampered by low proliferation rates, cellular immaturity and graft size. The data in this study indicate that hESC-derived epicardial cells are a promising tool to critically catalyze progress to overcome these limitations, by promoting cardiomyocyte proliferation, maturity, graft size and ultimately cardiac function. In support of these findings it has been demonstrated that human primary epicardial cells promote cardiac function compared to vehicle control and that co-transplantation of cardiovascular progenitors with epicardial cells exerts a synergistic effect that exceeds that of monotherapy (33, 34). While these results suggested a beneficial effect of poly-cell therapy, the authors did not detect grafts in any of the groups, suggesting that the effects seen were only paracrine in nature. Similarly, co-transplantation of endothelial cells, smooth muscle cells and cardiomyocytes in addition to an epicardial IGF-1 loaded fibrin patch displayed a synergistic effect on systolic heart function in a swine model of myocardial infarction (35). In contrast, the grafts observed in the experiments described herein, both cardiac as well as epicardial, were detectable up to three-months post transplantation, providing evidence for longevity and likely perpetuation of benefits in the long term.

hESC-derived epicardial cells are a promising tool to advance regenerative cardiovascular medicine, including cell transplantation as well as tissue engineering strategies.

Methods

Preparation of hESC-Derived Epicardial Cells and hESC-Derived Cardiomyocytes.

Epicardial cells were differentiated from GFP-transgenic hESCs as previously described (10). Briefly hESCs (H9, WiCell, Madison) were maintained in a chemically defined medium (CDM-BSA) containing Activin-A (10 ng/ml, R&D Systems) and FGF2 (12 ng/ml, R&D Systems). Chemically defined medium consisted of IMDM (250 ml, Life Technologies), Ham's F12 (250 ml, Life Technologies), Pen/Strep (5 ml, Life Technologies), Insulin (350 µl, Roche), Transferrin (250 µl, Roche), chemically defined 100× lipid concentrate (5 ml, Life Technologies) and monothioglycerol (20 µl, Sigma). Differentiation to lateral mesoderm was performed as previously described in CDM-PVA, containing polyvinyl alcohol (PVA, 1 mg/ml, Sigma)(14). In brief, early mesoderm differentiation was started with a combination of CDM-PVA, FGF2 (20 ng/ml), LY294002 (10 µM, Sigma) and BMP4 (10 ng/ml, R&D) for 1.5 days. Then, lateral mesoderm differentiation was started in CDM-PVA, FGF2 (20 ng/ml) and BMP4 (50 ng/ml) for 3.5 days. To induce epicardial differentiation, cells were resuspended as single cells in CDM-PVA, Wnt3a (25 ng/ml, R&D), BMP4 (50 ng/ml) and RA (4 M, Sigma) at a seeding density of $2.5 \times 10^4/cm^2$ for 10 days and the medium was changed half-way through the differentiation. For derivation of mesenchymal stem cells from hESCs, colonies were passaged, resuspended in CDM-PVA containing FGF (12 ng/ml) and SB (10 M) and seeded at a density of 30 colonies/cm² of a gel-MEF coated plates. Cells were enzymatically dispersed and passaged 4 times in CDM-PVA, containing FGF and SB before being split one more time in DMEM-F12 containing 10% fetal bovine serum for long-term maintenance. Primary mesenchymal stem cells were also maintained in DMEM-F12 containing 10% fetal bovine serum.

Cardiomyocytes were generated from hESCs with the ABCX method as previously described (36, 37). In brief hESCs (RUES2, Female line, Rockefeller University, NIH registry number 0013) were maintained in feeder-free irradiated mouse embryonic fibroblast (iMEF)-conditioned media containing bFGF (4 ng/ml, Peprotech). Cells were seeded as single cells ($1\times10^5$/cm²) on Matrigel™ (BD) coated plates with conditioned media including Chiron 99021 (1 µM, Cayman Chemical) and ROCK inhibitor (Y27632). The following day (day 0), the media was aspirated and cells were fed with RPMI media supplemented with B27 (Invitrogen) containing Activin A (100 ng/ml) for 18 hours. On day 1, media was aspirated and RPMI media plus B27 containing BMP4 (5 ng/ml) and Chiron 99021 (1 µM) for 48 hours. On day 3, media was aspirated and replaced with RPMI media plus B27 containing Xav 939 (1 µM, Torcis). On day 5, the medium was replaced with RPMI media plus B27. On day 7, the media was replaced with RPMI containing B27 with insulin (Invitrogen) and was consequently replaced every other day until termination of the protocol.

Cardiomyocytes were frozen down on day 21 and the same batch was used for the entirety of the study. Flow cytometry was performed on thawed cells using cTnT antibody (Thermo, MS-295-P) on BD FACSCanto II (Beckton Dickinson, San Jose, Calif.) and analyzed using FACS-Diva software (BD Biosciences), revealing a purity of 97.1%±0.5 (cTnT+, FIG. 1, panel C).

Epicardial cells were heat-shocked on the day prior to cell transplantation, and cardiomyocytes were heat-shocked prior to freezing, both for 30 minutes at 42.5° C. On the day of cell transplantation, epicardial cells and cardiomyocytes were enzymatically dispersed, counted and resuspended in 100 d volume per rat of Matrigel™ and pro-survival cocktail (PSC). PSC consisted of 50% (vol/vol) Matrigel™ and ZVAD-FMK (100 µM, Calbiochem), Bcl-XL (50 nM, Calbiochem), Cyclosporin A (200 nM, Wako Pure Chemicals), Pinacidil (50µ, Sigma) and IGF-1 (100 ng/ml, Peprotech). Cell preparations either contained Matrigel™ plus PSC as vehicle controls or $5\times10^6$ epicardial cells or $10\times10^6$ cardiomyocytes or the combination of $5\times10^6$ epicardial cells and $10\times10^6$ cardiomyocytes in Matrigel™/PSC.

*Mycoplasma* screening was performed on all cells on a regular basis and found to be negative.

Generation and functional assessment of 3D-EHT. In order to cast the tissue constructs, wells were fabricated using polydimethylsiloxane (PDMS) (PDMS, Sylgard 184; Dow Corning, Midland, Mich.). PDMS linker and base were mixed in a 1:10 mass-ratio and poured in laser-etched acrylic negative templates featuring 4 wells measuring 3×8×2 mm and containing a 1 mm diameter post positioned at 1.5 mm from each end. The PDMS was baked at 65° C. overnight, removed from the negatives, and then autoclaved. Prior to casting the tissues, the PDMS wells were treated with 5% pluronic acid F127 solution (Sigma, P2443) for 1 hour.

Cardiomyocytes used for construct studies were frozen down on day 21 of the differentiation and given 5 days in culture to recover. During construct casting, cardiomyocytes and epicardial cells were trypsinized and mixed in a collagen gel containing 10×RPMI-1640 medium (Sigma), NaOH, Geltrex™ (Invitrogen, A1413202), collagen I Rat Protein (Gibco Life Technologies, A1048301) and water. The cell-gel solution was poured into the PDMS wells and allowed to solidify for 30 minutes at 37° C. Constructs were then fed with 7 ml of RPMI media plus B27 plus insulin every other day, and spontaneous contractions were observed within 7 days. All constructs were cultured for 14 days, fixed with 4% PFA, treated with 30% sucrose at 4° C. overnight and finally cryoembedded and sectioned.

For assessment of $Ca^{2+}$-handling 14 day-old constructs were incubated with fluo-4, AM (Invitrogen, Molecular Probes) for 20 minutes at 37° C. Videos were taken with a Sony Handycam™ (Vixia HFS20) attached on a fluorescent microscope (Nikon Eclipse TS100). Videos were subsequently converted to frames, imported and analyzed using Image J software.

Force measurement of constructs was performed after 2 weeks in culture, as previously described (38). In brief, constructs were removed from the PDMS wells and suspended between a force transducer (Aurora Scientific, model 400A) and length controller (Aurora Scientific, model 312B). To assess the Frank-Starling relationship, constructs were stretched from their resting length to an additional 25% strain in 6 steps while being bathed in a HEPES-buffered Tyrode solution held at 37° C. Force traces were first recorded without electrical stimulation and subsequently with 1, 1.5, 2 and 3 Hz at 5V and 50 ms pulse duration. Passive tension and active force traces were recorded and analyzed using customized LabView and MATLAB software.

Myocardial infarction and cell transplantation. All studies were approved by the University of Washington Animal Care and Use Committee (IACUC; protocol number 2225-04) and were conducted in accordance with US NIH Policy on Humane Care and Use of Laboratory Animals. The study design comprised two feasibility studies and one definitive study. The first study was designed to assess the acute survival and fate of hESC-derived epicardial cells. Animals either received $2\times10^6$ (n=4) or $4\times10^6$ (n=4) epicardial cells or a vehicle control injection (n=4). In a second feasibility study, designed to assess long term survival of epicardial cells and their function animals randomly received either a $6\times10^6$ epicardial cells (n=6) or a vehicle control injection (n=4). The definitive study was conducted to assess the trophic effect of the epicardium on cardiomyocytes. The definitive study design comprised the following four study arms: $5\times10^6$ epicardial cells (n=15), $10\times10^6$ cardiomyocytes (n=14), $5\times10^6$ epicardial cells plus $10\times10^6$ cardiomyocytes (n=14) or vehicle control (n=13).

The protocol for cell implantation has been previously detailed (6, 39). In brief, male athymic Sprague Daley rats (Charles River) underwent anesthesia through intraperitoneal injection of 68.2 mg/kg ketamine and 4.4 mg/kg xylazine, intubated and mechanically ventilated with room air and supplemented oxygen. A second dose of ketamine and xylazine was administered 20 minutes later. Animals were placed on a heating pad connected with a rectal temperature probe, which ensured maintenance of body temperature at 37° C. A thoracotomy was subsequently performed, the anterior surface of the heart was exposed and the left anterior descending (LAD) coronary artery was visualized. The LAD was consequently ligated for 60 minutes after which the ligation was removed, the animals were reperfused, and the chest aseptically closed. Four-days post myocardial infarction, animals were anesthetized with isoflurane before undergoing a second thoracotomy for intramyocardial cell transplantations. Animals were subsequently randomly assigned to one of the treatment groups and cells were injected into the infarct zone. The chest was subsequently closed and the animals were postoperatively monitored.

To optimize graft retention animals received a subcutaneous injection of 5 mg/kg Cyclosporine A on the day before surgery until 7 days after the surgery. To assess cell proliferation in the cell grafts, animals were injected with of 50 mg/kg BrdU on days 1 4, 7, and 14 post cell injection. The cohort of animals that was followed up for three months additionally received one BrdU injection 24 hours before the termination of the study.

Echocardiography. All animals underwent echocardiographic exams at baseline before myocardial infarction, 4 days after the infarct and at 28 days after cell transplantation.

conjugated secondary antibodies for 45 minutes at room temperature (RT) before staining with 49.6-diamidino-2-phenylindole (DAPI) for 10 minutes to visualize the nuclei. For immunohistochemistry (IHC), hearts were excised post mortem and prepared as described (39). Briefly, hearts were washed in PBS, kept in saturated KCl for 20 minutes and subsequently fixed in 4% PFA and were paraffin sectioned (5 mm). For IHC stainings, slides were deparaffinized, underwent heat-mediated antigen retrieval for 15 minutes and were blocked with 5% BSA/PBS containing 0.3% Triton X-100 for one hour at RT. Next, the slides were incubated with primary antibodies at 4° C. overnight and fluorescent secondary antibodies were applied at room temperature for 60 minutes on the consecutive day. All antibodies used for immunocytochemistry and immunohistochemistry studies are detailed in Table 3.

TABLE 3

Primary Antibodies used for ICC and IHC

| Antibody | Application | Species | Dilution | Manufacturer (Cat#) |
|---|---|---|---|---|
| Vimentin, Clone Vim 3B4 | ICC/IHC | Mouse | 1:100 | Dako (M7020) |
| Cytokeratin | ICC/IHC | Rabbit | 1:150 | Dako (Z0622) |
| GFP | IHC | Goat | 1:500 | Novus (NB-100-1770) |
| Human mitochondria, clone 113-1 | IHC | | 1:100 | Millipore (MAB1273) |
| Fibronectin | IHC | Rabbit | 1:250 | Abcam (ab2413) |
| Alpha-Actinin | IHC | Rabbit | 1:800 | Abcam (ab68167) |
| Cardiac Troponin I | IHC | Rabbit | 1:200 | Abcam (ab47003) |
| Cardiac Troponin T | IHC | Goat | 1:200 | Abcam (ab64623) |
| Cardiac Troponin T | IHC | Mouse | 1:200 | Abcam (ab8295) |
| Connexin 43 | IHC | Mouse | 1:500 | Millipore (MAB3067) |
| Connexin 43 | IHC | Rabbit | 1:500 | Abcam (ab11370) |
| Beta-myosin Heavy Chain, Clone A4.951 | IHC | Mouse | Full strength | Human Hybridoma Bank |
| CD31/PECAM-1 | IHC | Rabbit | 1:100 | Novus (NB100-2284) |
| Biotinylated human Lectin | IHC | N/A | 1:1000 | Vector (B-1065) |
| S100A4 | IHC | Rabbit | 1:50 | Abcam (ab27957_) |
| DDR2 | IHC | Goat | 1:50 | Santa Cruz (sc-7555) |
| Smooth Muscle Alpha Actin | IHC | Mouse | 1:200 | Dako (M0851) |
| Smooth Muscle Alpha Actin | IHC | Goat | 1:200 | Abcam (ab21027) |
| Anti-BrdU-POD, Clone BMG-6H8 | IHC | Mouse | 1:40 | Roche (11 585 860 001) |

Figures 13A, 13B:
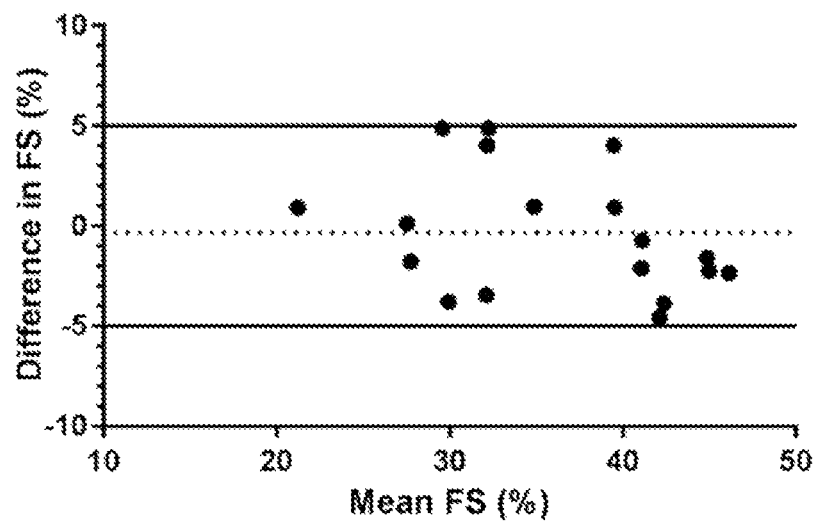
FIGS. 13A-13D. Validation of functional analysis.
Figures 13C, 13D:
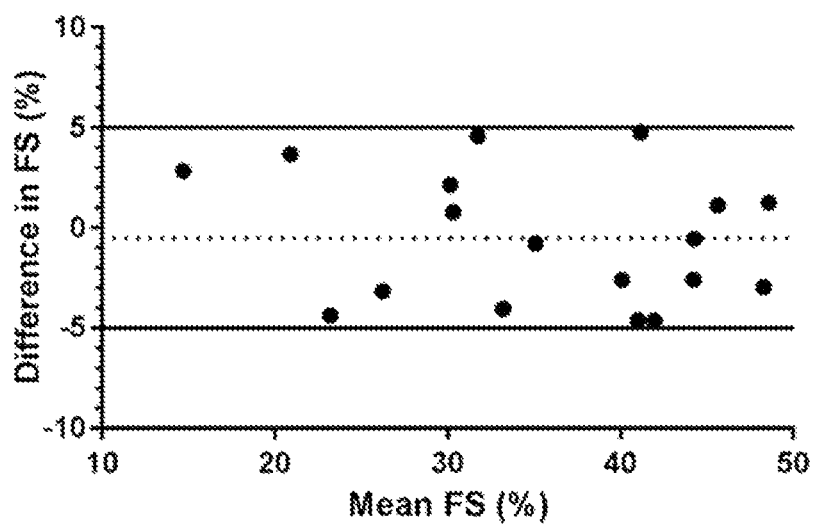
Figure 14A:
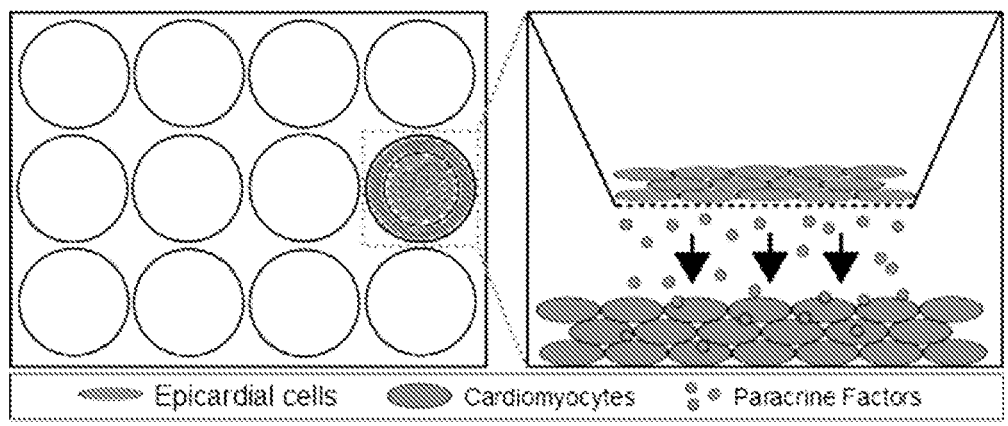
FIGS. 14A-14C. Human ES-derived epicardial cells also promote cardiomyocyte maturation in a paracrine fashion.
Figure 14B:
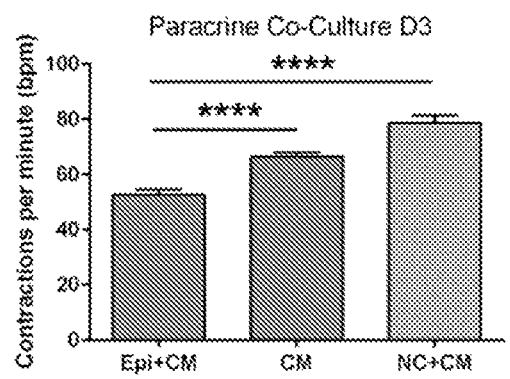
Figure 14C:
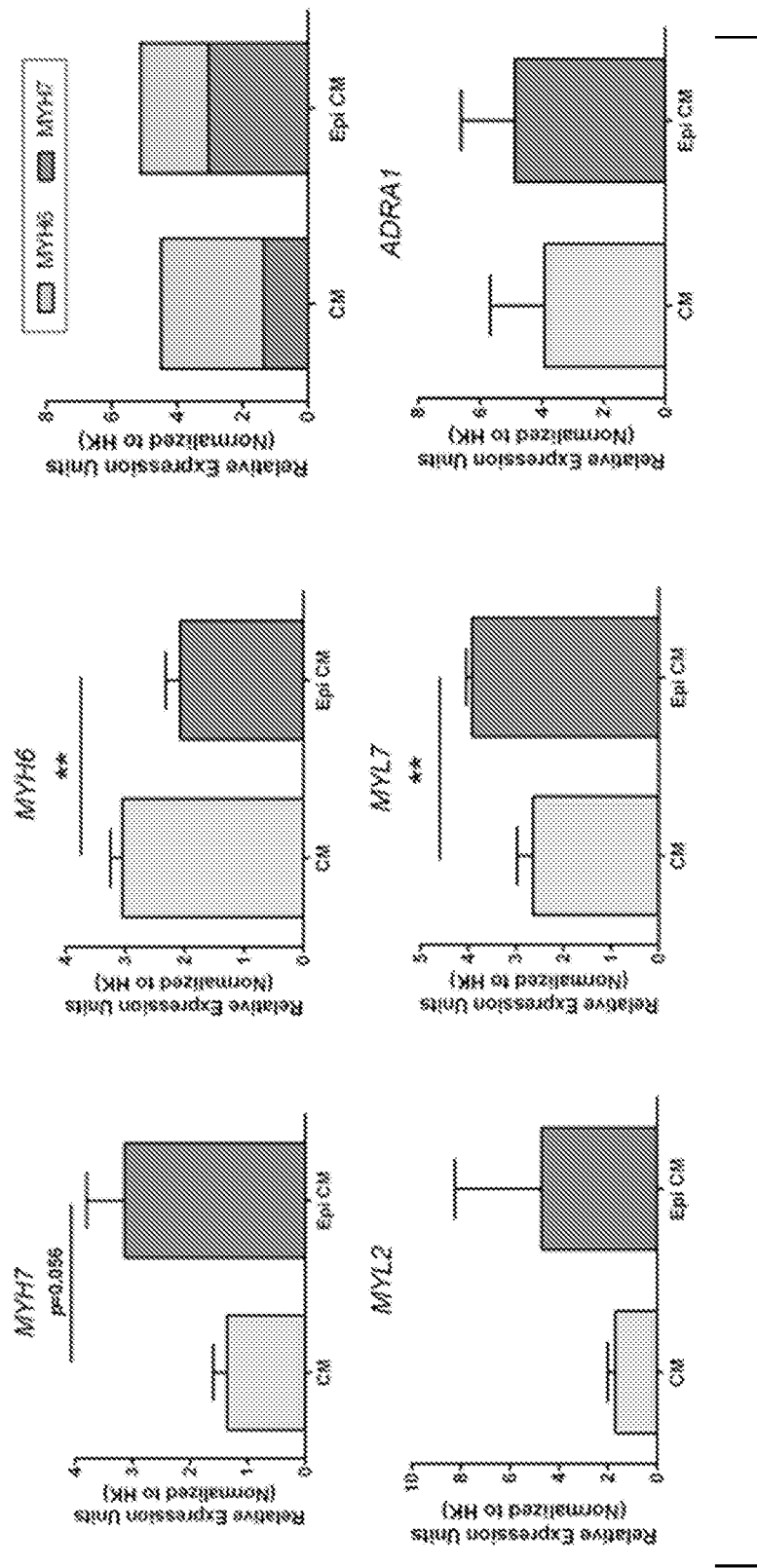
Figure 15A:
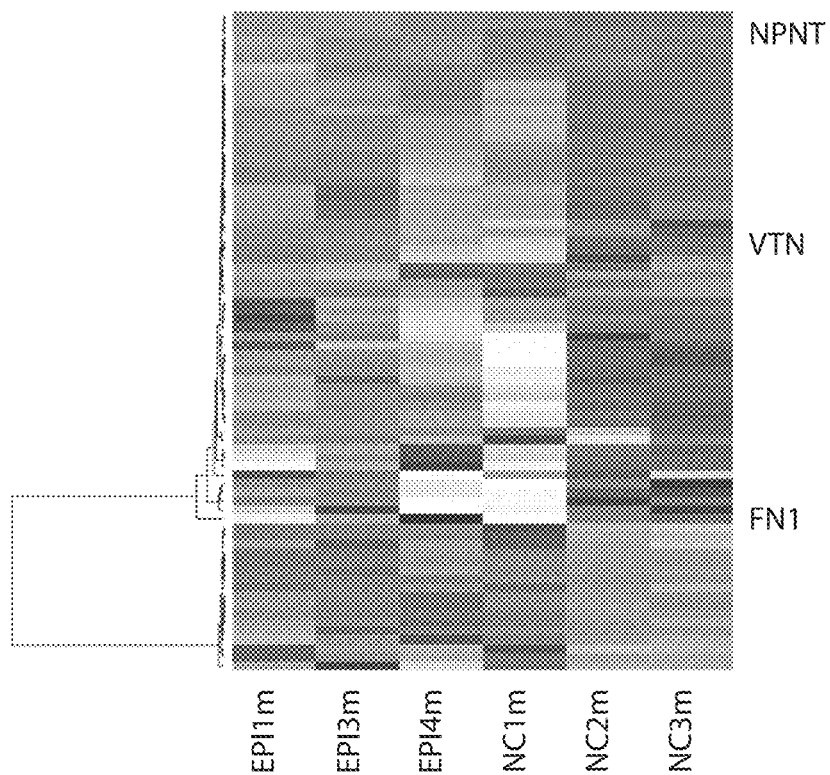
FIGS. 15A-15D. Investigation of mediators of epicardial driven heart regeneration.
Figure 15B:
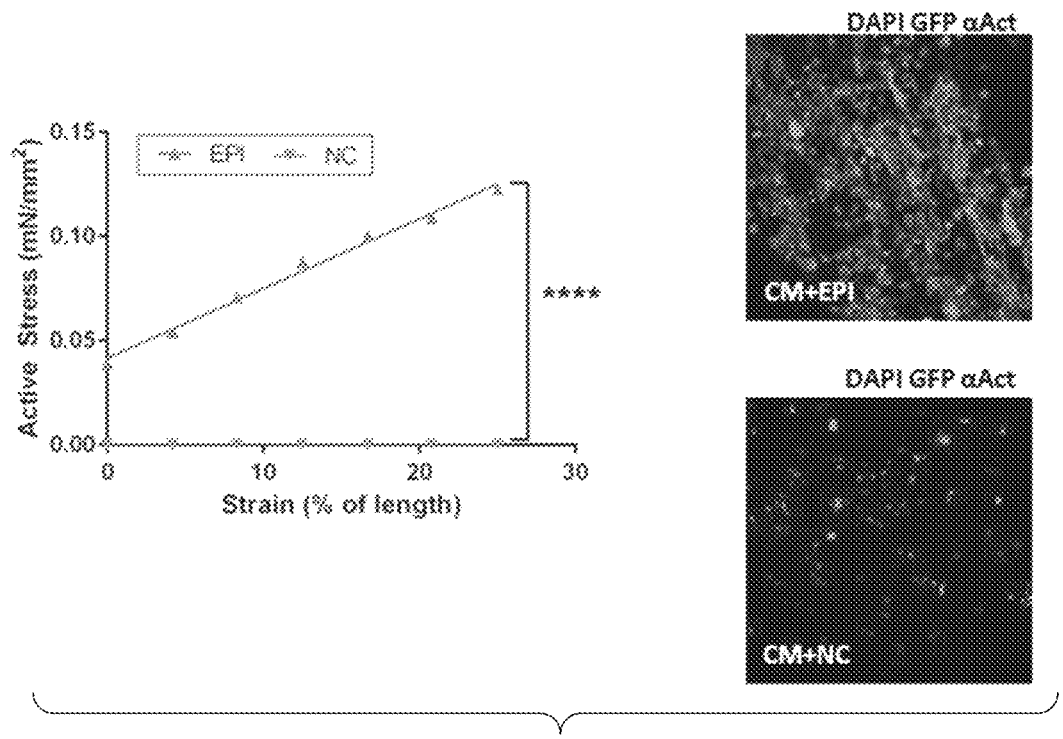
Figure 15C:
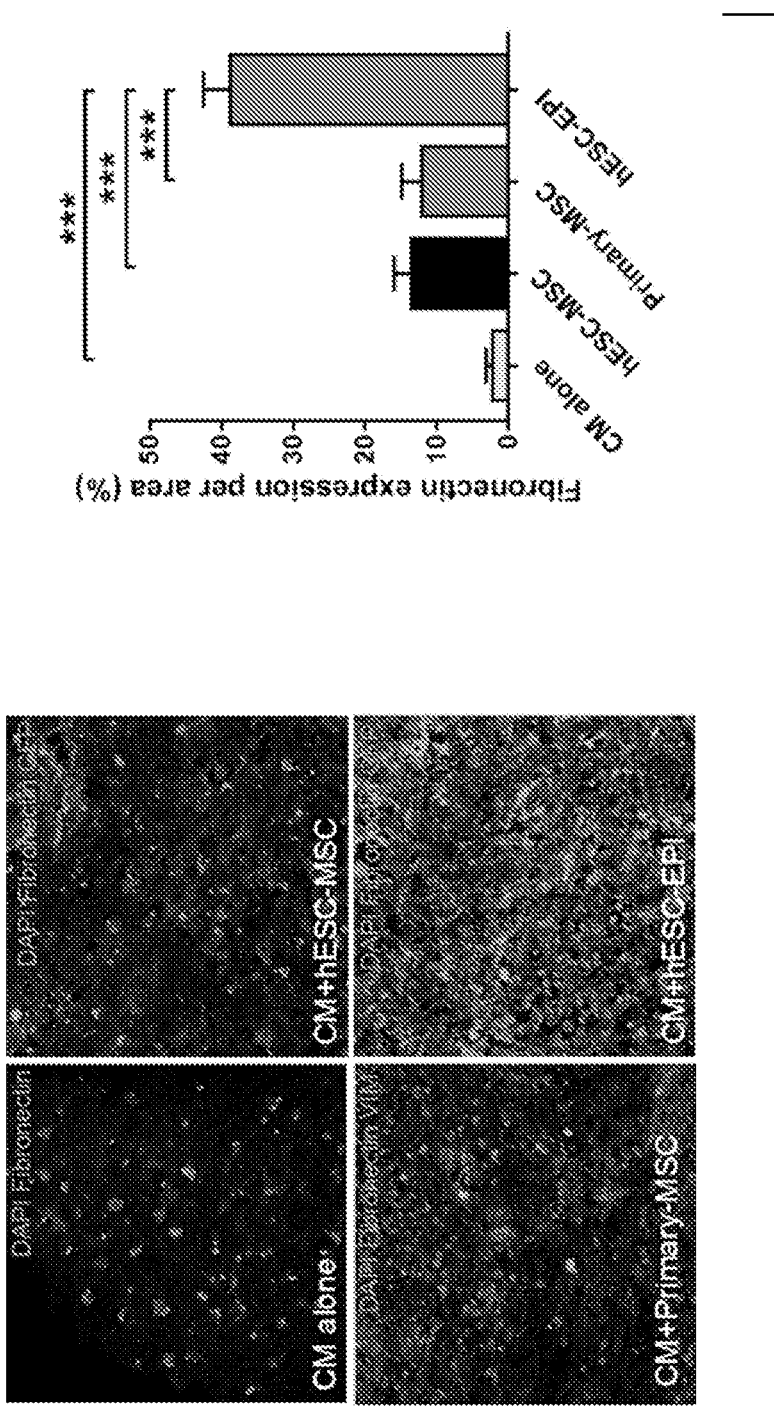
Figure 15D:
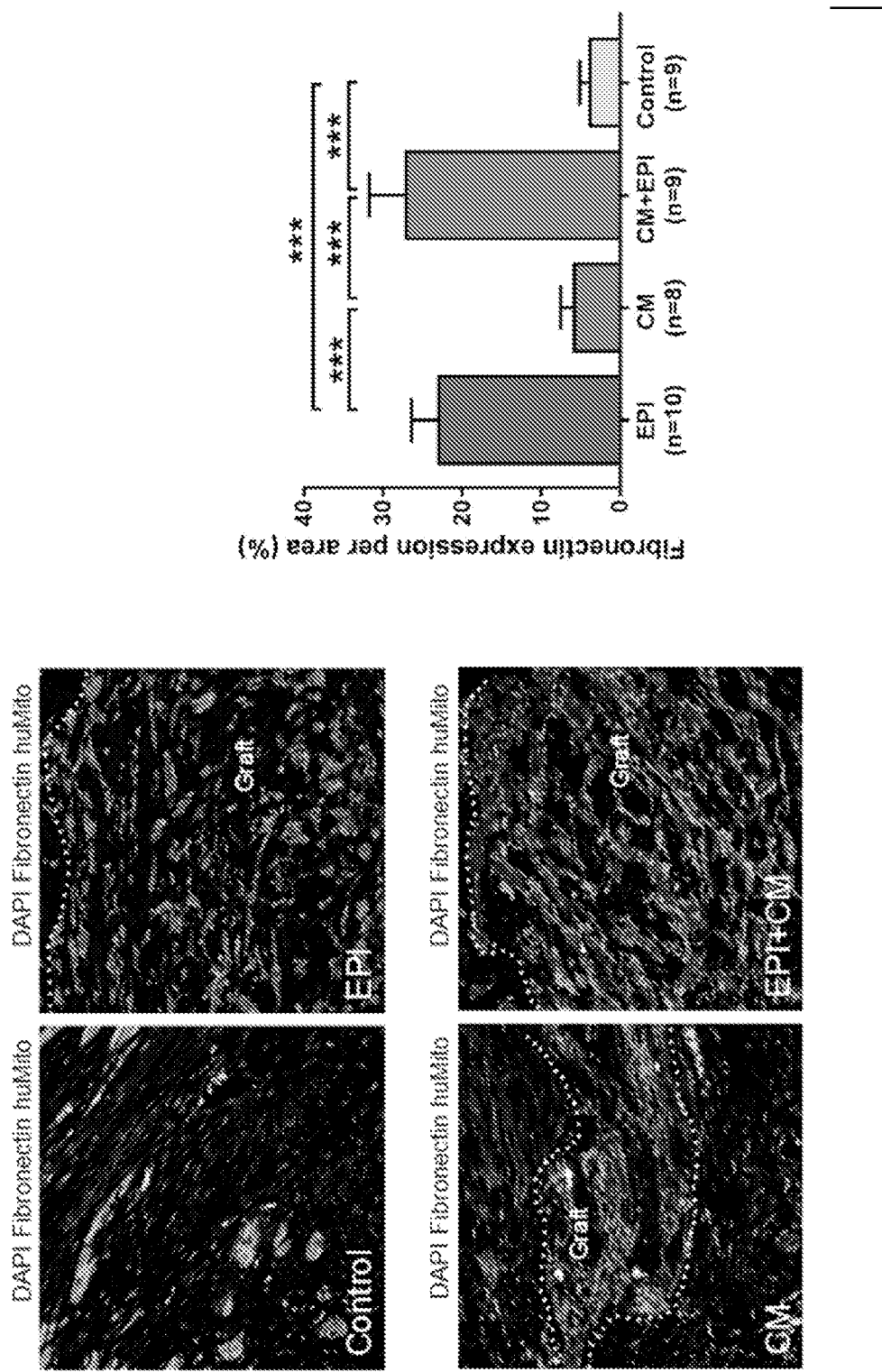

A subset of animals was maintained and imaged at 84-days post-transplantation. Briefly, animals were lightly anesthetized with inhaled isoflurane (Novaplus) and scanned by transthoracic echocardiography (GE Vivid 7) using a 10S (10 MHz) pediatric probe. The endpoints acquired comprised fractional shortening (%), left-ventricular diastolic dimension (LVEDD) and left-ventricular systolic dimension (LVESD). LVDD and LVESD are expressed in millimeters (mm). The images were anonymized and a primary reader made measurements in a blinded manner. For validation purposes, an independent investigator analyzed a sample set of images in a blinded fashion prior to analysis of the entire dataset and at the end to ensure consistency in measurements. The respective Bland-Altman plots and Intra Class Correlation Coefficients of these two tests are presented in FIG. 13.

Immunocytochemistry and Immunohistochemistry. For immunocytochemistry, cells were fixed in 4% paraformaldehyde (PFA), permeabilized with 0.5% Triton X100 in phosphate-buffered saline (PBS) and blocked in 3% BSA/PBS for 45 minutes at room temperature. Primary antibody incubations were performed at 4° C. overnight. The next day, cells were washed and incubated with Alexa-Fluor Infarct and graft quantification. To assess infarct size, slides were stained with picrosirius red/fast-green stain. Subsequently, picrosirius red positive area was quantified in the infarcted sections and normalized to the left ventricular area in each section. For quantification of cardiac graft size, slides were stained overnight with human Mitochondria antibody (Novus) and α-Actinin (Abcam) to quantify the size of the human cardiac grafts followed by a 1-hour incubation with Alexa Fluor-488 donkey anti-rabbit and Alexa Fluor-568 goat anti-mouse secondary antibodies (Invitrogen). The corresponding graft size was then normalized to the size of the infarct area. All animals were used for analysis except one animal in the CM only study arm, which did not exhibit a detectable graft. Images were acquired on a Nikon TiE Inverted Widefield Fluorescence High-Resolution Microscope. To assess epicardial grafts, anti-GFP (Novus) and anti-human Mitochondria (Novus) antibodies were used. For investigation of epithelial to mesenchymal transition of grafted epicardial cells, slides were stained with antibodies directed against GFP (Novus), Vimentin (Dako) and Wide-spectrum Cytokeratin (Dako). To determine the fate of epicardial cells, slides were co-stained with antibodies directed against human Mitochondria (Novus) and cardiomyocyte (alpha-Actinin (Abcam)), endothelial cells (human Lectin (*Ulex europaeus*, Vector)), smooth muscle cells, (Smooth Muscle α-Actin (Dako)), or fibroblasts (S100A4 (Abcam)). To detect cardiac grafts, antibodies directed either against human mitochondria and α-Actinin or against β-MHC (Developmental Studies Hybridoma Bank) were used. For assessment of microvascular density, slides were stained with CD31/PECAM (Novus) and either β-MHC (Developmental Studies Hybridoma Bank) or cTnI (Abcam). For quantification of microvascular density in cardiac grafts, the infarct zone and the non-injured border zone, the number of lumen was counted and normalized to the area of cardiac graft size, area of cardiac infarct or the area of non-injured myocardium respectively. All images were acquired in technical replicates per animal on a Zeiss LSM700 microscope using ZEN software and were subsequently analyzed using Image J software.

TABLE 4

Intraclass Correlation Coefficient Values (95% Confidence Intervals in Parenthesis).

| Inter-observer agreement | Uninjured | Day 4 | Day 28 | Total |
|---|---|---|---|---|
| Test 1 | | | | |
| | 0.77 (−0.18-0.96) | 0.94 (0.56-0.99) | 0.84 (−0.39-0.97) | 0.95 (0.88-0.98) |
| Test 2 | | | | |
| | 0.83 (−0.44-0.97) | 0.96 (0.41-0.99) | 0.96 (0.75-0.99) | 0.97 (0.93-0.99) |

Statistics. All in vitro studies were performed as three biological replicates (independent experiments), each of which was performed in technical replicates. All in vivo data specifically state the number of animals assessed for each time point. The normal distribution of the values was confirmed using the D'Agostino & Pearson omnibus normality test where appropriate. Variance between samples was tested with the Brown-Forsythe test. Statistical testing was performed using an unpaired t-test for two group comparisons and a paired t-test for comparison of two paired groups. For multiple-group comparison, a one-way ANOVA with a post-hoc Tukey test was used if the group variance was equal and a Kruskall-Wallis test with Dunn's correction for multiple comparisons was applied for groups with unequal variance. Measuring two-sided significance, a p-value of 0.05 was considered statistically significant. All analysis was performed using GraphPad Prism software in a blinded fashion. All results are expressed as mean±SD., unless otherwise stated.

For all in vivo experiments, group sizes were estimated based on previous study variance. No formal statistical methods were applied for sample size calculation. While no formal methods of randomization were used, the animals were randomly selected by a technician who was blinded to treatment. Analysis of all histology slides as well as all functional data was performed in a blinded fashion. Death was the only exclusion criteria for further histologic and functional analysis.

REFERENCES

1. Braunwald E. Shattuck lecture—cardiovascular medicine at the turn of the millennium: triumphs, concerns, and opportunities. *The New England journal of medicine* 1997; 337:1360-1369.
2. Mozaffarian D, Benjamin E J, Go A S, Arnett D K, Blaha M J, Cushman M, Das S R, de Ferranti S, Despres J P, Fullerton H J, Howard V J, Huffman M D, Isasi C R, Jimenez M C, Judd S E, Kissela B M, Lichtman J H, Lisabeth L D, Liu S, Mackey R H, Magid D J, McGuire D K, Mohler E R, 3rd, Moy C S, Muntner P, Mussolino M E, Nasir K, Neumar R W, Nichol G, Palaniappan L, Pandey D K, Reeves M J, Rodriguez C J, Rosamond W, Sorlie P D, Stein J, Towfighi A, Turan T N, Virani S S, Woo D, Yeh R W, Turner M B. Heart Disease and Stroke Statistics-2016 Update: A Report From the American Heart Association. *Circulation* 2016; 133:e38-360.
3. McMurray J J, Petrie M C, Murdoch D R, Davie A P. Clinical epidemiology of heart failure: public and private health burden. *European heart journal* 1998; 19 Suppl P:P9-16.
4. Burridge P W, Matsa E, Shukla P, Lin Z C, Churko J M, Ebert A D, Lan F, Diecke S, Huber B, Mordwinkin N M, Plews J R, Abilez O J, Cui B, Gold J D, Wu J C. Chemically defined generation of human cardiomyocytes. *Nature methods* 2014; 11:855-860.
5. Lian X, Hsiao C, Wilson G, Zhu K, Hazeltine L B, Azarin S M, Raval K K, Zhang J, Kamp T J, Palecek S P. Robust cardiomyocyte differentiation from human pluripotent stem cells via temporal modulation of canonical Wnt signaling. *Proceedings of the National Academy of Sciences of the United States of America* 2012; 109:E1848-1857.
6. Laflamme M A, Chen K Y, Naumova A V, Muskheli V, Fugate J A, Dupras S K, Reinecke H, Xu C, Hassanipour M, Police S, O'Sullivan C, Collins L, Chen Y, Minami E, Gill E A, Ueno S, Yuan C, Gold J, Murry C E. Cardiomyocytes derived from human embryonic stem cells in pro-survival factors enhance function of infarcted rat hearts. *Nature biotechnology* 2007; 25:1015-1024.
7. Patsch C, Challet-Meylan L, Thoma E C, Urich E, Heckel T, O'Sullivan J F, Grainger S J, Kapp F G, Sun L, Christensen K, Xia Y, Florido M H, He W, Pan W, Prummer M, Warren C R, Jakob-Roetne R, Certa U, Jagasia R, Freskgard P O, Adatto I, Kling D, Huang P, Zon L I, Chaikof E L, Gerszten R E, Graf M, Iacone R, Cowan C A. Generation of vascular endothelial and smooth muscle cells from human pluripotent stem cells. *Nature cell biology* 2015; 17:994-1003.
8. Orlova V V, van den Hil F E, Petrus-Reurer S, Drabsch Y, Ten Dijke P, Mummery C L. Generation, expansion and functional analysis of endothelial cells and pericytes derived from human pluripotent stem cells. *Nature protocols* 2014; 9:1514-1531.

Cheung C, Bernardo A S, Trotter M W, Pedersen R A, Sinha S. Generation of human vascular smooth muscle subtypes provides insight into embryological origin-dependent disease susceptibility. *Nature biotechnology* 2012; 30:165-173.
10. Iyer D, Gambardella L, Bernard W G, Serrano F, Mascetti V L, Pedersen R A, Talasila A, Sinha S. Robust derivation of epicardium and its differentiated smooth muscle cell progeny from human pluripotent stem cells. *Development* (Cambridge, England) 2015; 142:1528-1541.
11. Witty A D, Mihic A, Tam R Y, Fisher S A, Mikryukov A, Shoichet M S, Li R K, Kattman S J, Keller G. Generation of the epicardial lineage from human pluripotent stem cells. *Nature biotechnology* 2014; 32:1026-1035.
12. Shiba Y, Fernandes S, Zhu W Z, Filice D, Muskheli V, Kim J, Palpant N J, Gantz J, Moyes K W, Reinecke H, Van Biber B, Dardas T, Mignone J L, Izawa A, Hanna R, Viswanathan M, Gold J D, Kotlikoff M I, Sarvazyan N, Kay M W, Murry C E, Laflamme M A. Human ES-cell-derived cardiomyocytes electrically couple and suppress arrhythmias in injured hearts. *Nature* 2012; 489:322-325.
13. Chong J J, Yang X, Don C W, Minami E, Liu Y W, Weyers J J, Mahoney W M, Van Biber B, Palpant N J, Gantz J A, Fugate J A, Muskheli V, Gough G M, Vogel K W, Astley C A, Hotchkiss C E, Baldessari A, Pabon L, Reinecke H, Gill E A, Nelson V, Kiem H P, Laflamme M A, Murry C E. Human embryonic-stem-cell-derived cardiomyocytes regenerate non-human primate hearts. *Nature* 2014.
14. Shiba Y, Gomibuchi T, Seto T, Wada Y, Ichimura H, Tanaka Y, Ogasawara T, Okada K, Shiba N, Sakamoto K, Ido D, Shiina T, Ohkura M, Nakai J, Uno N, Kazuki Y, Oshimura M, Minami I, Ikeda U. Allogeneic transplantation of iPS cell-derived cardiomyocytes regenerates primate hearts. *Nature* 2016; 538:388-391.
15. van den Berg C W, Okawa S, Chuva de Sousa Lopes S M, van Iperen L, Passier R, Braam S R, Tertoolen L G, del Sol A, Davis R P, Mummery C L. Transcriptome of human foetal heart compared with cardiomyocytes from pluripotent stem cells. *Development* (Cambridge, England) 2015; 142:3231-3238.
16. Guadix J A, Carmona R, Munoz-Chapuli R, Perez-Pomares J M. In vivo and in vitro analysis of the vasculogenic potential of avian proepicardial and epicardial cells. *Developmental dynamics: an official publication of the American Association of Anatomists* 2006; 235:1014-1026.
17. Gittenberger-de Groot A C, Vrancken Peeters M P, Mentink M M, Gourdie R G, Poelmann R E. Epicardium-derived cells contribute a novel population to the myocardial wall and the atrioventricular cushions. *Circulation research* 1998; 82:1043-1052.
18. Dettman R W, Denetclaw W, Jr., Ordahl C P, Bristow J. Common epicardial origin of coronary vascular smooth muscle, perivascular fibroblasts, and intermyocardial fibroblasts in the avian heart. *Developmental biology* 1998; 193:169-181.
20. Manner J. Does the subepicardial mesenchyme contribute myocardioblasts to the myocardium of the chick embryo heart? A quail-chick chimera study tracing the fate of the epicardial primordium. *The Anatomical record* 1999; 255:212-226.
21. Ieda M, Tsuchihashi T, Ivey K N, Ross R S, Hong T T, Shaw R M, Srivastava D. Cardiac fibroblasts regulate myocardial proliferation through beta1 integrin signaling. *Developmental cell* 2009; 16:233-244.
22. Cai C L, Martin J C, Sun Y, Cui L, Wang L, Ouyang K, Yang L, Bu L, Liang X, Zhang X, Stallcup W B, Denton C P, McCulloch A, Chen J, Evans S M. A myocardial lineage derives from Tbx18 epicardial cells. *Nature* 2008; 454:104-108.
23. Gittenberger-de Groot A C, Vrancken Peeters M P, Bergwerff M, Mentink M M, Poelmann R E. Epicardial outgrowth inhibition leads to compensatory mesothelial outflow tract collar and abnormal cardiac septation and coronary formation. *Circulation research* 2000; 87:969-971.
24. Eid H, Larson D M, Springhom J P, Attawia M A, Nayak R C, Smith T W, Kelly R A. Role of epicardial mesothelial cells in the modification of phenotype and function of adult rat ventricular myocytes in primary coculture. *Circulation research* 1992; 71:40-50.
25. Weeke-Klimp A, Bax N A, Bellu A R, Winter E M, Vrolijk J, Plantinga J, Maas S, Brinker M, Mahtab E A, Gittenberger-de Groot A C, van Luyn M J, Harmsen M C, Lie-Venema H. Epicardium-derived cells enhance proliferation, cellular maturation and alignment of cardiomyocytes. *Journal of molecular and cellular cardiology* 2010; 49:606-616.
26. Ogle B M, Bursac N, Domian I, Huang N F, Menasche P, Murry C E, Pruitt B, Radisic M, Wu J C, Wu S M, Zhang J, Zimmermann W H, Vunjak-Novakovic G. Distilling complexity to advance cardiac tissue engineering. *Science translational medicine* 2016; 8:342ps313.
27. Lepilina A, Coon A N, Kikuchi K, Holdway J E, Roberts R W, Burns C G, Poss K D. A dynamic epicardial injury response supports progenitor cell activity during zebrafish heart regeneration. *Cell* 2006; 127:607-619.
28. Porrello E R, Mahmoud A I, Simpson E, Hill J A, Richardson J A, Olson E N, Sadek H A. Transient regenerative potential of the neonatal mouse heart. *Science* (New York, N.Y.) 2011; 331:1078-1080.
29. Ruiz-Villalba A, Simon A M, Pogontke C, Castillo M I, Abizanda G, Pelacho B, Sanchez-Dominguez R, Segovia J C, Prosper F, Perez-Pomares J M. Interacting resident epicardium-derived fibroblasts and recruited bone marrow cells form myocardial infarction scar. *Journal of the American College of Cardiology* 2015; 65:2057-2066.
30. Moore-Morris T, Guimaraes-Camboa N, Banerjee I, Zambon A C, Kisseleva T, Velayoudon A, Stallcup W B, Gu Y, Dalton N D, Cedenilla M, Gomez-Amaro R, Zhou B, Brenner D A, Peterson K L, Chen J, Evans S M. Resident fibroblast lineages mediate pressure overload-induced cardiac fibrosis. *The Journal of clinical investigation* 2014; 124:2921-2934.
31. Hedhli N, Huang Q, Kalinowski A, Palmeri M, Hu X, Russell R R, Russell K S. Endothelium-derived neuregulin protects the heart against ischemic injury. *Circulation* 2011; 123:2254-2262.
31. Leucker T M, Bienengraeber M, Muravyeva M, Baotic I, Weihrauch D, Brzezinska A K, Warltier D C, Kersten J R, Pratt P F, Jr. Endothelial-cardiomyocyte crosstalk enhances pharmacological cardioprotection. *Journal of molecular and cellular cardiology* 2011; 51:803-811.
32. Wang J, Karra R, Dickson A L, Poss K D. Fibronectin is deposited by injury-activated epicardial cells and is necessary for zebrafish heart regeneration. *Developmental biology* 2013; 382:427-435.
33. Winter E M, Grauss R W, Hogers B, van Tuyn J, van der Geest R, Lie-Venema H, Steijn R V, Maas S, DeRuiter M C, deVries A A, Steendijk P, Doevendans P A, van der Laarse A, Poelmann R E, Schalij M J, Atsma D E, Gittenberger-de Groot A C. Preservation of left ventricular function and attenuation of remodeling after transplantation of human epicardium-derived cells into the infarcted mouse heart. *Circulation* 2007; 116:917-927.

34. Winter E M, van Oorschot A A, Hogers B, van der Graaf L M, Doevendans P A, Poelmann R E, Atsma D E, Gittenberger-de Groot A C, Goumans M I. A new direction for cardiac regeneration therapy: application of synergistically acting epicardium-derived cells and cardiomyocyte progenitor cells. *Circulation Heart failure* 2009; 2:643-653.

35. Ye L, Chang Y H, Xiong Q, Zhang P, Zhang L, Somasundaram P, Lepley M, Swingen C, Su L, Wendel J S, Guo J, Jang A, Rosenbush D, Greder L, Dutton J R, Zhang J, Kamp T J, Kaufman D S, Ge Y, Zhang J. Cardiac repair in a porcine model of acute myocardial infarction with human induced pluripotent stem cell-derived cardiovascular cells. *Cell stem cell* 2014; 15:750-761.

36. Hofsteen P, Robitaille A M, Chapman D P, Moon R T, Murry C E. Quantitative proteomics identify DAB2 as a cardiac developmental regulator that inhibits WNT/beta-catenin signaling. *Proceedings of the National Academy of Sciences of the United States of America* 2016; 113: 1002-1007.

37. Palpant N J, Hofsteen P, Pabon L, Reinecke H, Murry C E. Cardiac development in zebrafish and human embryonic stem cells is inhibited by exposure to tobacco cigarettes and e-cigarettes. *PloS one* 2015; 10:e0126259.

38. Ruan J L, Tulloch N L, Saiget M, Paige S L, Razumova M V, Regnier M, Tung K C, Keller G, Pabon L, Reinecke H, Murry C E. Mechanical Stress Promotes Maturation of Human Myocardium From Pluripotent Stem Cell-Derived Progenitors. *Stem cells* (Dayton, Ohio) 2015; 33:2148-2157.

39. Gerbin K A, Yang X, Murry C E, Coulombe K L. Enhanced Electrical Integration of Engineered Human Myocardium via Intramyocardial versus Epicardial Delivery in Infarcted Rat Hearts. *PloS one* 2015; 10:e0131446.

40. Pittenger M F, Mackay A M, Beck S C, Jaiswal R K, Douglas R, Mosca J D, Moorman M A, Simonetti D W, Craig S, Marshak D R. Multilineage potential of adult human mesenchymal stem cells. *Science* (New York, N.Y.) 1999; 284:143-147.

The invention claimed is:

1. A transplant composition comprising human cardiomyocytes and in vitro-differentiated human epicardial cells or the differentiated progeny of such human epicardial cells, wherein upon administration to cardiac tissue of a subject in need thereof, the cardiomyocytes, the epicardial cells and/or their differentiated progeny engraft into the cardiac tissue.

2. The transplant composition of claim 1, wherein the human cardiomyocytes are in vitro-differentiated.

3. The transplant composition of claim 1, wherein the epicardial cells or their progeny, the cardiomyocytes, or both, are differentiated from embryonic stem cells or from induced pluripotent stem cells.

4. The transplant composition of claim 1, wherein the epicardial cells express fibronectin.

5. The transplant composition of claim 1, further comprising at least one of: cyclosporine A, pinacidil, or IGF-1.

6. The transplant composition of claim 1, wherein the cardiomyocytes are present at a ratio of 2:1, 1.5:1, 2.25:1, 2.5:1, 2.75:1, 3:1, 3.5:1, 4:1, 5:1, 7.5:1, 10:1, 15:1, 20:1, 1:1.5, 1:2, 1:2.25, 1:2.5, 1:2.75, 1:3, 1:3.5, 1:4, 1:5, 1:7.5, 1:10, 1:15, or 1:20 relative to the epicardial cells or progeny thereof.

7. A tissue particle comprising a human cardiomyocyte in physical association with an in vitro-differentiated human epicardial cell or differentiated progeny thereof, in a culture medium or a cocktail comprising at least one of: cyclosporine A, pinacidil, or IGF-1, wherein upon administration to cardiac tissue of a subject in need thereof, the cardiomyocyte, the epicardial cell and/or their differentiated progeny engraft into the cardiac tissue.

8. The tissue particle of claim 7, wherein the particle comprises from 2 to 2500 cells.

9. The tissue particle of claim 7, wherein the ratio of cardiomyocytes to epicardial cells or differentiated progeny thereof is 2:1, 1.5:1, 2.25:1, 2.5:1, 2.75:1, 3:1, 3.5:1, 4:1, 5:1, 7.5:1, 10:1, 15:1, 20:1, 1:1.5, 1:2, 1:2.25, 1:2.5, 1:2.75, 1:3, 1:3.5, 1:4, 1:5, 1:7.5, 1:10, 1:15, or 1:20.

10. The tissue particle of claim 7, wherein the epicardial cell, the cardiomyocyte, or both is/are differentiated from an embryonic stem cell(s) or an induced pluripotent stem cell(s).

11. A method of promoting engraftment of cardiomyocytes into cardiac tissue, comprising administering to cardiac tissue of a subject in need thereof a transplant composition of claim 1 or a tissue particle of claim 7.

12. The method of claim 11, wherein the subject has suffered a cardiac infarction.

13. A method of promoting a mature phenotype of transplanted human cardiomyocytes, the method comprising administering to cardiac tissue of a subject in need thereof a transplant composition of claim 1 or a tissue particle of claim 7.

14. The method of claim 13, wherein the subject has suffered a cardiac infarction.

15. The method of claim 13, wherein the cardiomyocyte maturity is indicated by at least one of: an increase in sarcomere length, an increase in cardiomyocyte diameter or length, expression of the cardiac isoform, cTnT, of troponin, or connexin 43 expression when cardiomyocytes are transplanted in admixture with epicardial cells, relative to cardiomyocyte transplantation alone.

* * * * *